(12) United States Patent
Amankulor et al.

(10) Patent No.: US 10,821,091 B2
(45) Date of Patent: Nov. 3, 2020

(54) RETINOID COMPOSITIONS AND METHODS OF INCREASING IMMUNE CELL-MEDIATED KILLING OF IDH MUTANT CANCER CELLS

(71) Applicant: UNIVERSITY OF PITTSBURGH—OF THE COMMONWEALTH SYSTEM OF HIGHER EDUCATION, Pittsburgh, PA (US)

(72) Inventors: Ndukaku Amankulor, Pittsburgh, PA (US); Aparna Rao, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 15/938,762

(22) Filed: Mar. 28, 2018

(65) Prior Publication Data
US 2018/0280335 A1 Oct. 4, 2018

Related U.S. Application Data

(60) Provisional application No. 62/477,868, filed on Mar. 28, 2017.

(51) Int. Cl.
| | |
|---|---|
| *A61K 31/203* | (2006.01) |
| *A61K 35/17* | (2015.01) |
| *A61K 35/00* | (2006.01) |
| *A61P 35/00* | (2006.01) |

(52) U.S. Cl.
CPC ............ *A61K 31/203* (2013.01); *A61K 35/17* (2013.01); *A61P 35/00* (2018.01)

(58) Field of Classification Search
None
See application file for complete search history.

(56) References Cited

PUBLICATIONS

Dang, L; Yen, K; Attar, EC; "IDH mutations in cancer and progress toward development of targeted therapeutics" Annals of Oncology, 27, 599-608, 2016 (Year: 2016).*

(Continued)

*Primary Examiner* — David W Berke-Schlessel
(74) *Attorney, Agent, or Firm* — Meunier Carlin & Curfman LLC

(57) ABSTRACT

Provided herein are methods of treating an IDH mutant cancer in a subject comprising administering to the subject a therapeutically effective amount of a composition comprising an all-trans retinoic acid (ATRA). In some embodiments, the methods increase an NK-cell-mediated immune response and/or a T cell-mediated immune response to the cancer. In some embodiments, the cancer is a glioma or a chondrosarcoma. In some embodiments, the expression of one or more NKG2D ligands (e.g., ULBP1 and ULBP3) is increased in a tumor microenvironment of the cancer. In some embodiments, CCL2 production, the number of NK cells, and/or apoptosis of tumor cells is increased in a tumor microenvironment of the cancer. In some embodiments, the subject has an IDH1 mutation at arginine 132 or an IDH2 mutation at arginine 172. In some embodiments, method reduces growth of a tumor.

14 Claims, 48 Drawing Sheets

Specification includes a Sequence Listing.

(56) References Cited

PUBLICATIONS

Poggi, A; et al; "Effective in vivo induction of NKG2D ligands in acute myeloid leukaemias by all-trans-retinoic acid or sodium valproate" Leukemia, 23, 641-648, 2009 (Year: 2009).*

Defer, Gilles-Louis; "All-trans retinoic acid in relapsing malignant gliomas: clinical and radiological stabilization associated with the appearance of intratumoral calcifications" Journal of Neuro-Oncology, 34, 169-177, 1997 (Year: 1997).*

Ishikawa, Eiichi; et al; "Autologous Natural Killer Cell Therapy for Human Recurrent Malignant Glioma" Anticancer Research, 24, 1861-1872, 2004 (Year: 2004).*

Chesnelong, "Isocitrate Dehydrogenase (IDH) Mutation in Gliomas," Next Generation Sequencing in Cancer Research, 2:441-458 (2015).

Chou, Arthur P., "Identification of Retinol Binding Protein 1 Promoter Hypermethylation in Isocitrate Dehydrogenase 1 and 2 Mutant Gliomas," JNIC, vol. 104, Issue 19, Oct. 3, 2012, pp. 1458-1469.

Amankulor, Nduka M. et al., "Mutant IDH1 regulates the tumor associated immune system in gliomas," Genes & Development 31:774-786, 2017, ISSN 0890-9369/17; www.genesdev.org.

Hartmann, Christian et al., "Type and frequency of IDH1 and IDH2 mutations are related to astrocytic and oligodendroglial differentiation and age: a study of 1,010 diffuse gliomas," Acta Neuropathol (2009) 118:469-474.

Boutzen, Helena et al., "Isocitrate dehydrogenase 1 mutations prime the all-trans retinoic acid myeloid differentiation pathway in acute myeloid leukemia," The Journal of Experimental Medicine, vol. 213, No. 4, pp. 483-497.

Yan, Hai et al., "IDH1 and IDH2 Mutations in Gliomas," The New England Journal of Medicine, Feb. 19, 2009, 360;8, pp. 765-773.

Amary, M. Fernanda et al., "Ollier disease and Maffucci syndrome are caused by somatic mosaic mutations of IDH1 and IDH2," Nature Genetics, vol. 23, No. 12, Dec. 2011, pp. 1262-1266.

Turcan, Sevin et al., "IDH1 mutation is sufficient to establish the glioma hypermethylator phenotype," National Institutes of Health, Nature; 483(7390); 479-483, 2012, doi:10.1038/jature10866, pp. 1-19.

Zhang, Xiaoran et al., "IDH mutant gliomas escape natural killer cell immune surveillance by downregulation of NKG2D ligand expression," Neuro-Oncology, 18(10), 1402-1412, 2016.

* cited by examiner

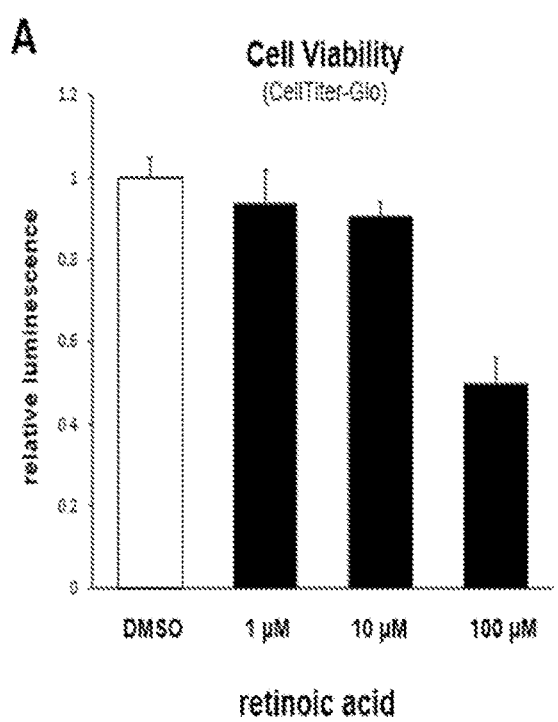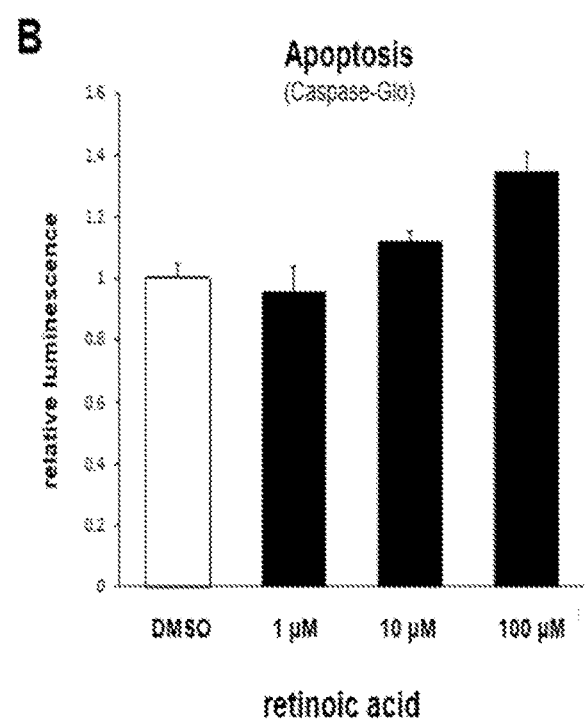
FIG. 11A                    FIG. 11B

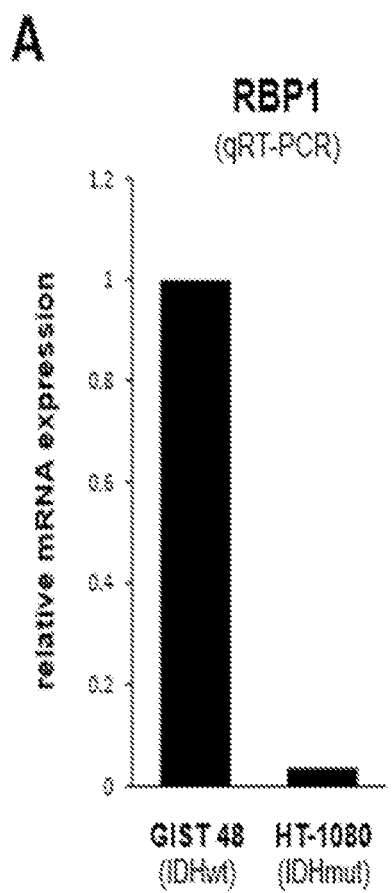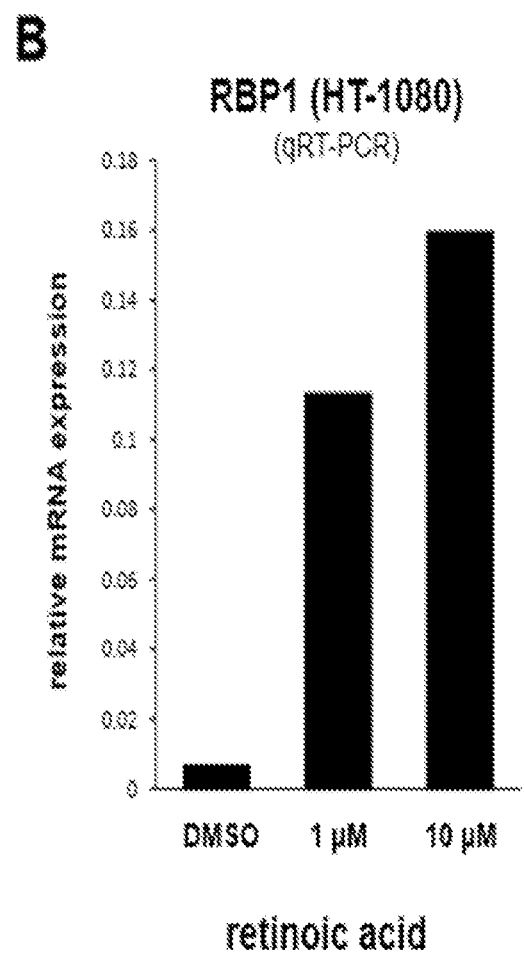
FIG. 11D
FIG. 11E

SEQUENCE LISTING

<160> NUMBER OF SEQ ID NOS: 2

<210> SEQ ID NO 1
<211> LENGTH: 2400
<212> TYPE: DNA
<213> ORGANISM: Homo sapiens

<400> SEQUENCE: 1

```
gggctgagga ggcggggcct gggaggggac aaagccggga agaggaaaag ctcggaccta      60
ccctgtggtc ccgggtttct gcagagtcta cttcagaagc ggaggcactg ggagtccggt     120
ttgggattgc caggctgtgg ttgtgagtct gagcttgtga gcggctgtgg cgccccaact     180
cttcgccagc atatcatccc ggcaggcgat aaactacatt cagttgagtc tgcaagactg     240
ggaggaactg gggtgataag aaatctattc actgtcaagg tttattgaag tcaaaatgtc     300
caaaaaaatc agtggcggtt ctgtggtaga gatgcaagga gatgaaatga cacgaatcat     360
ttgggaattg attaaagaga aactcatttt tccctacgtg gaattggatc tacatagcta     420
tgatttaggc atagagaatc gtgatgccac caacgaccaa gtcaccaagg atgctgcaga     480
agctataaag aagcataatg ttggcgtcaa atgtgccact atcactcctg atgagaagag     540
ggttgaggag ttcaagttga acaaatgtg gaaatcacca aatggcacca tacgaaatat     600
tctgggtggc acggtcttca gagaagccat tatctgcaaa aatatccccc ggcttgtgag     660
tggatgggta aaacctatca tcataggtcg tcatgcttat ggggatcaat acagagcaac     720
tgattttgtt gttcctgggc ctggaaaagt agagataacc tacacaccaa gtgacggaac     780
ccaaaaggtg acatacctgg tacataactt tgaagaaggt ggtggtgttg ccatggggat     840
gtataatcaa gataagtcaa ttgaagattt tgcacacagt tccttccaaa tggctctgtc     900
taagggttgg cctttgtatc tgagcaccaa aaacactatt ctgaagaaat atgatgggcg     960 tttttaaagac atctttcagg agatatatga caagcagtac aagtcccagt ttgaagctca    1020
aaagatctgg tatgagcata ggctcatcga cgacatggtg gcccaagcta tgaaatcaga    1080
gggaggcttc atctgggcct gtaaaaacta tgatggtgac gtgcagtcgg actctgtggc    1140
ccaagggtat ggctctctcg gcatgatgac cagcgtgctg gtttgtccag atggcaagac    1200
agtagaagca gaggctgccc acgggactgt aaccgtcac taccgcatgt accagaaagg    1260
acaggagacg tccaccaatc ccattgcttc catttttgcc tggaccagag ggttagccca    1320
cagagcaaag cttgataaca ataaagagct tgccttcttt gcaaatgctt tggaagaagt    1380
ctctattgag acaattgagg ctggcttcat gaccaaggac ttggctgctt gcattaaagg    1440
tttacccaat gtgcaacgtt ctgactactt gaatacattt gagttcatgg ataaacttgg    1500
agaaaacttg aagatcaaac tagctcaggc caaactttaa gttcatacct gagctaagaa    1560
ggataattgt cttttggtaa ctaggtctac aggtttacat ttttctgtgt tacactcaag    1620
gataaaggca aaatcaattt tgtaatttgt ttagaagcca gagtttatct tttctataag    1680
tttacagcct ttttcttata tatacagtta ttgccacctt tgtgaacatg gcaagggact    1740 ttttttacaat ttttattta ttttctagta ccagcctagg aattcggtta gtactcattt    1800
gtattcactg tcactttttc tcatgttcta attataaatg accaaaatca agattgctca    1860
aaagggtaaa tgatagccac agtattgctc cctaaaatat gcataagta gaaattcact    1920 gccttcccct cctgtccatg accttgggca cagggaagtt ctggtgtcat agatatcccg    1980
ttttgtgagg tagagctgtg cattaaactt gcacatgact ggaacgaagt atgagtgcaa    2040
ctcaaatgtg ttgaagatac tgcagtcatt tttgtaaaga ccttgctgaa tgtttccaat    2100
```

```
agactaaaata ctgtttaggc cgcaggagag tttggaatcc ggaataaata ctacctggag    2160
gtttgtcctc tccattttc tctttctcct cctggcctgg cctgaatatt atactactct     2220
aaatagcata tttcatccaa gtgcaataat gtaagctgaa tcttttttgg acttctgctg    2280
gcctgtttta tttcttttat ataaatgtga tttctcagaa attgatatta aacactatct    2340
tatcttctcc tgaactgttg attttaatta aaattaagtg ctaattacca ttaaaaaaaa    2400

<210> SEQ ID NO 2
<211> LENGTH: 1578
<212> TYPE: DNA
<213> ORGANISM: Homo sapiens

<400> SEQUENCE: 2
attttgcaac gccataggct tccagcgact gctggtgatg tttctgatgc cgacaaaagg      60
atcaaggtgg cgaagcccgt ggtggagatg gatggtgatg agatgacccg tattatctgg     120
cagttcatca aggagaagct catcctgccc cacgtggaca tccagctaaa gtattttgac     180
ctcgggctcc caaaccgtga ccagactgat gaccaggtca ccattgactc tgcactggcc     240
acccagaagt acagtgtggc tgtcaagtgt gccaccatca ccctgatga ggcccgtgtg       300 gaagagttca gctgaagaa gatgtggaaa gtcccaatg gaactatccg gaacatcctg        360 gggggactg tcttccggga gcccatcatc tgcaaaaaca tcccacgcct agtccctggc       420
tggaccaagc ccatcaccat tggcaggcac gcccatggcg accagtacaa ggccacagac       480
tttgtggcag accgggccgg cactttcaaa atggtcttca ccccaaaaga tggcagtggt       540
gtcaaggagt gggaagtgta caacttcccc gcaggcggcg tgggcatggg catgtacaac       600
accgacgagt ccatctcagg tttgcgcac agctgcttcc agtatgccat ccagaagaaa       660
tggccgctgt acatgagcac caagaacacc atactgaaag cctacgatgg gcgtttcaag       720
gacatcttcc aggagatctt tgacaagcac tataagaccg acttcgacaa gaataagatc       780
tggtatgagc accggctcat tgatgacatg gtggctcagg tcctcaagtc ttcgggtggc       840
tttgtgtggg cctgcaagaa ctatgacgga gatgtgcagt cagacatcct ggcccagggc       900
tttggctccc ttggcctgat gacgtccgtc ctggtctgcc ctgatgggaa gacgattgag       960
gctgaggccg ctcatgggac cgtcacccgc cactatcggg agcaccagaa gggccggccc      1020
accagcacca accccatcgc cagcatcttt gcctggacac gtggcctgga gcaccggggg      1080
aagctggatg ggaaccaaga cctcatcagg tttgcccaga tgctggagaa ggtgtgcgtg      1140
gagacggtgg agagtggagc catgaccaag gacctggcgg gctgcattca cggcctcagc      1200
aatgtgaagc tgaacgagca cttcctgaac accacggact tcctcgacac catcaagagc      1260
aacctggaca gagccctggg caggcagtag ggggaggcgc cacccatggc tgcagtggag      1320
gggccagggc tgagccggcg ggtcctcctg agcgcggcag agggtgagcc tcacagcccc      1380
tctctggagg cctttctagg ggatgttttt ttataagcca gatgttttta aaagcatatg      1440
tgtgtttccc ctcatggtga cgtgaggcag gagcagtgcg ttttacctca gccagtcagt      1500
atgttttgca tactgtaatt tatattgccc ttggaacaca tggtgccata tttagctact      1560
aaaaagctct tcacaaaa                                                     1578
```

RETINOID COMPOSITIONS AND METHODS OF INCREASING IMMUNE CELL-MEDIATED KILLING OF IDH MUTANT CANCER CELLS

BACKGROUND OF THE INVENTION

1) Field of the Invention

The fields of the invention are immunology and cancer therapy.

2) Description of Related Art

A glioma is a tumor or cancer in the brain or spine. Malignant gliomas are the most common primary brain tumors in adults. Many gliomas are associated with mutations in isocitrate dehydrogenase (IDH) genes/proteins. The IDH family comprises three isozymes: IDH1, located in the cytosol and peroxisome, and IDH2 and IDH3, both located in the mitochondria. IDH1 and IDH2 are obligate homodimers and utilize nicotinamide adenine dinucleotide phosphate ($NADP^+$) as a co-factor. The nicotinamide adenine dinucleotide ($NAD^+$)-dependent IDH3 isozyme exists as a heterotetramer consisting of two alpha, one beta and one gamma subunit and plays a central role in the tricarboxylic acid (TCA) cycle, the final major metabolic pathway of cellular aerobic respiration.

Mutations in IDH1 and IDH2 are present in over 70% of grade II-III gliomas and secondary glioblastomas. Chesnelong, *Next Generation Sequencing in Cancer Research*, 2:441-458 (2015). IDH1 mutation is much more frequent than IDH2 mutation in gliomas. Id. The most common IDH mutations affect residue R132 (IDH1), its analogous residue R172 (IDH2) and the non-analogous R140 (IDH2). Id. Several IDH1 R132 variants have been identified: R132H, R132C, R132G, R132S, and R132L. Id. R132H is the most common of those variants (approximately 90% in gliomas, 50% in AML). Three IDH2 R140 variants have been identified: R140Q, R140L, and R140W. Id. Different IDH2 R172 variants have also been detected with R172K representing the large majority of cases. Id. Notably, IDH1 and IDH2 mutations are mutually exclusive and strictly heterozygous. Id.

Both IDH1 and IDH2 catalyze the oxidative decarboxylation of isocitrate to alpha-ketoglutarate ($\alpha$-KG), an important Kreb's cycle metabolite. Notably, $\alpha$-KG is required for the enzymatic function of $\alpha$-KG-dependent dioxygenases, a significant proportion of which are histone and DNA demethylating enzymes. Thus, $\alpha$-KG links cellular metabolism to regulation of the epigenome and maintenance of the cellular differentiation state.

Mutations in isocitrate dehydrogenase 1 and 2 (IDH1 and IDH2) can be genetic drivers of human cancer. For example, mutant IDH1 and IDH2 proteins acquire neomorphic enzymatic function that enables the conversion of $\alpha$-KG to the oncometabolite (R)-2-hydroxyglutarate (2-HG). 2-HG ostensibly mediates its oncogenic potential in part by inhibiting the function of $\alpha$-KG-dependent demethylases, resulting in significant histone and DNA hypermethylation.

In gliomas, hypermethylation results in a methylation signature known as the glioma CpG island methylation phenotype (g-CIMP) and a characteristic repressive transcriptomal signature. Several studies have delineated the major genes and pathways that are selectively repressed in IDH mutant gliomas. Gliomas with IDH1/2 mutations are characterized by hypermethylation of multiple genes, including immune genes, thereby rendering them resistant to immunotherapy. Retinol binding protein 1 (RBP1) gene, which is involved in retinoic acid (RA) generation, is significantly hyper-methylated and under-expressed in IDH mutant cells.

Previous studies on genetic differences in IDH mutant gliomas have described a significant repression of immune-related genes. For instance, IDH mutant gliomas downregulate NKG2D ligands (especially ULBP3) as a central immune evasion mechanism. Differentially expressed genes in IDH mutants also indicated that several retinoic acid pathway-related genes, including Retinol binding protein 1 (RBP1), are among the most hypermethylated and transcriptionally repressed genes in IDH mutant gliomas.

RBP1 is an intracellular chaperone protein that facilitates the uptake and metabolism of Vitamin A, resulting in the biosynthesis of all-trans retinoic acid (ATRA). ATRA is a vitamin A metabolite with pleiotropic cellular functions ranging from regulation of cellular differentiation to modulation of immune responses. ATRA can induce certain NKG2D ligands such as ULBP3.

BRIEF DESCRIPTION OF THE DRAWINGS

FIG. 5(A-C) is a set of graphs and schematics showing ATRA induces gene expression in IDH mutant glioma cells.

FIG. 8(A-D) shows effects of RBP1 over-expression in IDH mutant cells.

FIG. 13(A-D) are images and graphs showing ATRA induced delayed differentiation in IDH mutant glioma cells. IDH mutant and WT glioma stem cells were treated with 1 μM ATRA for up to 14 days. At different time points (d2, d7 and d14), the cells were evaluated for changes in morphology and expression of stem cells and differentiation markers.

DETAILED DESCRIPTION OF THE INVENTION

Figure 1A:
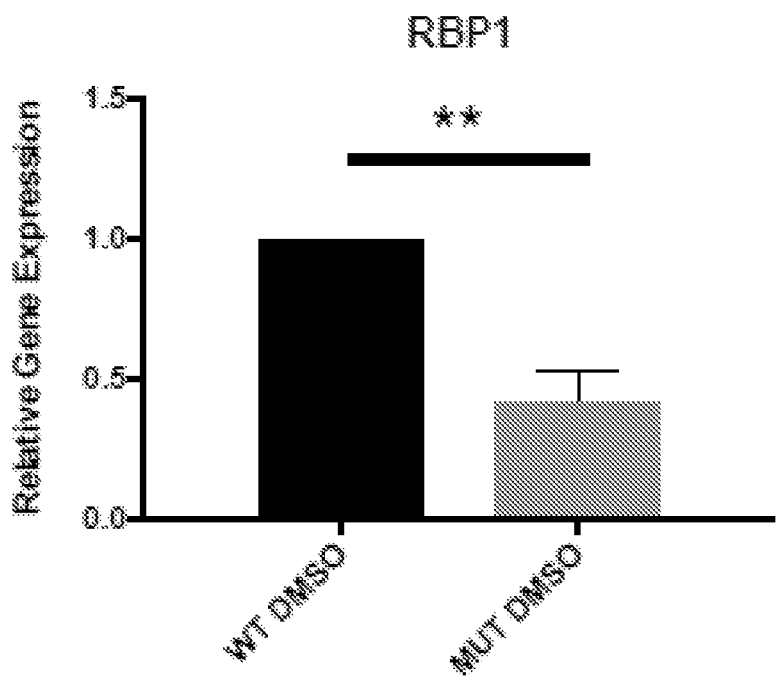
FIG. 1(A-F) are graphs showing RBP1 expression is repressed in IDH mutant gliomas. qPCR analysis of primary IDH mutant and wild type (WT) cells for several genes associated with retinoid acid pathway, including RBP1 (FIG. 1A), RBP4 (FIG. 1B), STAT1 (FIG. 1C), IRF1 (FIG. 1D), IFITM3 (FIG. 1E), and STING (FIG. 1F). Three patient-derived IDH mutant (grey bars) and wild-type cell lines (black bars) each were evaluated for gene expression. Relative gene expression is indicated +/−SD. **$p<0.01$ FIG. 2(A-G) are graphs showing ATRA mediates natural kill (NK) cell cytotoxicity in IDH mutant cells in vitro. IDH WT and mutant primary glioma cells were treated with 1 μM ATRA or DMSO for 48 hours. After treatment, cells were evaluated for NK killing and NKG2D ligand expression.
Figure 1B:
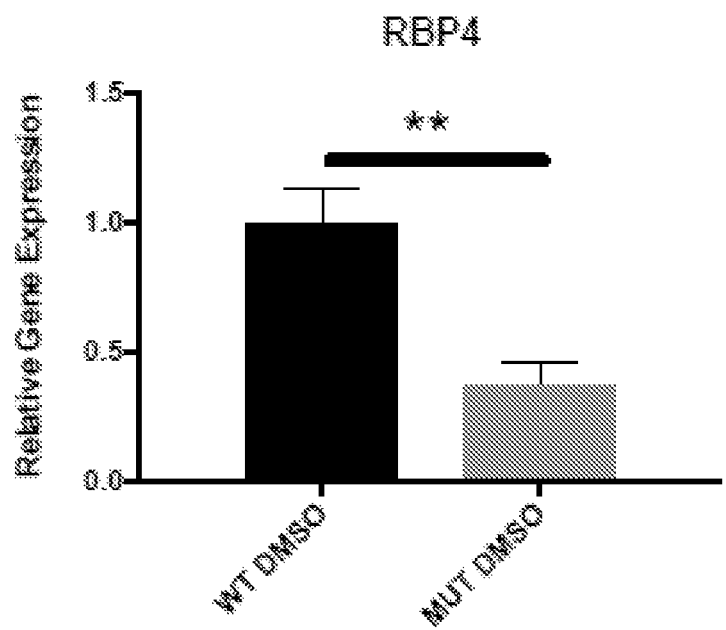
Figure 1C:
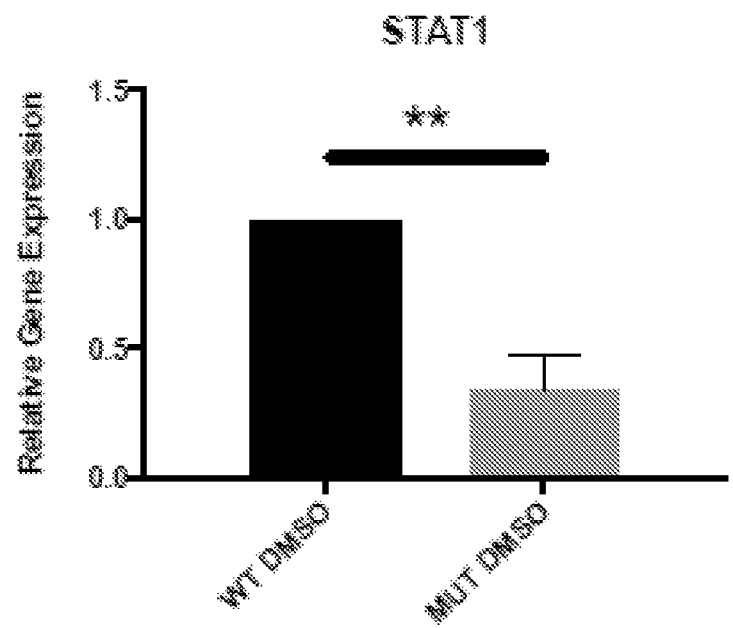
Figure 1D:
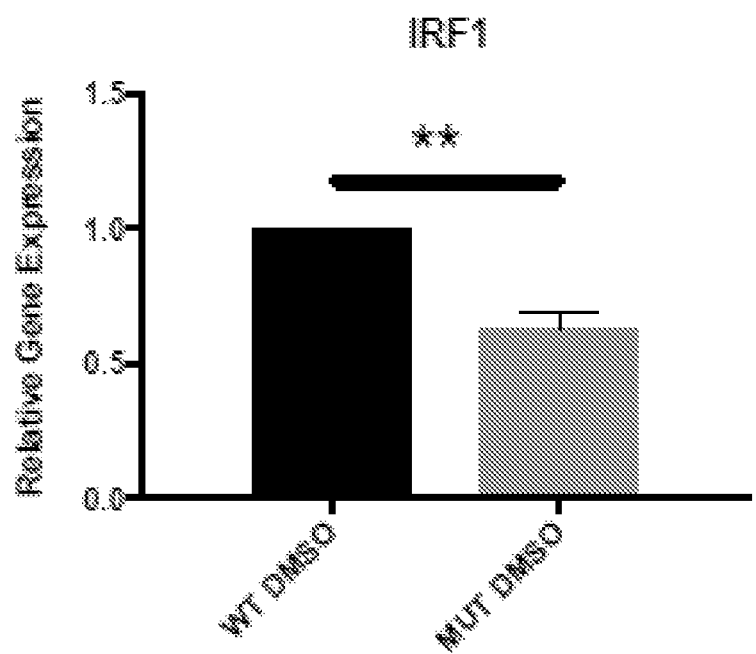
Figure 1E:
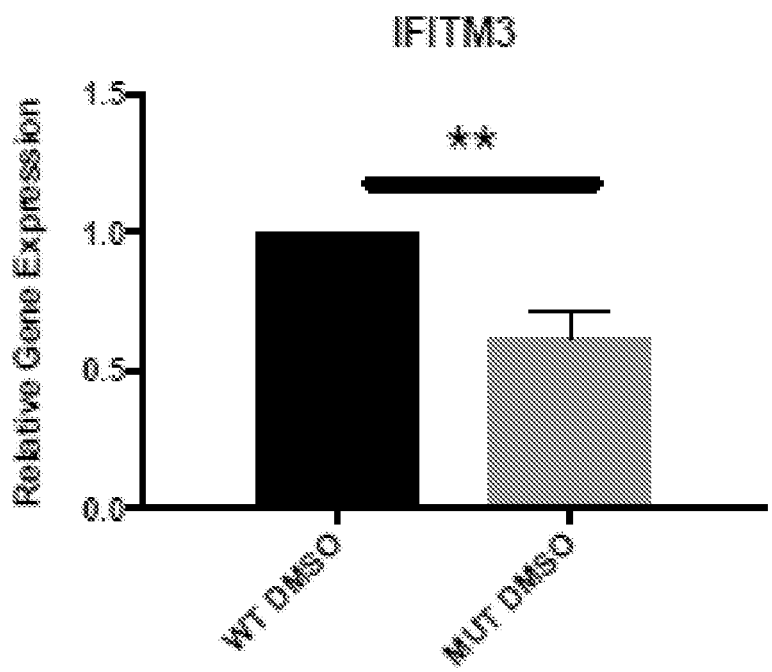
Figure 1F:
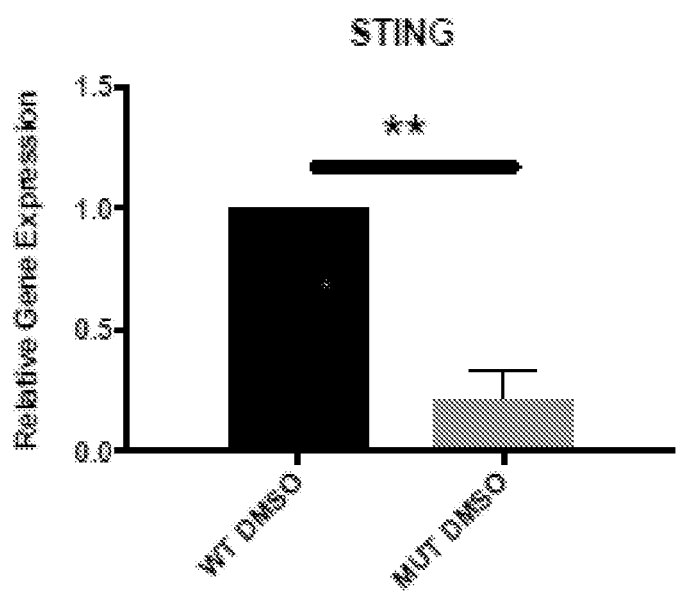

Provided herein are methods of treating an IDH mutant cancer in a subject. The methods comprise administering to the subject a therapeutically effective amount of a composition comprising an all-trans retinoic acid (ATRA) effective to increase an NK cell-mediated and/or T cell-mediated immune response to the cancer. Terms used throughout this application are to be construed with ordinary and typical meaning to those of ordinary skill in the art. However, Applicants desire that the following terms be given the particular definition as defined below.

Definitions

As used in the specification and claims, the singular form "a," "an," and "the" include plural references unless the context clearly dictates otherwise. For example, the term "a cell" includes a plurality of cells, including mixtures thereof.

The term "administering" refers to an administration that is oral, topical, intravenous, subcutaneous, transcutaneous, transdermal, intramuscular, intra joint, intra-tumor, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

The term "all-trans retinoic acid" is also referred to herein as "ATRA" and means a composition having the below chemical formula. An "ATRA composition" comprises, consists essentially of, or consists of ATRA.

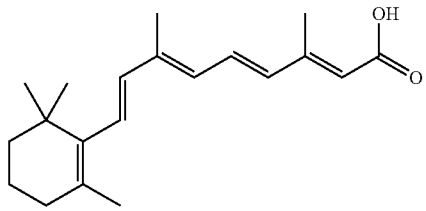 [SMILES: CC1=C(/C=C/C(C)=C/C=C/C(C)=C/C(=O)O)C(C)(C)CCC1]

The term "cancer" is used to address any neoplastic disease, and is not limited to epithelial neoplasms (surface and glandular cancers; such a squamous cancers or adenomas). The term "cancer" is used here to describe both solid tumors and hematologic malignancies, including gliomas, epithelial (surface and glandular) cancers, soft tissue and bone sarcomas, angiomas, mesothelioma, melanoma, lymphomas, leukemias and myeloma.

The term "CCL2" refers herein to a C—C motif chemokine ligand 2. CCL2 is also known as "chemokine (C—C motif) ligand 2", SCYA2, "small inducible cytokine A2 (monocyte chemotactic protein 1, homologous to mouse Sig-je)", GDCF-2, HC11, MCAF, MCP-1, MCP1, MGC9434, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2", and SMC-CF. In some embodiments, the CCL2 polypeptide or polynucleotide is that identified in one or more publicly available databases as follows: HGNC: 10618 Entrez Gene: 6347 Ensembl: ENSG00000108691 OMIM: 158105 UniProtKB: P13500.

The term "CXCL2" refers herein to a C—X—C motif chemokine ligand 2. CXCL2 is also known as chemokine (C—X—C motif) ligand 2, GRO2, GRO2 oncogene, CINC-2a, GROb, MGSA-b, MIP-2a, and SCYB2. In some embodiments, the CXCL2 polypeptide or polynucleotide is that identified in one or more publicly available databases as follows: HGNC: 4603 Entrez Gene: 2920 Ensembl: ENSG00000081041 OMIM: 139110 UniProtKB: P19875.

The term "CXCL12" refers herein to a C—X—C motif chemokine ligand 12. CXCL12 is also known as chemokine (C—X—C motif) ligand 12, SDF1, SDF1A, SDF1B, stromal cell-derived factor 1, PBSF, SCYB12, SDF-1a, SDF-1b, TLSF-a, TLSF-b, and TPAR1. In some embodiments, the CXCL12 polypeptide or polynucleotide is that identified in one or more publicly available databases as follows: HGNC: 10672 Entrez Gene: 6387 Ensembl: ENSG00000107562 OMIM: 600835 UniProtKB: P48061. The terms "CXCL12.1" (also known as CXCL12a) and "CXCL12.2" (CXCL12b) refer to two isoforms of CXCL12 produced by alternate splicing.

The terms "cell," "cell line," and "cell culture" include progeny. It is also understood that all progeny may not be precisely identical in DNA content, due to deliberate or inadvertent mutations.

A "composition" is intended to include a combination of active agent or agents (for example, one or more retinoic acid agents) and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative." Various controls within the scope of the present invention are described in more detail below.

An "effective amount" is an amount sufficient to effect beneficial or desired results. An effective amount can be administered in one or more administrations, applications or dosages.

As used herein, "gene expression" and "protein expression" refer to the process by which polynucleotides are transcribed into mRNA and the process by which the transcribed mRNA is subsequently being translated into peptides, polypeptides, or proteins, respectively. If the polynucleotide is derived from genomic DNA, expression may include splicing of the mRNA in a eukaryotic cell. "Gene overexpression" refers to the overproduction of the mRNA transcribed from the gene, at a level that is about 2.5 times higher, about 5 times higher, or about 10 times higher than the expression level detected in a control sample. "Protein overexpression" includes the overproduction of the protein product encoded by a gene at a level that is about 2.5 times higher, about 5 times higher, or about 10 times higher than the expression level detected in a control sample.

The term "identity" or "homology" shall be construed to mean the percentage of nucleotide bases or amino acid residues in the candidate sequence that are identical with the bases or residues of a corresponding sequence to which it is compared, after aligning the sequences and introducing gaps, if necessary to achieve the maximum percent identity for the entire sequence, and not considering any conservative substitutions as part of the sequence identity. Neither N- nor C-terminal extensions nor insertions shall be construed as reducing identity or homology. A polynucleotide or polynucleotide region (or a polypeptide or polypeptide region) that has a certain percentage (for example, about 80%, about 85%, about 90%, or about 95%) of "sequence homology" to another sequence means that, when aligned, that percentage of bases (or amino acids) are the same in comparing the two sequences. This alignment and the percent homology or sequence identity can be determined using software programs known in the art. In one embodiment, default parameters are used for alignment. In one embodiment a BLAST program is used with default parameters. In one embodiment, BLAST programs BLASTN and BLASTP are used with the following default parameters: Genetic code=standard; filter=none; strand=both; cutoff=60, expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

The term "IDH" refers herein to an NADP+-dependent isocitrate dehydrogenase polypeptide that in humans is encoded by one of an IDH1 and IDH2 gene. In some embodiments, the IDH1 polypeptide or polynucleotide is that identified in one or more publicly available databases as follows: HGNC: 5382, Entrez Gene: 3417, Ensembl: ENSG00000138413, OMIM: 147700 or UniProtKB: O75874. In some embodiments, the IDH1 polynucleotide comprises the sequence of SEQ ID NO:1, or a polynucleotide sequence having at or greater than about 80%, at or greater than about 85%, at or greater than about 90%, at or greater than about 95%, or at or greater than about 98% homology with SEQ ID NO:1, or a polynucleotide comprising a portion of SEQ ID NO:1. In some embodiments, the IDH2 polypeptide or polynucleotide is that identified in one or more publicly available databases as follows: HGNC: 5383, Entrez Gene: 3418, Ensembl: ENSG00000182054, OMIM: 147650, UniProtKB: P48735. In some embodiments, the IDH2 polynucleotide comprises the sequence of SEQ ID NO:2, or a polynucleotide sequence having at or greater than about 80%, at or greater than about 85%, at or greater than about 90%, at or greater than about 95%, or at or greater than about 98% homology with SEQ ID NO:2, or a polynucleotide comprising a portion of SEQ ID NO:2.

The term "IDH mutation" refers to a difference in an IDH polynucleotide or polypeptide as compared to a corresponding IDH wild type polynucleotide or polypeptide, which difference in sequence affects the function of the IDH polypeptide. In some embodiments, an IDH mutation increases production of 2-hydroxyglutarate (2-HG) as associated with IDH's oxidative decarboxylation of isocitrate. An IDH mutation can, in some embodiments, include a mutation in IDH1, IDH2, or combinations thereof. In some embodiments, an IDH1 mutation occurs at amino acid 132 and/or a corresponding polynucleotide. In other or further embodiments, an IDH2 mutation occurs at amino acid 172 and/or a corresponding polynucleotide. Other IDH mutations encompassed by the term "IDH mutation" are: IDH1 R132 variants R132H, R132C, R132G, R132S, and R132L; IDH2 R140 variants R140Q, R140L, and R140W; and IDH2 R172 variant R172K.

The term "IDH mutant cancer" refers to a cancer identified as being caused by or associated with an IDH mutation. In some embodiments, the IDH mutant cancer is a glioma, an acute myeloid leukemia (AML), a myelodysplastic syndrome (MDS), a myeloproliferative neoplasms (MPN), a cholangiocarcinoma, a chondrosarcoma, a cholangiosarcoma, a breast cancer or a skin cancer. In some embodiments, the IDH mutant cancer is a glioma. In some embodiments, the glioma is an adult grade II or III glioma. In some embodiments, the IDH mutant cancer is an astrocytoma, an oligodendroglioma or glioblastoma. In some embodiments, the astrocytoma is a grade II or III astrocytoma. In some embodiments, the glioblastoma is a secondary glioblastoma or a glioblastoma multiforme. In some embodiments, the IDH mutant cancer is a chondrosarcoma.

The term "IFITM3" refers herein to an interferon induced transmembrane protein 3. IFITM3 is also known as 1-8U, dispanin subfamily A member 2b, and DSPA2b. In some embodiments, the IFITM3 polypeptide or polynucleotide is that identified in one or more publicly available databases as follows: HGNC: 5414 Entrez Gene: 10410 Ensembl: ENSG00000142089 OMIM: 605579 UniProtKB: Q01628.

The term "IRF1" refers herein to an interferon regulatory factor 1. IRF1 is also known as MAR. In some embodiments, the IRF1 polypeptide or polynucleotide is that identified in one or more publicly available databases as follows: HGNC: 6116 Entrez Gene: 3659 Ensembl: ENSG00000125347 OMIM: 147575 UniProtKB: P10914.

"Mammal" for purposes of treatment refers to any animal classified as a mammal, including human, domestic and farm animals, nonhuman primates, and zoo, sports, or pet animals, such as dogs, horses, cats, cows, etc.

The term "MICA" refers to a ligand for the NKG2-D type II integral membrane protein receptor that is also known as MHC Class I Polypeptide-Related Sequence A. In some embodiments, the MICA polypeptide or polynucleotide is that identified in one or more publicly available databases as follows: HGNC: 7090, Entrez Gene: 100507436, Ensembl: ENSG00000204520, OMIM: 600169, and UniProtKB: Q29983.

The term "MICB" refers to a heavily glycosylated protein which is a ligand for the NKG2D type II receptor that is also known as MHC Class I Polypeptide-Related Sequence B. In some embodiments, the MICB polypeptide or polynucleotide is that identified in one or more publicly available databases as follows: HGNC: 7091, Entrez Gene: 4277, Ensembl: ENSG00000204516, OMIM: 602436, and UniProtKB: Q29980.

As used herein, the terms "neoplastic cells," "neoplasia," "tumor cells," "tumor," "cancer," and "cancer cells" (used interchangeably) refer to cells which exhibit relatively autonomous growth, so that they exhibit an aberrant growth phenotype characterized by a significant loss of control of cell proliferation (i.e., de-regulated cell division). Tumor cells can be malignant or benign. A metastatic cell or tissue means that the cell can invade and destroy neighboring body structures.

The term "NK cell" refers herein to a natural killer cell. Known human NK cell surface markers are CD16 (FcγRIII) and CD56.

The term "NKG2D" refers herein to a transmembrane protein characterized by a type II membrane orientation (has an extracellular C terminus) and the presence of a C-type lectin domain. NKG2D binds to a diverse family of ligands that include MHC class I chain-related A and B proteins and UL-16 binding proteins. NKG2D is also known as KLRK1. In some embodiments, the NKG2D polypeptide or polynucleotide is that identified in one or more publicly available databases as follows: HGNC: 18788, Entrez Gene: 22914, Ensembl: ENSG00000213809, OMIM: 611817, and UniProtKB: P26718.

A "pharmaceutical composition" is intended to include the combination of an active agent with a pharmaceutically acceptable carrier, inert or active, making the composition suitable for diagnostic or therapeutic use in vivo or ex vivo.

The term "pharmaceutically acceptable carrier" means a carrier or excipient that is useful in preparing a pharmaceutical composition that is generally safe and non-toxic, and includes a carrier that is acceptable for veterinary and/or human pharmaceutical use. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below. The pharmaceutical compositions also can include preservatives. A "pharmaceutically acceptable carrier" as used in the specification and claims includes both one and more than one such carrier.

The terms "pharmaceutically effective amount," "therapeutically effective amount," and "therapeutically effective dose" refer to the amount of a composition such as an ATRA composition that will elicit the biological or medical response of a tissue, system, animal, or human that is being sought by the researcher, veterinarian, medical doctor or other clinician. In some embodiments, a desired response is a treatment of a cancer. In some embodiments, a desired response is an NK-cell mediated treatment of cancer. As used herein, a "therapeutically effect amount for an NK-cell mediated treatment of cancer" refers to an amount of ATRA that is sufficient to upregulate NK cell ligands on tumor or cancer cells, to increase production of NK and/or T cell chemotaxis cytokines by the tumor or cancer cells, and/or to increase NK-cell mediated killing of tumor or cancer cells.

In some instances, a desired biological or medical response is achieved following administration of multiple dosages of the composition to the subject over a period of days, weeks, or years. The terms "pharmaceutically effective amount," "therapeutically effective amount," and "therapeutically effective dose" include that amount of a composition such as an ATRA composition that, when administered, is sufficient to prevent development of, or alleviate to some extent, one or more of the symptoms of the condition or disorder being treated. The therapeutically effective amount will vary depending on the composition, such as the ATRA composition, the disorder or conditions and its severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of an ATRA composition includes an amount that is sufficient to prevent development of, suppress the growth of, or reduce the numbers of, one or more cancers or tumors.

The terms "prevent," "preventing," "prevention," and grammatical variations thereof as used herein, refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

The term "RBP1" refers herein to a retinol binding protein 1. RBP1 is also known as CRABP-1, CRBP, CRBP1, CRBPI, and RBPC. In some embodiments, the RBP1 polypeptide or polynucleotide is that identified in one or more publicly available databases as follows: HGNC: 9919 Entrez Gene: 5947 Ensembl: ENSG00000114115 OMIM: 180260 UniProtKB: P09455.

The term "RBP4" refers herein to a retinol binding protein 4. In some embodiments, the RBP4 polypeptide or polynucleotide is that identified in one or more publicly available databases as follows: HGNC: 9922 Entrez Gene: 5950 Ensembl: ENSG00000138207 OMIM: 180250 UniProtKB: P02753.

The term "STAT1" refers herein to a signal transducer and activator of transcription 1. STAT1 is also known as ISGF-3, STAT91, and transcription factor ISGF-3 components p91/p84. In some embodiments, the STAT1 polypeptide or polynucleotide is that identified in one or more publicly available databases as follows: HGNC: 11362 Entrez Gene: 6772 Ensembl: ENSG00000115415 OMIM: 600555 UniProtKB: P42224.

The term "STING" refers herein to a transmembrane protein 173. STING is also known as TMEM173, ERIS, FLJ38577, MITA, MPYS, NET23, and stimulator of interferon genes. In some embodiments, the STING polypeptide or polynucleotide is that identified in one or more publicly available databases as follows: HGNC: 27962 Entrez Gene: 340061 Ensembl: ENSG00000184584 OMIM: 612374 UniProtKB: Q86WV6.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

To "suppress" tumor growth indicates a curtailment of growth state when compared to growth without contact with an ATRA composition described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

The term "tumor microenvironment" refers to the spatial (e.g., extracellular) and cellular environment surrounding a tumor and includes the tumorous or malignant cells. The tumor microenvironment comprises, for example, surrounding vasculature, immune cells (e.g., bone marrow-derived inflammatory cells, lymphocytes, macrophages), fibroblasts, signaling molecules, extracellular matrix material, and other such components. The tumor microenvironment and the tumor cells therein can affect each other. For instance, tumor cells can release factors stimulating angiogenesis in the tumor microenvironment, while immune cells can counter growth or evolution of tumor cells. By contrast, the term is distinguished from "tumor" (and "neoplasm") in that a tumor is a collection of cells having abnormal (e.g., benign or malignant) growth without respect to the microenvironment around it.

The terms "treat," "treating," "treatment" and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. In some instances, the terms "treat," "treating," "treatment" and grammatical variations thereof, include partially or completely reducing the size of a solid tumor or reducing the number of solid tumors as compared with prior to treatment of the subject or as compared with the incidence of such symptom in a general or study population.

The term "tumor microenvironment" refers to the immediate cellular environment in which a tumor exists, comprising tumor cells, cells of haematopoietic origin, cells of mesenchymal origin, and extracellular matrix.

The term "ULBP1" refers to a polypeptide ligand of natural killer group 2, member D (NKG2D). In some embodiments, the ULBP1 polypeptide or polynucleotide is that identified in one or more publicly available databases as follows: HGNC: 14893, Entrez Gene: 80329, Ensembl: ENSG00000111981, OMIM: 605697, and UniProtKB: Q9BZM6.

The term "ULBP2" refers to a polypeptide ligand of natural killer group 2, member D (NKG2D). In some embodiments, the ULBP2 polypeptide or polynucleotide is that identified in one or more publicly available databases as follows: HGNC: 14894, Entrez Gene: 80328, Ensembl: ENSG00000131015, OMIM: 605698, and UniProtKB: Q9BZM5.

The term "ULBP3" refers to a polypeptide ligand of natural killer group 2, member D (NKG2D). In some embodiments, the ULBP3 polypeptide or polynucleotide is that identified in one or more publicly available databases as follows: HGNC: 14895, Entrez Gene: 79465, Ensembl: ENSG00000131019, OMIM: 605699, and UniProtKB: Q9BZM4.

Methods of Treatment

Provided herein are methods of treating an IDH mutant cancer in a subject. The methods comprise administering to the subject a therapeutically effective amount of a composition comprising an all-trans retinoic acid (ATRA), a bexarotene, or a 13-cis retinoic acid. It is a surprising finding of the present invention that ATRA, bexarotene, 13-cis retinoic acid, or combinations thereof can increase NK cell-mediated killing of IDH mutant tumor cells. It is further surprising that ATRA, bexarotene, 13-cis retinoic acid, or combinations thereof can increase expression of NK cell ligands and production of NK and T cell chemokines by IDH mutant tumor cells. Accordingly, in some embodiments, the method comprises administering ATRA, bexarotene, 13-cis retinoic acid, or combinations thereof in an amount effective to increase an NK cell-mediated immune response to the cancer. In some or further embodiments, the method comprises administering ATRA, bexarotene, 13-cis retinoic acid, or combinations thereof in an amount effective to increase a T cell-mediated immune response to the cancer.

Increased NK cell-mediated immune responses to a cancer include, but are not limited to, increased NK cell infiltration and/or expansion in the tumor microenvironment, NK cell-mediated tumor cell apoptosis and/or lysis, NK cell activation (e.g., by increased IL-12, IL-15, IL-18, IL-2, and CCL5), secretion of soluble factors such as cytokines (e.g., IFNγ and TNFα) by NK cells, secretion of NK cell ligands (e.g., NKG2D ligands), upregulation of NK cell markers, secretion of cytolytic factors such as perforin, proteases, and granzymes by NK cells, reduction in tumor size or growth, and the like.

Increased T cell-mediated immune responses to a cancer include, but are not limited to, increased T-cell infiltration and/or expansion in the tumor microenvironment, T-cell-mediated tumor cell apoptosis and/or lysis, T-cell activation (e.g., by increased costimulation of T-cell receptor and CD28; IL-2 expression), secretion of soluble factors such as cytokines by T-cells, upregulation of T-cell markers (e.g., CD69, CD71, CD25, HLA-DR) secretion of cytolytic factors such as perforin, granzymes, and granulysin or expression of FAS ligand by T-cells, reduction in tumor size or growth, and the like.

NK cell ligands upregulated by retinoids (e.g., ATRA) include, but are not limited to, NKG2D ligands. Expression of one or more NKG2D ligands can be increased within the IDH mutant tumor microenvironment and/or within the IDH tumor cells themselves. In some embodiments, the one or more NKG2D ligands is selected from the group consisting of ULBP1, ULBP3, MICA and MICB. In some embodiments, the increased expression of ULBP1, ULBP3, MICA and/or MICB by the tumor cell is at least about 5% higher, at least about 10% higher, at least about 20% higher, at least about 30% higher, at least about 40% higher, at least about 50% higher, at least about 100% higher, or at least about 500% higher than a control cell not exposed to ATRA. The term "higher" as used herein refers to either the percentage of NKG2D ligand-producing tumor cells or the mean level of NKG2D ligand production by a population of tumor cells, or both.

In other or further embodiments, administration of a retinoid (e.g., ATRA) results in an increase in chemokine production within the IDH mutant tumor microenvironment and/or within the IDH tumor cells themselves. In some embodiments, the chemokine is CCL2. In some embodiments, the increased production of CCL2 by the tumor cell is at least about 5% higher, at least about 10% higher, at least about 20% higher, at least about 30% higher, at least about 40% higher, at least about 50% higher, at least about 100% higher, or at least about 500% higher than a control cell not exposed to ATRA. The term "higher" as used herein refers to either the percentage of CCL2-producing tumor cells or the mean level of CCL2 production by a population of tumor cells, or both. Increased production of such NK cell and/or T cell chemokines may be determined and/or measured via any method known to one of ordinary skill in the art.

Changes in expression of soluble or cell-associated factors (e.g., NKG2D ligands, CCL2, etc.) can be determined by measurement of a factor of interest in a biological sample of the subject. Expression measurements are typically compared to a control (e.g., an untreated control, a biological sample obtained prior to treatment, or a general number or average that is known and not identified in the method using a sample). Measurements can be obtained on cells directly (e.g., by flow cytometry) or in a medium of the biological sample (e.g., blood, lymph), where appropriate.

Expression of factors can be determined at the transcriptional level, the translational level, or combinations thereof, and can be measured via a wide array of methods used to measure gene or polypeptide expression levels. In some embodiments, the factor of interest (e.g., NKG2D ligands, CCL2, etc.) can be measured at the gene transcription level. For example and without limitation, levels of mRNA transcripts of a factor of interest can be determined by radiation absorbance (e.g., ultraviolet light absorption at 260, 280, or 230 nm), quantification of fluorescent dye or tag emission (e.g., ethidium bromide intercalation), quantitative polymerase chain reaction (qPCR) of cDNA produced from mRNA transcripts, southern blot analysis, gene expression microarray, or other suitable methods. Increased levels of mRNA transcripts can be used to infer or estimate increased levels of polypeptide expression.

In some embodiments, expression of a factor of interest can be measured at the post-translational level. For example and without limitation, levels of a factor of interest (e.g., a polypeptide, granzyme, lysin, ligand, etc.) can be determined by radiation absorbance (e.g., ultraviolet light), bicinchoninic acid (BCA) assay, Bradford assay, biuret test, Lowry method, Coomassie-blue staining, silver-staining, functional or enzymatic assay, cell-binding or cell-activation/response assay, immunodetection and/or Western blot analysis, or other suitable methods.

In some embodiments, increased CCL2 production in the tumor or tumor microenvironment can increase immune cell recruitment, or can increase anti-tumor immune cell recruitment. In some embodiments, the immune cell recruited by CCL2 is a NK cell. In some embodiments, increased CCL2 production facilitates an increase in number of NK cells in a tumor microenvironment of the cancer.

In some embodiments of the method of treatment, the cancer is a tumor. A tumor includes a glioma, carcinoma, a sarcoma, lymphoma and leukemia. Tumors can arise in any tissue including, but not limited to, breast, head and neck, lung, airways, prostate, colon, brain, cervix, uterus, ovaries, fallopian tubes, pancreas, esophagus, stomach, gastrointestinal tract, genitourinary tract, skin, liver, kidney, bone, soft connective tissue, central and peripheral nervous system and endocrine and exocrine tissues. In some embodiments, the cancer is a glioma. In some embodiments, the cancer is an astrocytoma, an oligodendroglioma or glioblastoma. In some embodiments, the astrocytoma is a grade II or III astrocytoma. In some embodiments, the glioblastoma is a secondary glioblastoma. In some embodiments, the cancer is a chondrosarcoma. In some embodiments, the tumor is malignant. In some embodiments, the tumor is solid.

The subject of treatment according to the methods described herein may be any animal, mammal, warm-blooded mammal or human. In one embodiment, the subject of treatment is a human. The composition comprising ATRA, bexarotene, or 13-cis retinoic acid can be administered to the subject via various methods. In some embodiments, the administration is intratumoral. In some embodiments, the administration is intracranial.

Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer or precancerous condition including, but not limited to, a chronic infection. Prophylactic administration can occur for several days to years prior to the manifestation of symptoms of cancer. In some instances, the terms "treat," "treating," "treatment" and grammatical variations thereof, include partially or completely reducing the size of a tumor, reducing the number of tumors, and reducing the spread or incidence of a cancer as compared with prior to treatment of the subject or as compared with the incidence of such symptom in a general or study population.

The methods disclosed herein can provide an array of benefits when administered to a subject having an IDH mutant tumor. In some embodiments, the method increases tumor cell death in a tumor microenvironment of the cancer. In some embodiments, the method increases apoptosis of tumor cells in a tumor microenvironment of the cancer. In some embodiments, the method reduces growth of a tumor, or the size of the tumor. In some embodiments, the method reduces malignancy (metastasis) of the tumor or tumor cells. In some embodiments, the method increases infiltration into the tumor microenvironment of anti-cancer immune cells (e.g., NK cells, tumor-specific T-cells). In some embodiments, the method increases RBP1 expression in IDH mutant tumor cells.

Also included herein are methods of administering to a subject 1) a therapeutically effective amount of a composition comprising an all-trans retinoic acid (ATRA), bexarotene, or 13-cis retinoic acid, and 2) a therapeutically effective amount of NK cells and/or T cells.

Administered NK cells and/or T-cells can be from cells obtained from the subject, which are manipulated in vitro. For instance, the NK cells and/or T-cells can be stimulated, activated, and/or expanded in culture. In some embodiments, the NK cells and/or T-cells can be engineered to contain an additional polynucleotide (e.g., to express a protein of interest in the cell).

Also disclosed herein are methods to predict the likelihood a subject with a cancer will respond therapeutically to a therapy comprising administering a composition comprising an all-trans retinoic acid (ATRA), bexarotene, or 13-cis retinoic acid, the method comprising obtaining a tumor sample from the subject; and determining a presence of an IDH mutation in the tumor sample; wherein the presence of an IDH mutation indicates the subject will respond therapeutically to the therapy; and wherein an absence of an IDH mutation indicates the subject will not respond therapeutically to the therapy. In some embodiments wherein the IDH mutation is present, the methods can further comprise administering the therapy to the subject.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLE 1

Materials and Methods

Cell lines and Cell Culture. Immortalized human syngeneic astrocyte cell lines with retrovirally transduced IDH1 mutant (R132H) construct, IDH wild-type (IDHwt; also referred to herein as IDH wt, wtIDH, and IDH WT) construct and mock-transduced with a retroviral vector were obtained from Dr. Tim Chan's group (MSKCC). The cells were cultured in Dulbecco's Modified Essential Medium (DMEM) supplemented with 10% FBS, 2 mM L-glutamine, 100 U/ml penicillin, and 100 µg/ml streptomycin (Complete Medium, (CM)). All reagents were obtained from HyClone™ (GE Healthcare). The cells were maintained in a humidified incubator at 37° C. and 5% $CO_2$. Medium was replaced every 2 days and the cells were split when they were about 80% confluent. All cell lines were negative for mycoplasma infections.

Glioma cell culture. Resected tumors from Glioma patients (both IDH wt and mutant) were mechanically dissociated to form a single cell suspension. Contaminating RBCs were removed using an RBC lysis buffer (eBioscience) and cells were propagated into neural stem cells in Neurocult™ NS-A proliferation kit supplemented with 20 ng/mL Human Recombinant EGF, 10 ng/mL Human Recombinant bFGF) and 2 µg/mL Heparin Solution (Stemcell Technologies Canada Inc.). After 3 weeks in culture, neurospheres were moved to Complete Medium (CM) in order to propagate differentiation into adherent cell lines.

Mice. 6-8 week old Balb/c nude mice (CAnN.Cg-Foxn1nu/Crl) were purchased from Charles River Laboratories. Mice were injected with $10^6$ IDH WT or mutant primary glioma cells sub-cutaneously in the right flank. When the tumors were about 25 $mm^2$, ATRA treatment was started. 10 mg/Kg ATRA was administered to mice intraperitoneally (i.p.) every alternate day until termination of the experiment. DMSO-treated mice were used as controls. The mice were monitored for signs of drug toxicity such as weight-loss, lethargy, skin lesions and diarrhea. The tumors were measured every 3 days, and the mice were sacrificed when the tumors were about 400 $mm^2$. For NK depletion experiments, 6-week old B6 nude mice (B6.Cg-Foxn1nu/J) were purchased from The Jackson Laboratory. NK depletion was performed by injecting mice with 200 µg of anti-NK1.1 antibody (Biolegend) i.p. on the day ATRA treatment was started. Mice injected with 200 µg of an isotype antibody were used as controls. Mice were bled and evaluated for circulating NKs by flow cytometry.

Immunocompetent mouse model. The RCAS/tva system was used to ectopically express muIDH1 (R132H) in PDGF-driven gliomas. RCAS retroviral vectors were used to transfer genes to specific cell types in vivo that express the receptor tva to develop a pair of isogenic mouse tumor models that differ only in IDH1 mutation status. Three RCAS vectors expressing PDGF, wtIDH1-shp53, or muIDH1 (R132H)-shp53 were constructed and used in three different Ntva mouse strains. Mice were injected with RCAS-PDGF-producing DF1 cells together with either DF1 cells producing RCAS-wtIDH1-shp53 (wtIDH1) or RCAS-mutantIDH1-shp53 (muIDH1). Tumors were generated from these injections with identical genomic backgrounds, with the initiating events differing only in IDH1 mutation status. The mice were sacrificed when they showed signs of CNS pathology and the tumors were harvested.

All-trans Retinoic acid (ATRA) treatment of astrocytes and primary glioma cells. ATRA was purchased from Sigma Aldrich® and reconstituted in DMSO. ATRA was added at a 1 µM final concentration to cell culture medium for 48 hours. After treatment, the cells either lysed in Trizol™ for qPCR analysis, or were used in NK cytotoxicity assays.

RBP1 silencing and RBP1 overexpression studies. For RBP1 silencing, IDH WT glioma cells were transduced with RBP1 shRNA lentivirus (SantaCruz biotechnologies) for 18 hours. The cells were maintained in CM containing 10 µg/ml Puromycin to select for the RBP1-silenced cells. IDH WT cells transduced with a mock shRNA lentiviral vector were used as controls.

For RBP1 overexpression studies, IDH mutant glioma cells were transduced with RBP1 expressing lentiviral vectors (Origene Inc) for 3 hours. The cells were maintained in CM containing 10 µg/ml Puromycin to select for lentivirus-transduced cells. Cells transduced with a mock lentiviral vector were used as controls.

Isolation of NK cells from donor PBMCs. Peripheral blood samples were collected in preservative-free heparin tubes (10 U/mL) and were layered onto an equal volume of Ficoll-Hypaque density gradient solution (Amersham Pharmacia Biotech Ltd., Little Chalfont, UK) and centrifuged at 2250 rpm at 20° C. The mononuclear cells (PBMCs) were collected and washed twice with PBS (Hyclone™, GE Healthcare). Cell viability was determined by trypan blue exclusion and exceeded 95%. Isolated PBMCs were used for NK cell isolation using CD56 Microbeads (Miltenyi Biotec Inc.) and a MidiMACS separation column, according to the manufacturer's instructions. Purity was (>95%), as determined by FACS analysis.

Isolation of NK cells from mice. The spleen from naïve Balb/c mice was isolated and mechanically dissociated to form single-cell suspension. RBCs were lysed using a RBC lysis buffer (eBioscience). The cells were used for NK isolation using NK cell isolation kit (mouse) (Miltenyi Biotec Inc.) and a MidiMACS separation column, according to the manufacturer's instructions. Purity was (>95%), as determined by FACS analysis.

NK-92 cell culture. For some experiments, NK92 cells were used instead of donor NK cells. NK92 cells (ATCC® CRL-2407™) were obtained from ATCC. The cells were grown in Alpha Minimum Essential medium with 2 mM L-glutamine and 1.5 g/L sodium bicarbonate, 0.2 mM inositol, 0.1 mM 2-mercaptoethanol, 0.02 mM folic acid (all from Sigma Aldrich), 12.5% horse serum and fetal bovine serum (ATCC) to a final concentration of 12.5%. Fresh medium was added every 2-3 days and once a week, the cells were counted and re-suspended at a final concentration of $5 \times 10^5$ cells/mL in fresh medium.

NK cytotoxicity assay. The flow cytometric CFSE/7-AAD cytotoxicity assay was performed as previously described with slight modifications. Astrocytes or Glioma cells ($5 \times 10^5$) were labeled with 500 nM CFSE (from a 1 mM stock solution in dimethyl sulfoxide [Sigma] stored at −20° C.) in PBS for 15 min at 37° C. The cells were then washed twice in complete medium and used immediately for the cytotoxicity assay. The CFSE-labeled target cells (25,000 cells) were used at E (effector):T (target) ratios of 1:10. After 6 h incubation, the cells were stained with 0.25 µg/ml of 7-AAD and analyzed by flow cytometry.

Flow cytometry for TILs. IDH WT and mutant tumors were dissociated to form a single cell suspension (SCS). The SCS was then overlaid onto sucrose gradient (Lympholyte-M) and centrifuged at 2400 rpm for 20 minutes. Immune cells at the interphase of the 2 liquids were collected and washed once with PBS. The cells were then stained with appropriate antibodies and acquired on a BD LSR Fortessa flow cytometer. Briefly, cells were washed with PBS and stained with 1 µg antibody for 30 minutes at 4° C. After incubation, the cells were washed three times with FACS buffer (PBS+10% FBS+0.1% Na-azide), resuspended in a final volume of 200 µl of FACS buffer and run through the flow cytometer. Flow cytometry data was analyzed on the Flowjo® v9.1 software. Antibodies used for flow cytometry were as follows: CD45- PE-Cy7, NKp46-FITC, CD11b-APC-Cy7, Gr-1-APC, F4/80-eFluor450, Ly6-c-PerCP-Cy5.5 and CD11c-PE.

Quantitative Real time RT-PCR. $5 \times 10^5$ IDH mutant and WT astrocytes, as well as patient glioma cells were lyzed in Trizol and RNA was extracted from the cells using the Chloroform extraction method. cDNA was transcribed from the RNA using iScript cDNA synthesis kit (BioRad). Real-time PCR was performed on an CFX96 Touch™ Real-Time PCR Detection System (Bio-Rad) equipped with a 96-well reaction plate. Briefly, 2 µL cDNA was added to 5 µL of the 2×SYBR Green PCR mastermix (Thermo Scientific), 800 nM of each primer, and water was added to 10 µL. The thermal denaturation protocol was run at the end of the PCR to determine the number of products that were present in the reaction. Reactions were typically run in triplicates. The cycle number at which the reaction crossed an arbitrarily-placed threshold ($C_T$) was determined for each gene and the relative amount of each gene to 18 S rRNA was described using the equation $2^{-\Delta C_T}$ where $\Delta C_T = (C_{TtargetRNA} - C_{T18S rRNA})$.

Results

RBP1 and genes downstream of retinoic acid signaling are down-regulated in IDH mutant gliomas. Analysis of TCGA database shows that RBP1 is one of the most down-regulated genes in IDH mutant tumors. Pathway analysis also showed that the retinoic acid pathway was also one of the most negatively regulated pathways in IDH mutant cells. Real-time PCR analysis also showed that in primary glioma cells, IDH mutants had significantly lower expression of a variety of genes down-stream of retinoic acid signaling viz. STAT1, type 1 immune response genes and STING (FIG. 1A through 1F).

Figure 2A:
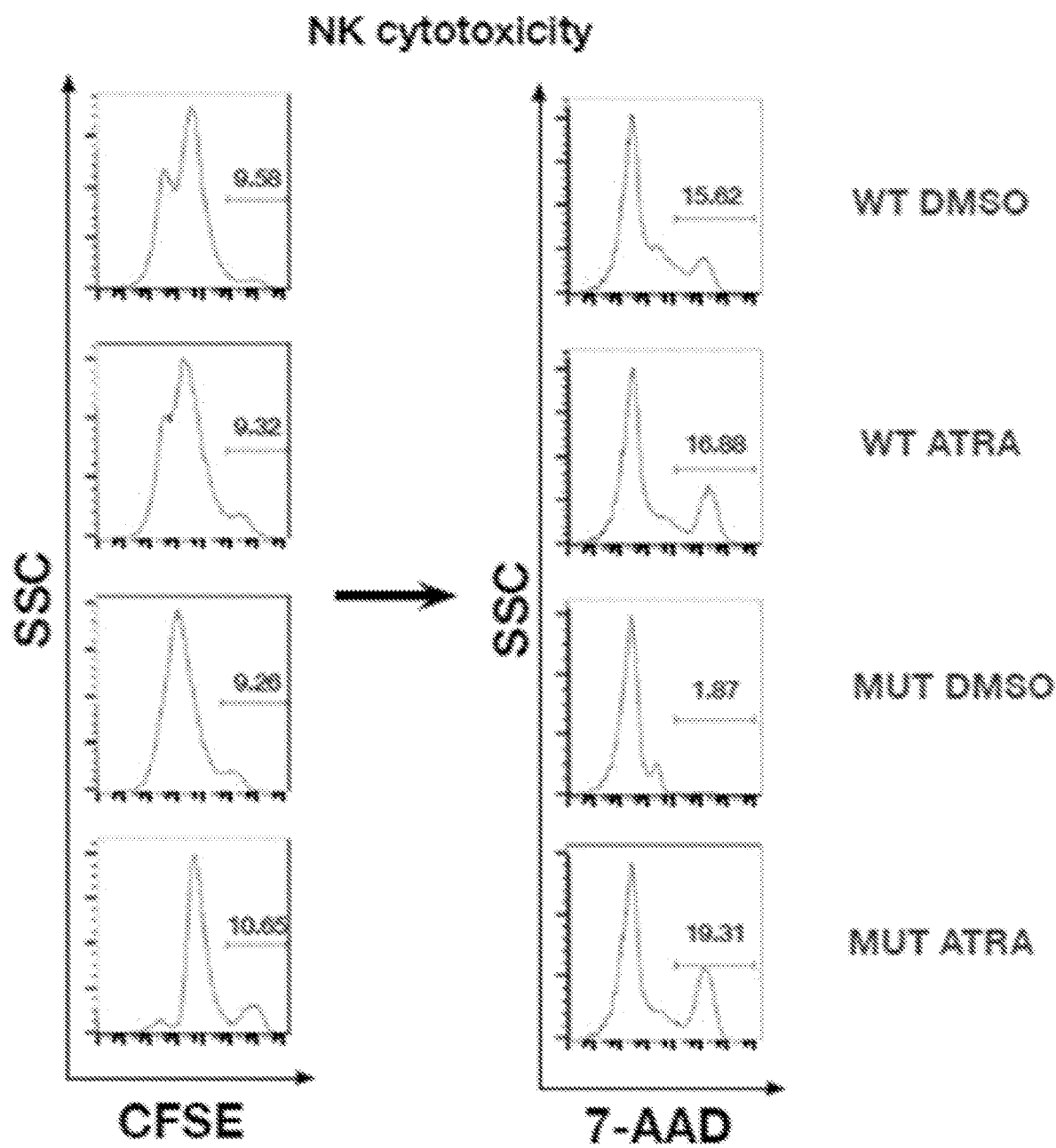
FIG. 2A shows representative flow cytometry gating strategy to assess percent cytotoxicity in tumor cells after co-culture with NKs for 6 hours at a 1:10 E (effector):T (target) ratio. The gating strategy was as follows: FSC vs. SSC->SSC vs CFSE+->SSC vs. 7-AAD+.
Figure 2B:
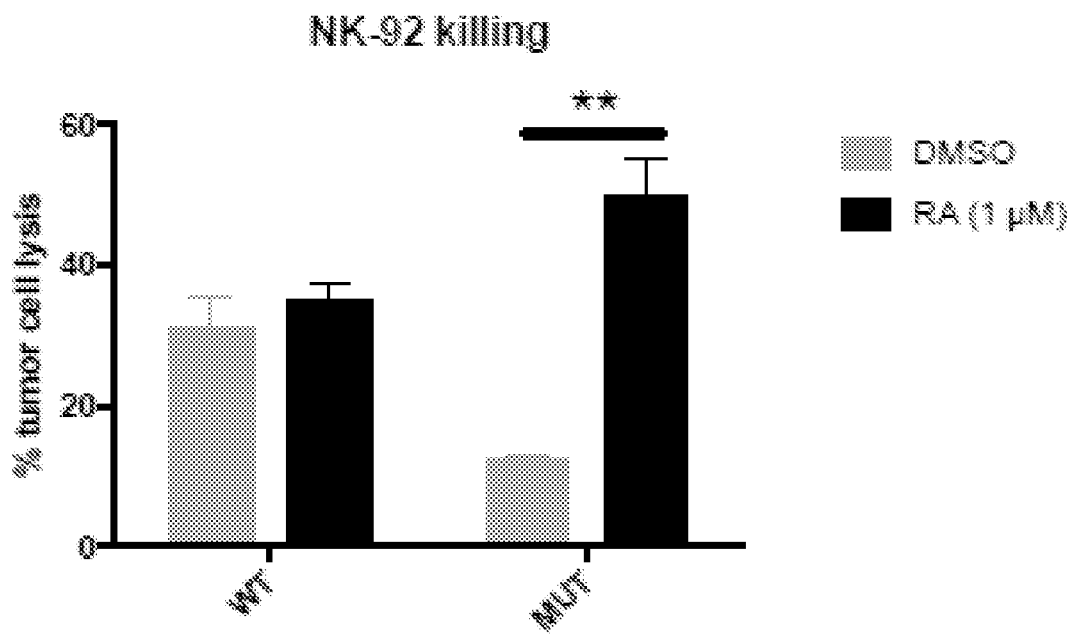
FIG. 2B is a graphical representation of the data in FIG. 2A. In some cases, after ATRA treatment, anti-NKG2D or isotype antibody (10 ug/ml) was added to the culture before co-culture with NKs.
Figure 2C:
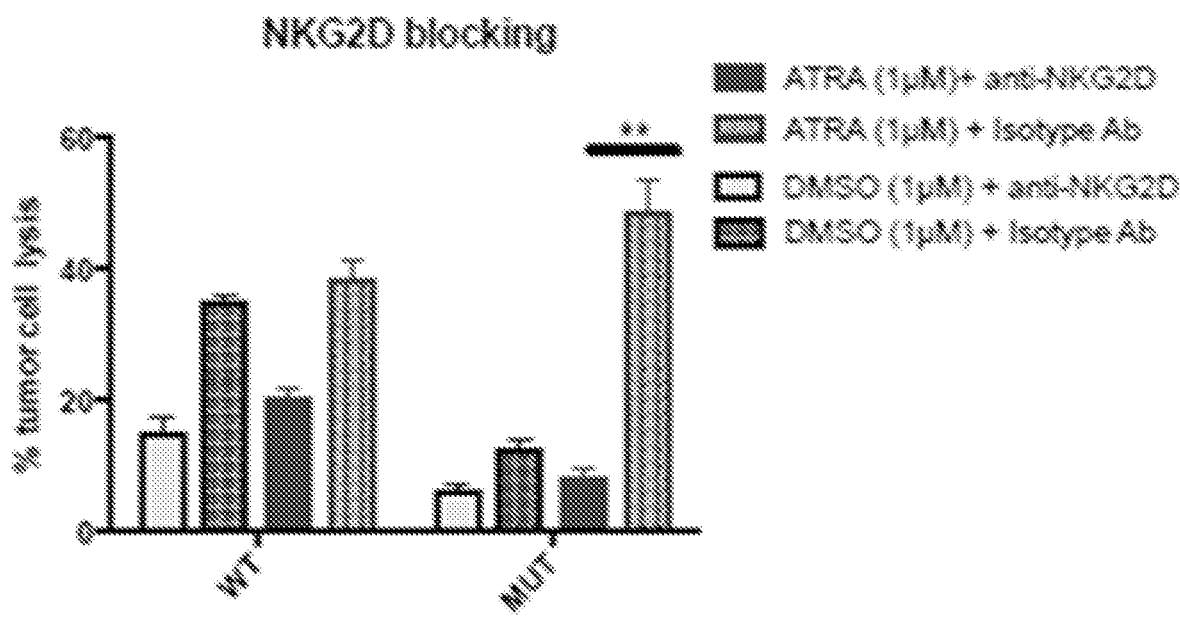
FIG. 2C is a graph showing percent cytotoxicity in the presence of NKG2D blocking antibody (solid bars) or Isotype blocking antibody (patterned bars). Gene expression analysis by qPCR for ATRA-treated and control-treated IDH WT and mutant cells are shown for the NKG2D ligands ULBP1 (FIG. 2D), ULBP3 (FIG. 2E), MICA (FIG. 2F), and MICB (FIG. 2G). Relative gene expression was established based on normalization of values to the WT DMSO group. 18s RNA expression was the reference gene. All experiments are representative of three independent experiments.
Figure 2D:
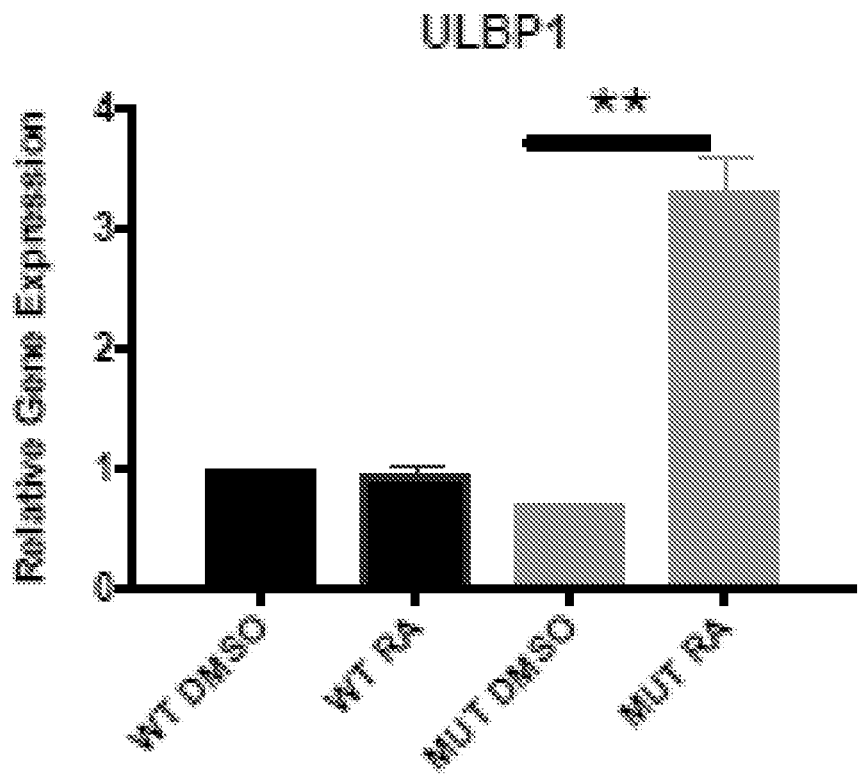
Figure 2E:
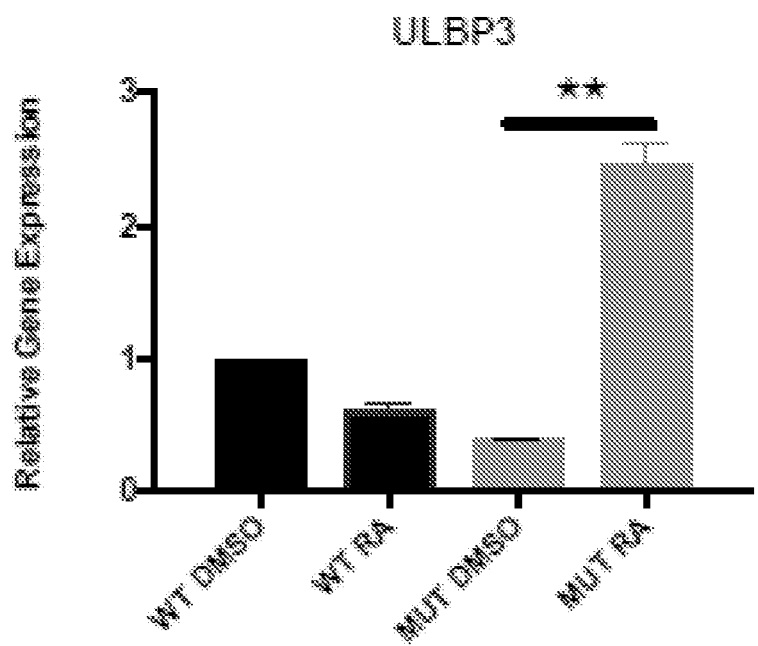
Figure 2F:
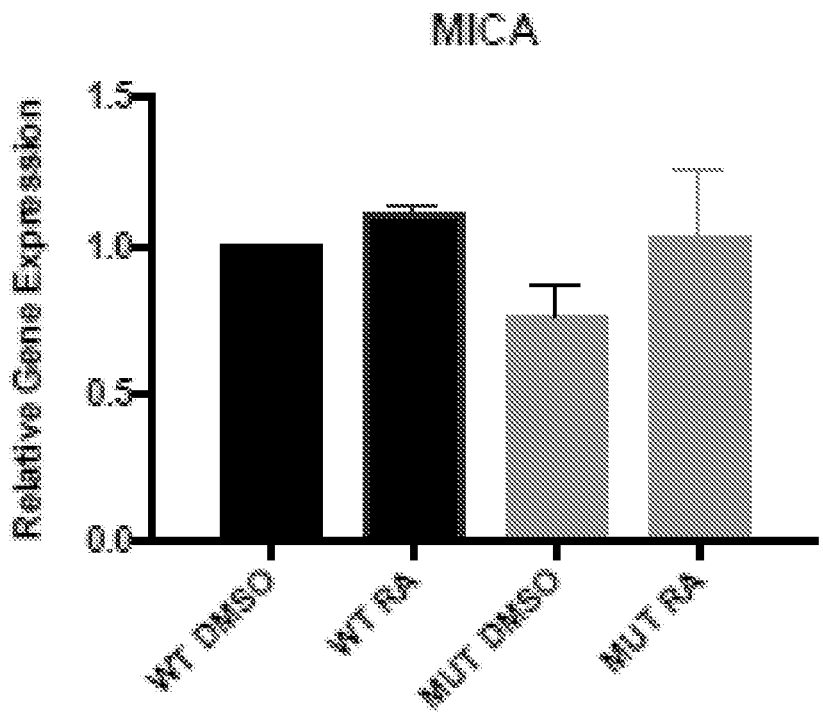
Figure 2G:
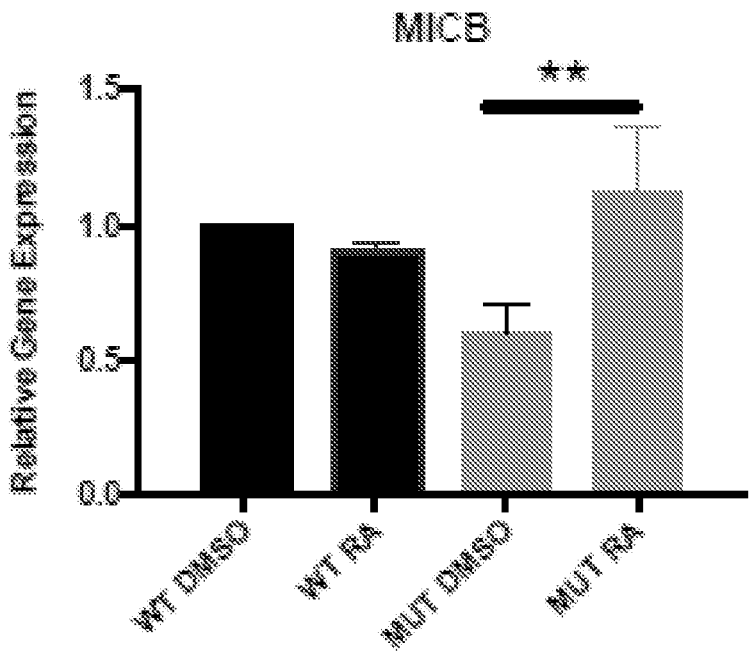

ATRA induced increased cytotoxic killing of IDH mutant cells in an NKG2D-ligand dependent manner. The ability of ATRA to sensitize IDH mutant cells to killing by NK cells was evaluated. For this purpose, IDH mutant and WT cells were treated with 1 µM ATRA for 48 hours and assessed for killing by NK-92 cells (ATCC) at a 10:1 E:T ratio. IDH mutant cells treated with ATRA were significantly more susceptible to killing by NK-92 cells, compared to DMSO-treated controls. Interestingly, ATRA treatment increased NK-92-mediated killing in IDH mutant cells to WT levels (FIGS. 2A and 2B). Also, as observed in vivo, increased NK-92 killing in IDH mutant cells was dependent upon NKG2D engagement. NK cells incubated with NKG2D blocking antibody failed to recognize and kill ATRA-treated IDH mutant cells, reducing killing to baseline levels (FIG. 2C). ATRA-treated cells were also evaluated for expression of NKG2D ligands. ATRA treatment increased expression of NKG2D ligands ULBP1 (FIG. 2D), ULBP3 (FIG. 2E), MICA (FIG. 2F), and MICB (FIG. 2G) in IDH mutant cells, as compared to DMSO-treated cells.

Figure 3A:
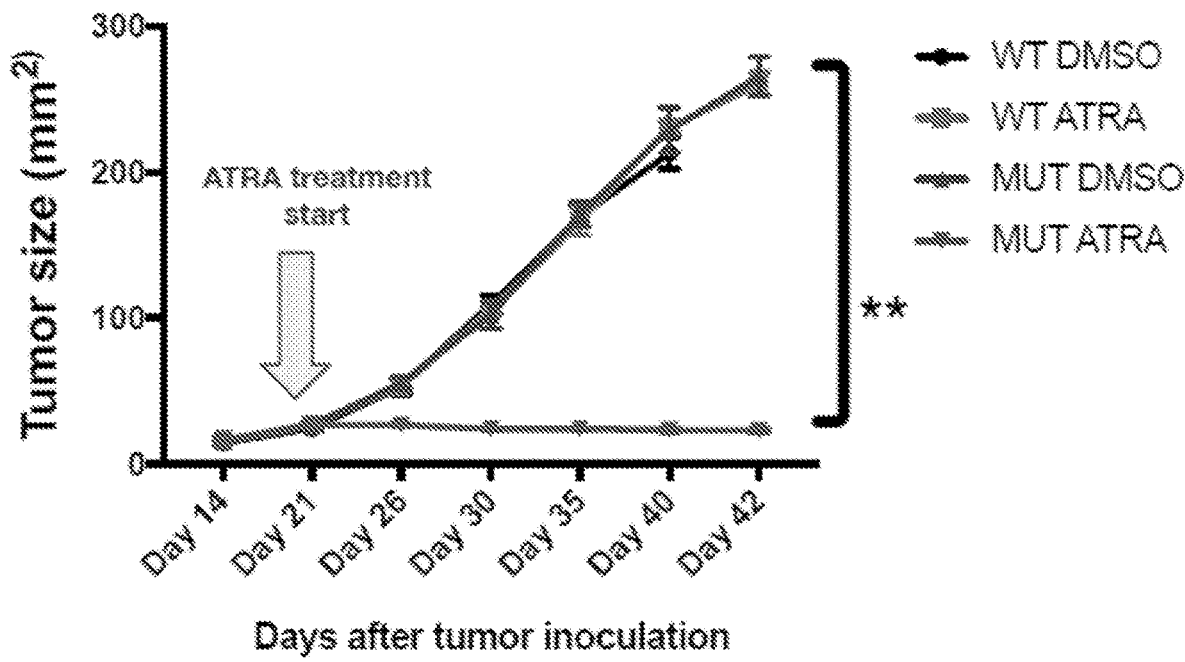
FIG. 3A is a graph showing tumor growth curves of IDH WT or mutant tumor-bearing mice treated with ATRA or DMSO. Percent 7-AAD+ tumor cells are shown after co-culture with human NKs (FIG. 3B) and mouse NKs (FIG. 3C). Immune cell infiltration in IDH WT or mutant tumors treated with ATRA or DMSO was quantified for total tumor-infiltrating lymphocytes (TILs) (FIG. 3D), macrophages (FIG. 3E), NK cells (FIG. 3F), and myeloid-derived suppressor cells (MDSCs) (FIG. 3G) **$p<0.005$. RCAS tva mice bearing IDH WT or mutant gliomas were treated with ATRA or vehicle every alternate day for 21 days. Mice bearing IDH WT gliomas (FIG. 3H) and IDH mutant gliomas (FIG. 3I) were analyzed for survival after treatment with ATRA or vehicle. Immunohistochemistry of paraffin embedded section of tumor to detect NK infiltration was performed.
Figure 3B:
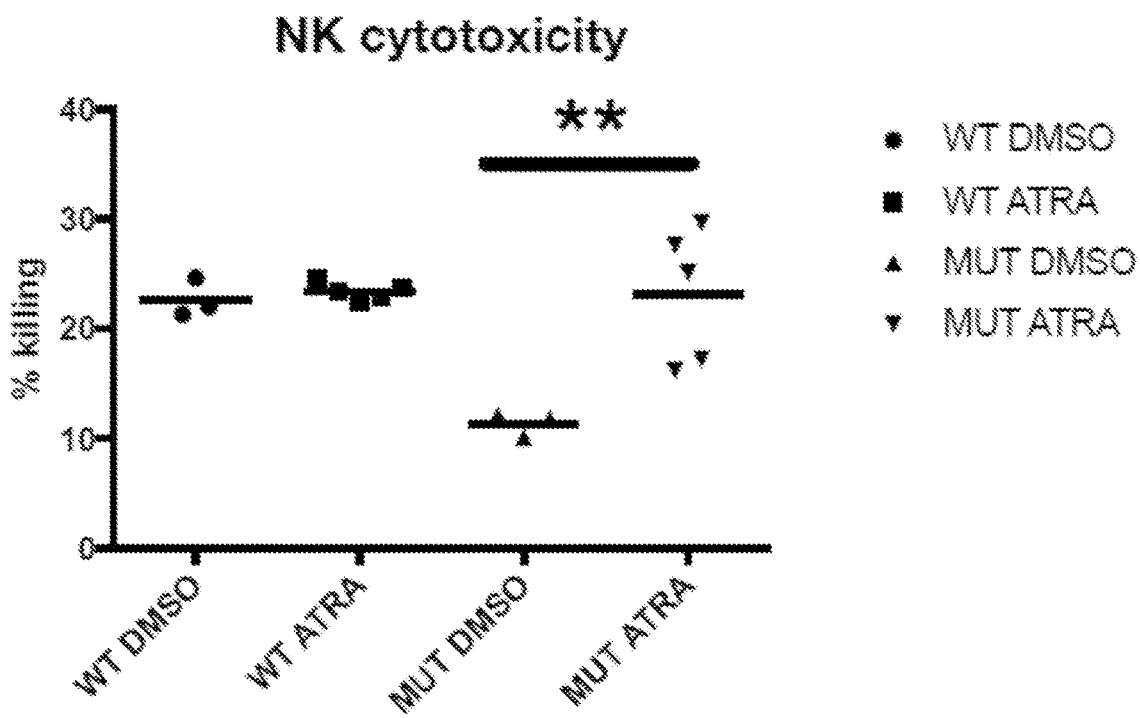
FIG. 3(A-J) are graphs and images showing ATRA induces tumor stasis in IDH mutant tumor-bearing mice in vivo.
FIG. 3J includes images representative of three independent fields of view at magnification 10× for IDH mutant gliomas treated with vehicle (upper left panel) or ATRA (upper right panel), and for IDH WT gliomas treated with vehicle (lower left panel) or ATRA (lower right panel). Nuclei were stained with DAPI (blue), while NK cells are depicted with green fluorescent stain.
Figure 3C:
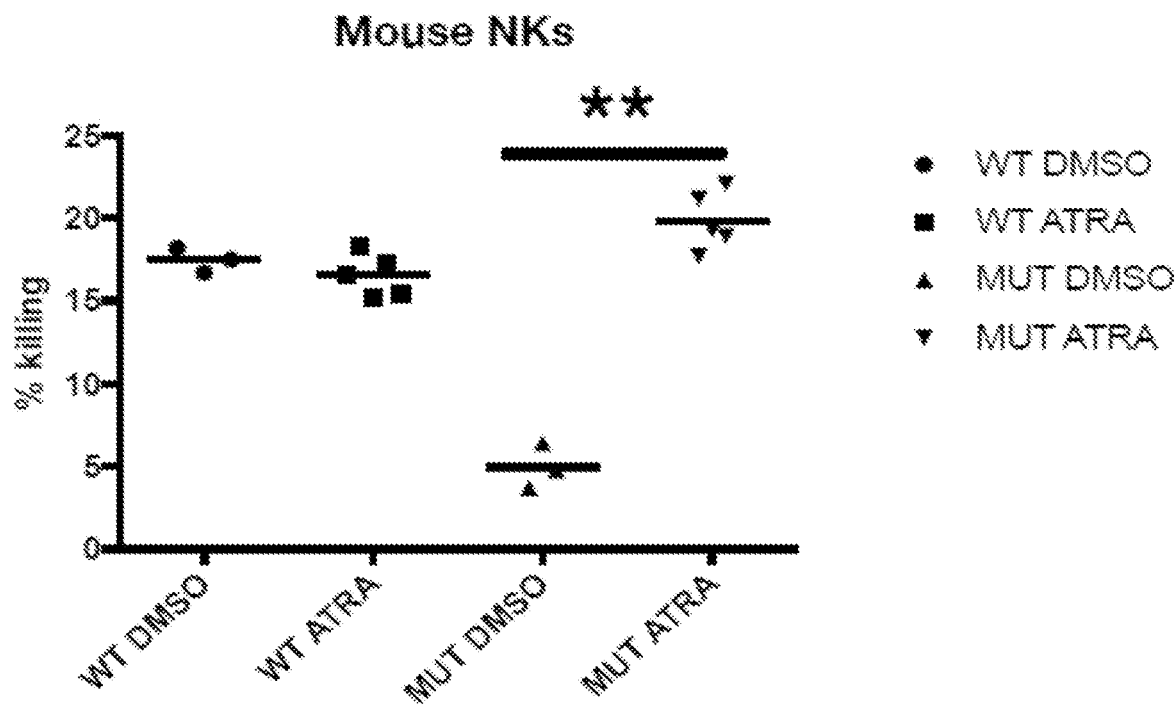
Figure 3D:
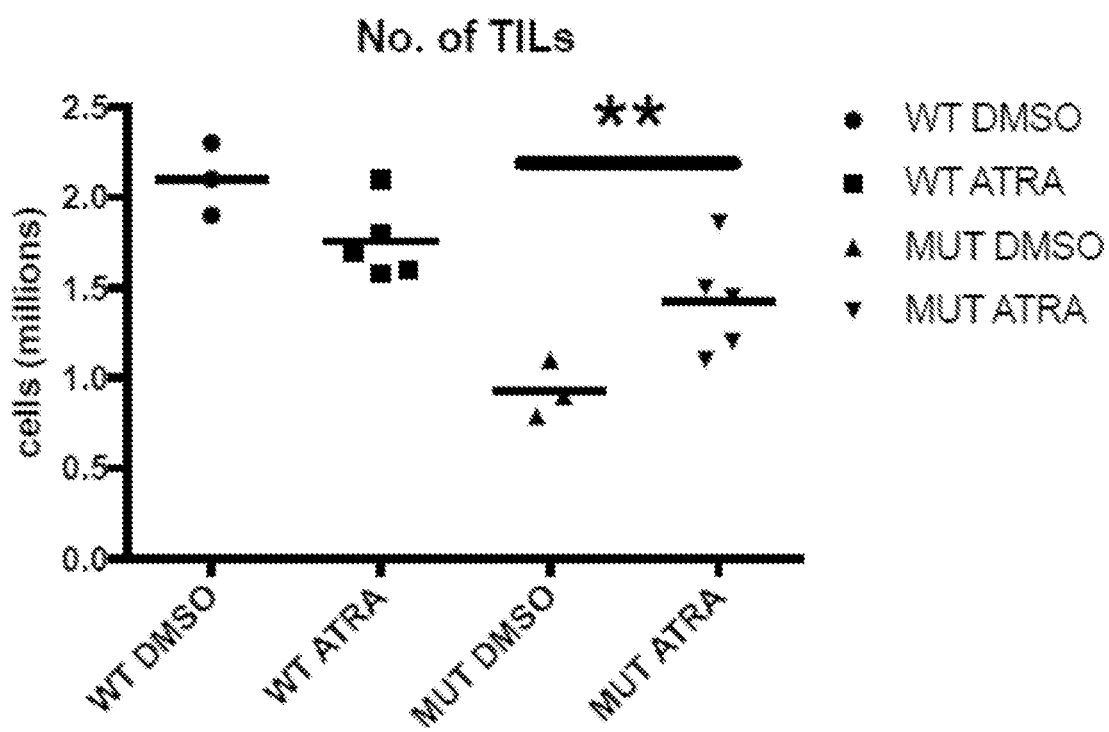
Figure 3E:
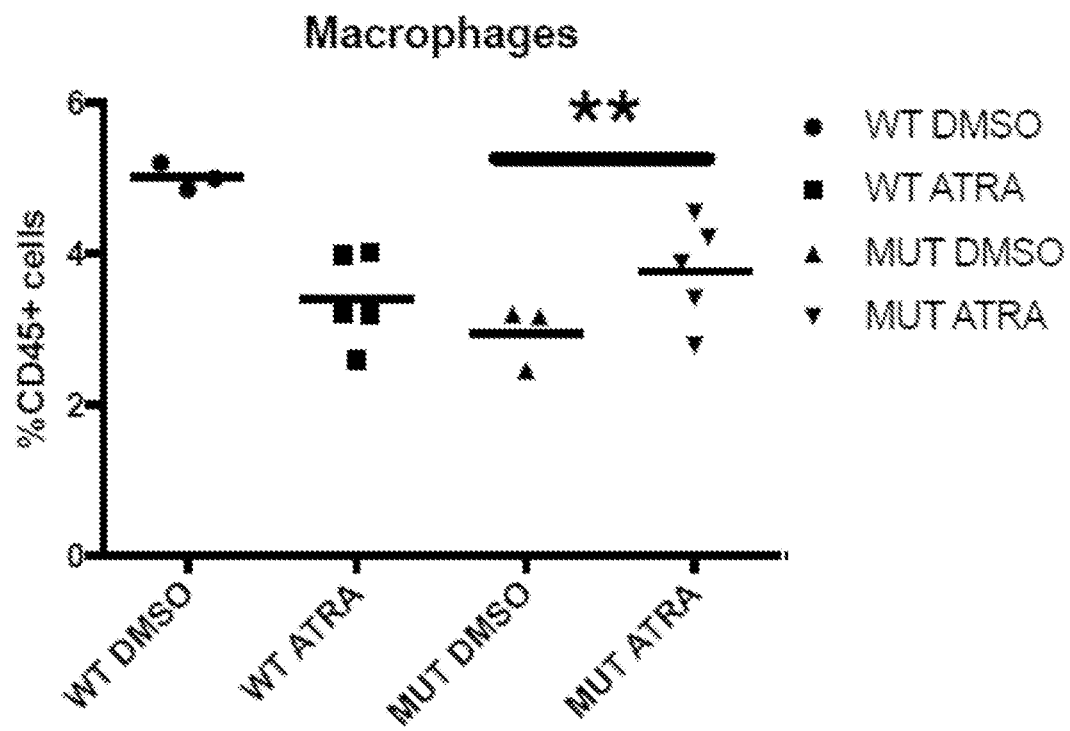
Figure 3F:
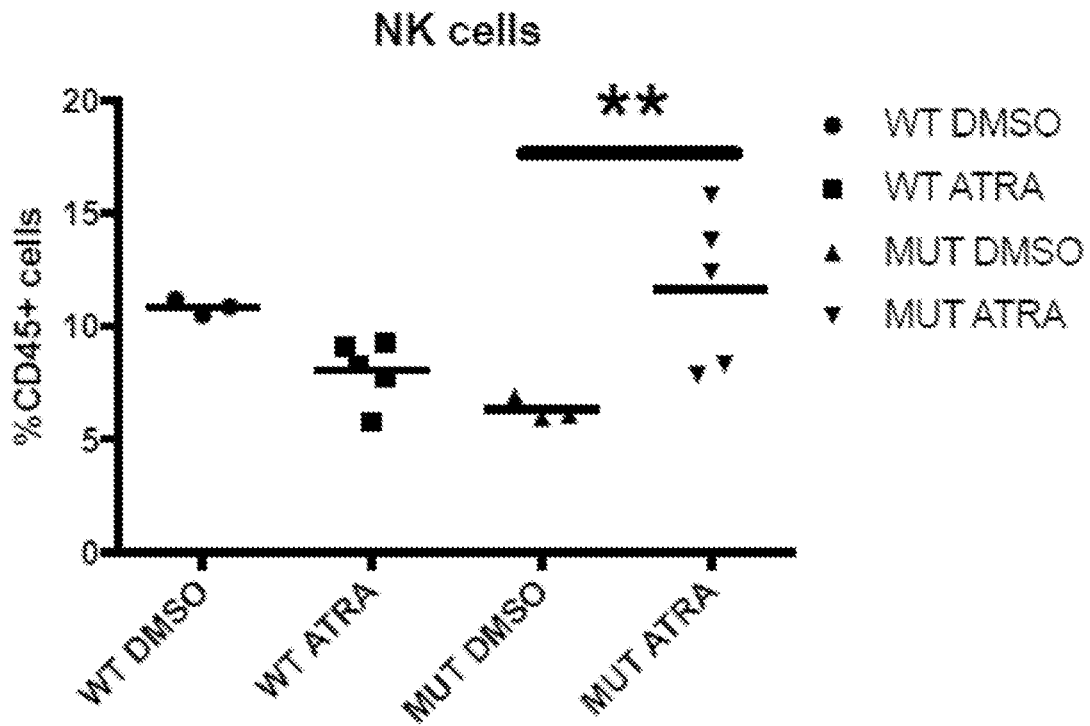
Figure 3G:
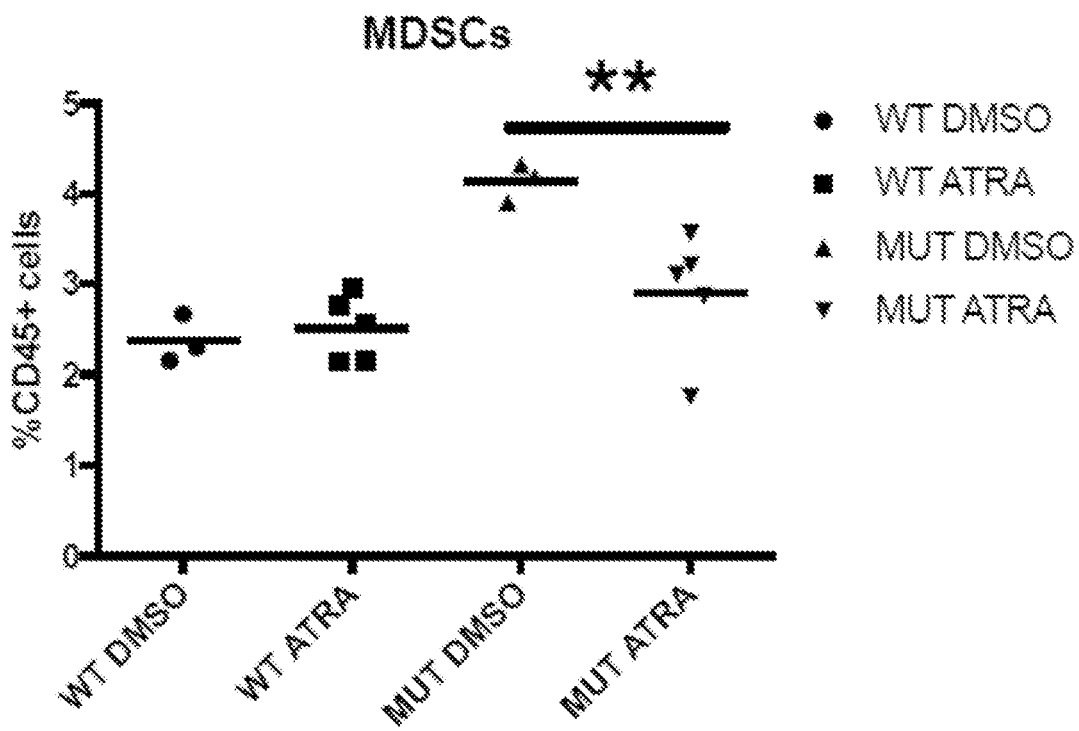

ATRA promotes tumor stasis in IDH mutant tumor-bearing mice. To determine the value of ATRA as a therapeutic modality, its anti-tumor efficacy in vivo was evaluated. Athymic nude mice were implanted with $10^6$ IDH mutant or WT primary glioma cells in the flank. 21 days after tumor inoculation (when tumors were about 25 mm²), 10 mg/kg ATRA was administered every other day for 21 days. Tumors were measured every 3 days. Mice treated with ATRA had significantly slower tumor growth compared with DMSO (vehicle)-treated mice, and mice with WT tumors (FIG. 3A). Resected tumors from ATRA or DMSO-treated mice were digested to obtain single cell suspensions and assessed for killing by human and mouse NK cells ex vivo. ATRA-treated IDH mutant tumors were more susceptible to killing by human (FIG. 3B) as well as mouse (FIG. 3C) natural killer cells, compared with DMSO-treated control tumors. The increased killing correlated with increased ex vivo expression of ULBP1 and ULBP3 in ATRA-treated IDH mutant tumors (data not shown). Analysis of tumor-infiltrating lymphocytes (TILs) showed that IDH mutant tumor-bearing mice treated with ATRA had higher infiltration of immune cells overall (FIG. 3D), comprising of a higher number of macrophages (FIG. 3E) and NKs (FIG. 3F), and lower MDSCs and monocytes (FIG. 3G) compared with DMSO-treated controls.

Figure 3H:
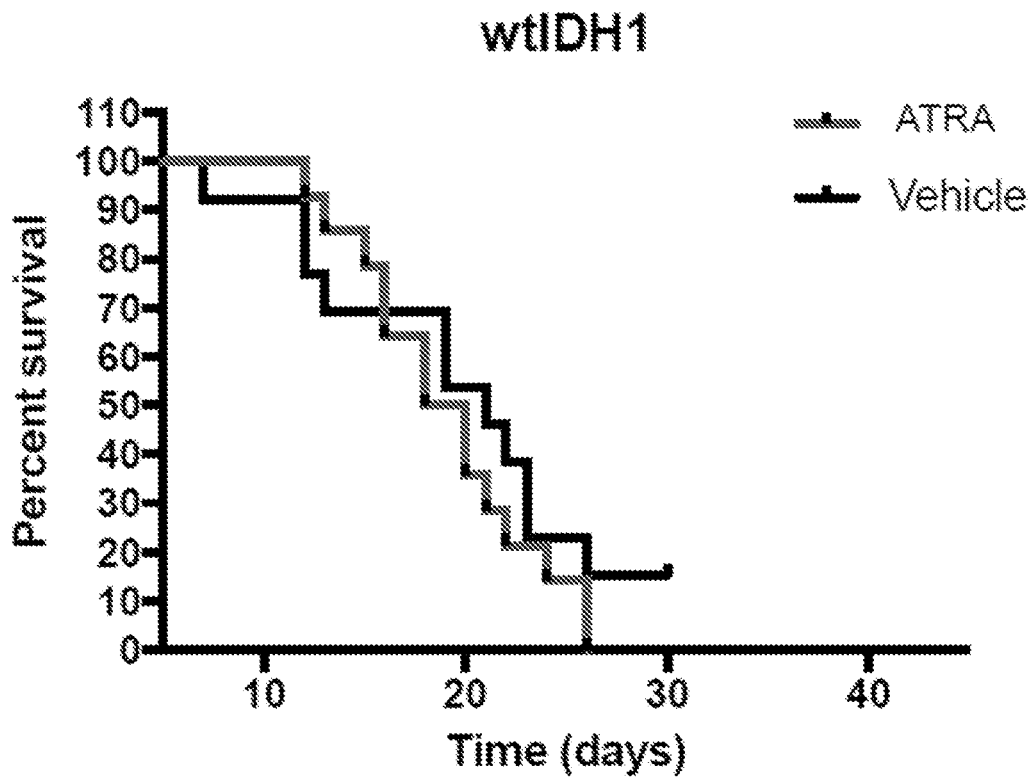
Figure 3I:
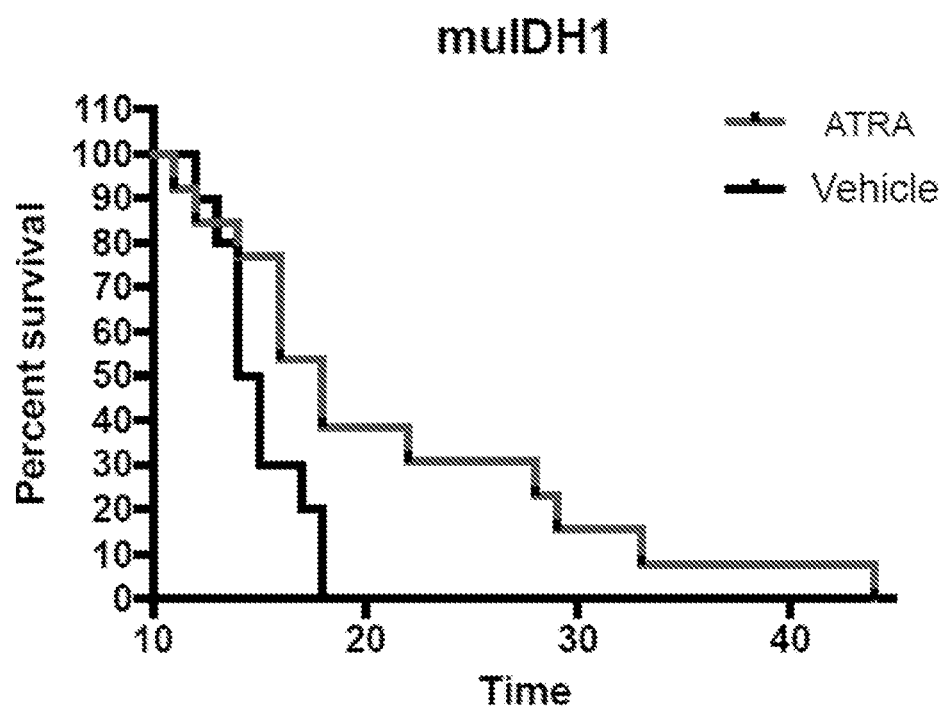
Figure 3J:
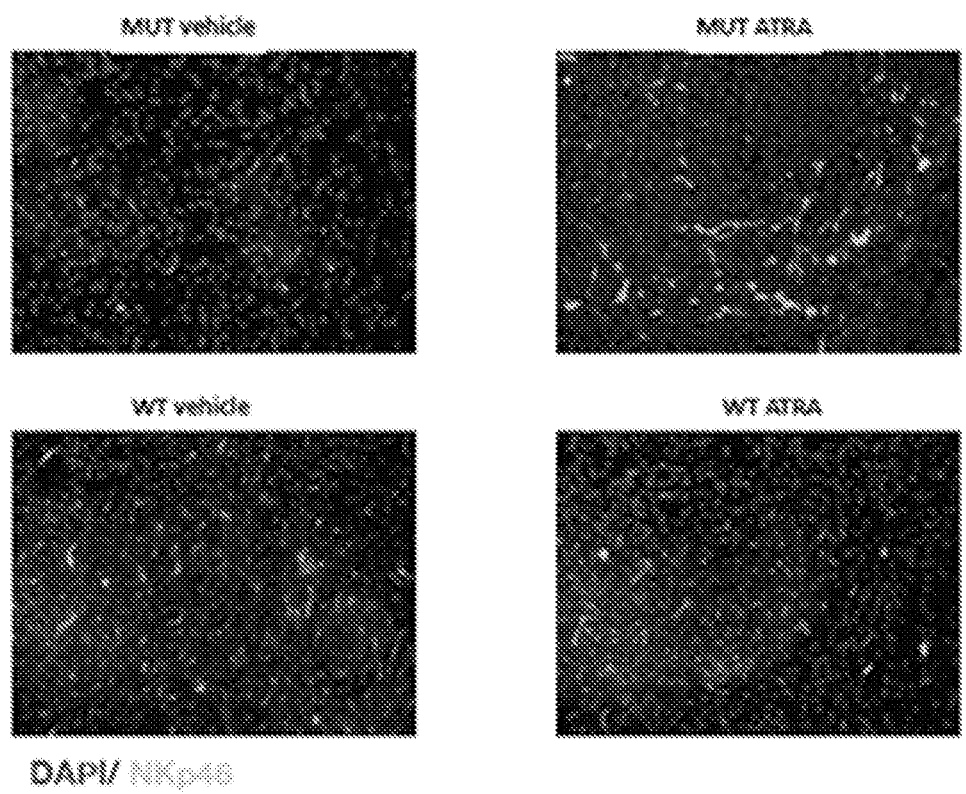

These studies were replicated in a RCAS tva mouse model that was ectopically induced to express the wild type or mutant IDH. As observed in the nude mouse model, mice bearing IDH mutant tumors (FIG. 3I) had significantly longer survival compare to vehicle-treated/IDH wild type tumor-bearing mice (FIG. 3H). Increased survival in ATRA-treated mice correlated with increased infiltration of NK cells in the tumor, as demonstrated by immunohistochemistry (FIG. 3J).

Figure 4A:
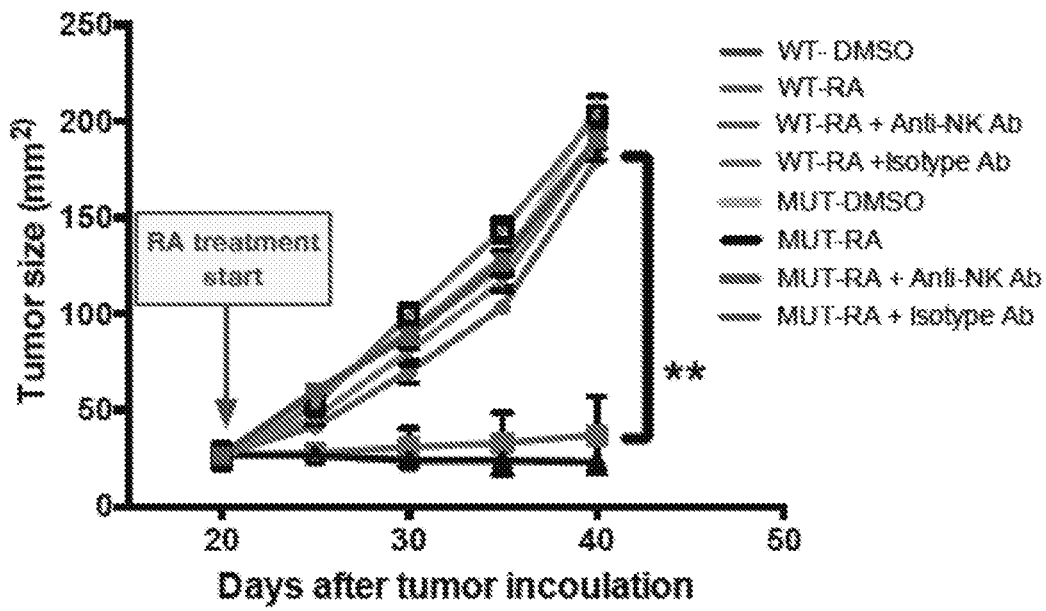
FIG. 4A is a graph showing tumor growth curves of mice from different groups. $p<0.05$. Tumors from all treatment groups were analyzed by ex vivo immune infiltrate analysis by flow cytometry to detect NK cells (FIG. 4B), macrophages (FIG. 4C), monocytes (FIG. 4D), and MDSCs (FIG. 4E). *$p<0.001$.
Figure 4B:
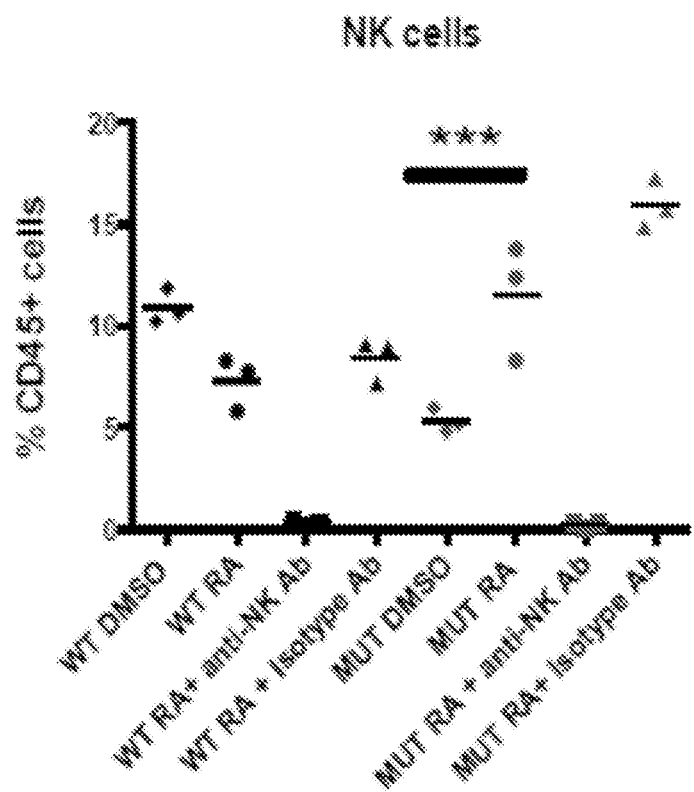
FIG. 4(A-F) are graphs and images showing ATRA efficacy in vivo is dependent on NK cells.
FIG. 4F shows immunohistochemistry analysis of NK infiltration in tumors at magnification 20× for each treatment group.
Figure 4C:
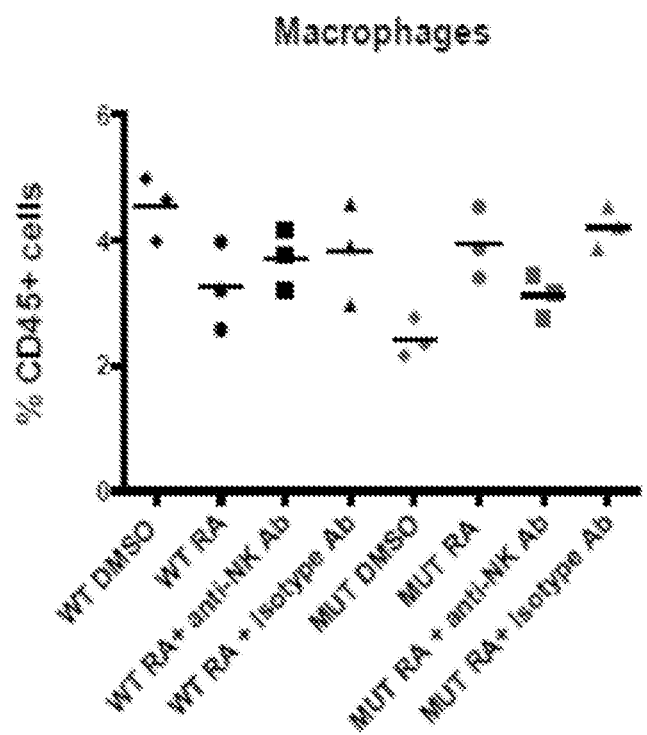
Figure 4D:
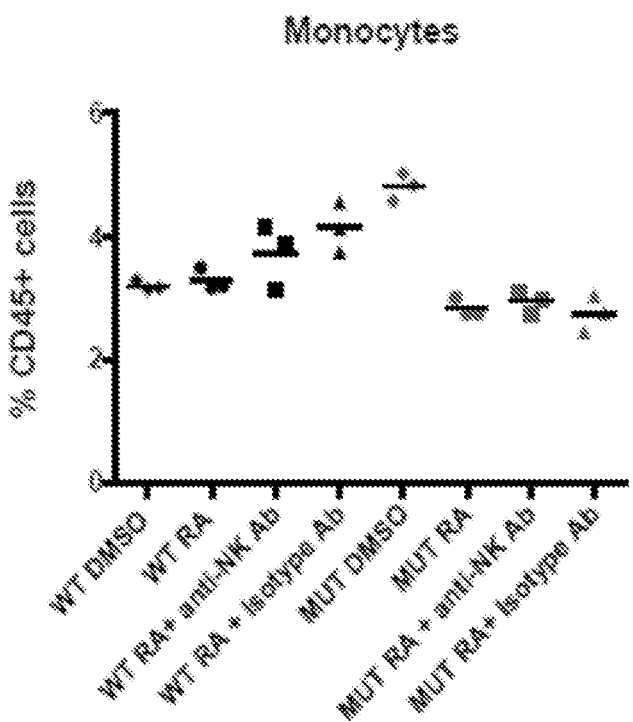
Figure 4E:
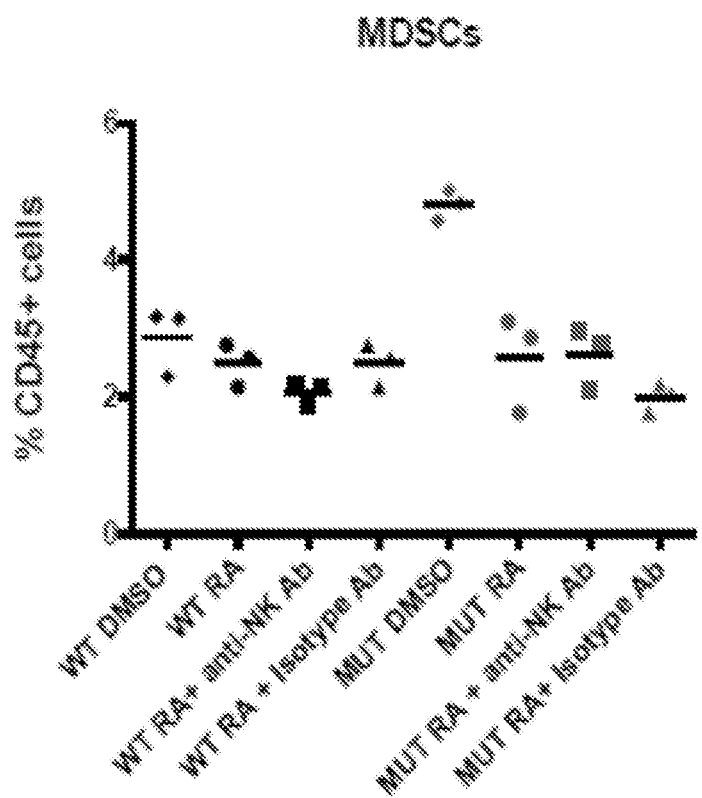
Figure 4F:
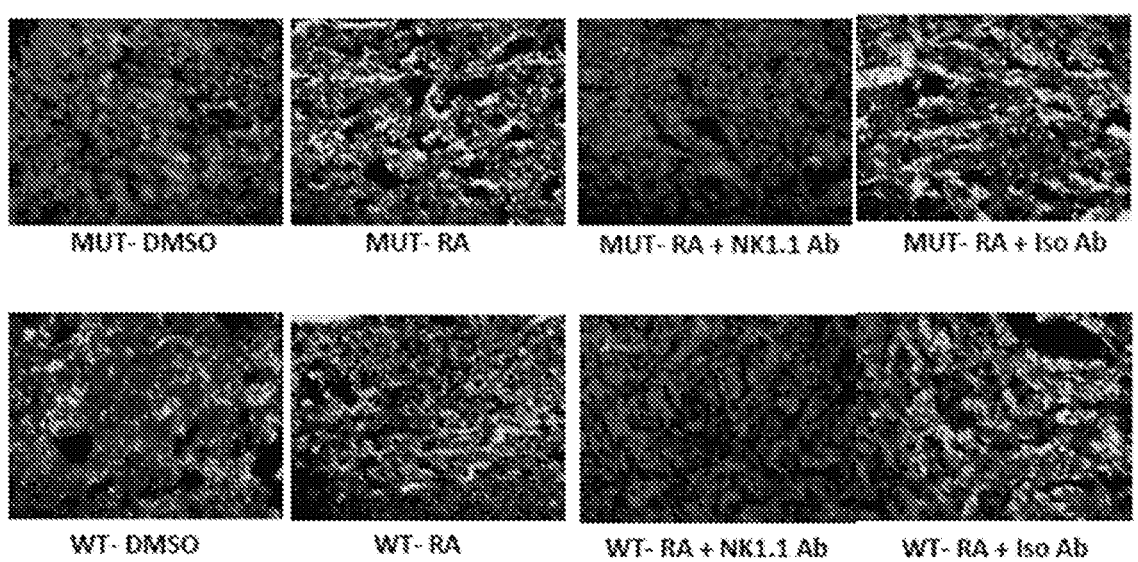

Anti-tumor effects of ATRA in vivo is dependent upon NK activity in vivo. Contrary to the delayed pro-differentiation effect of ATRA in vitro (FIG. 13A through 13D), the anti-tumor effects in vivo were more immediate. Thus, it was hypothesized that ATRA exercises alternate pathways to curb tumor growth. Previous studies demonstrated the ability of IDH mutant cells to evade recognition and killing by NK cells. To further substantiate the role of NKs in anti-tumor effect of ATRA, a NK blocking experiment was performed in vivo. Briefly, IDH mutant or WT tumor-bearing C57BL6/J nude mice were injected with 100 µg anti-NK1.1 (or control isotype) antibody intra-peritoneally on the first day of ATRA treatment. ATRA treatment was started when tumors were about 25 mm² in size and administered every other day. IDH mutant tumor-bearing mice treated with ATRA had significantly slower tumor growth compared with DMSO-treated controls. However, depletion of NKs abrogated the anti-tumor effects of ATRA, leading to tumor growth kinetics similar to DMSO-treated controls (FIG. 4A). Tumor infiltrating lymphocytes (TILs) analysis by flow cytometry showed that ATRA-treated mice had higher levels of NKs compared with DMSO-treated controls. However, NK-depleted mice showed no detectable presence of NKs, by flow cytometry (FIG. 4B) as well as by immunohistochemistry (FIG. 4F).

Figure 5A:
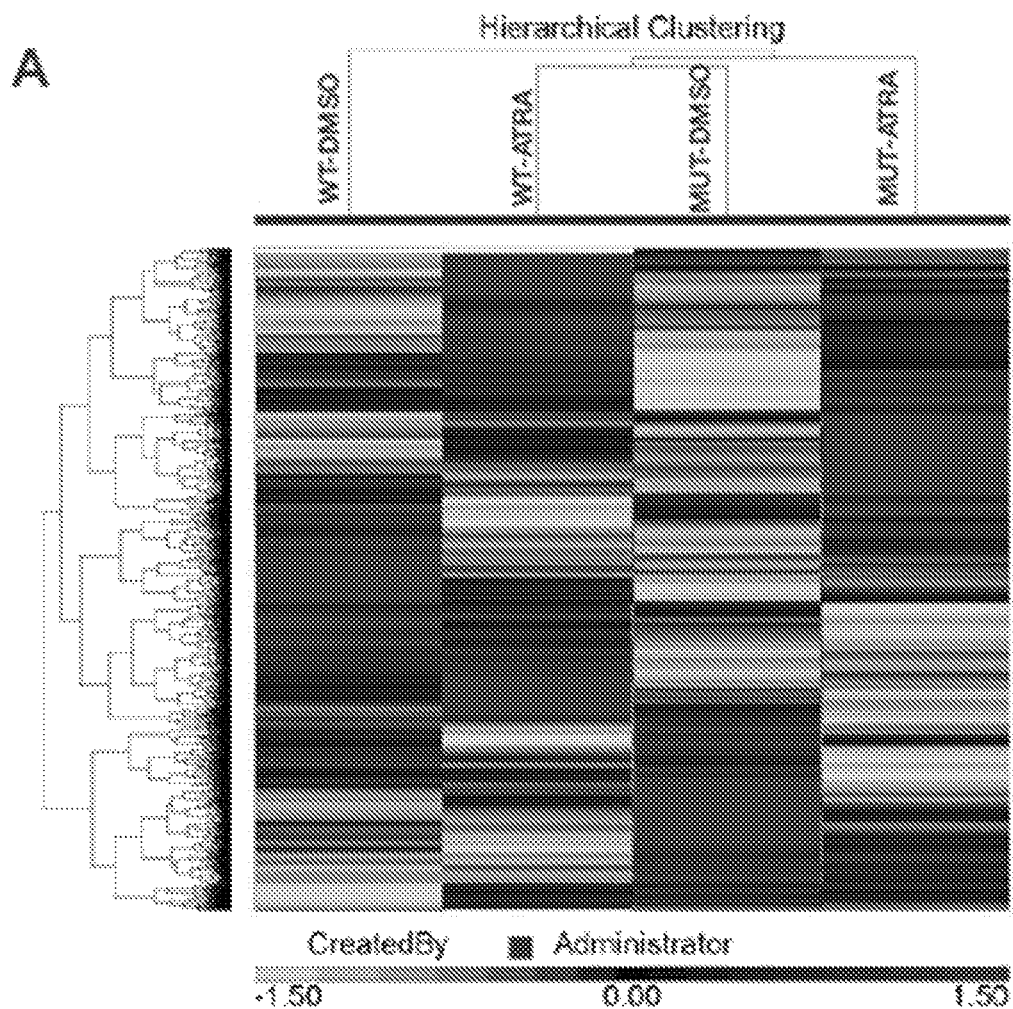
FIG. 5A is a schematic showing hierarchical clustering of untreated vs ATRA-treated IDH wild type and mutant cells.
Figure 5B:
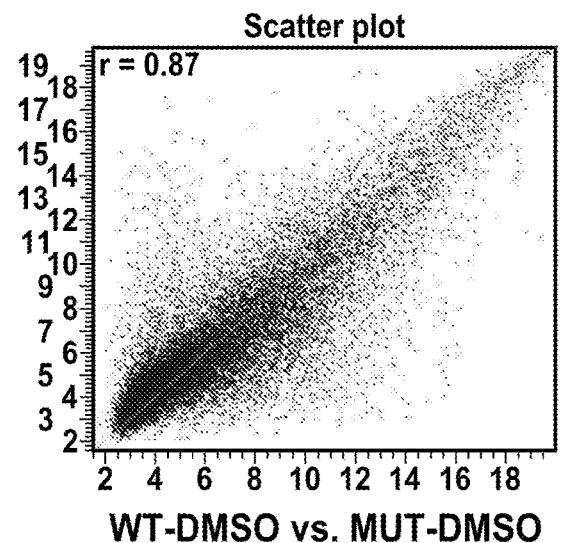
FIG. 5B is a set of graphs showing gene expression scatter plots of IDH WT cells treated with DMSO vs. IDH mutant cells treated with DMSO (top panel), IDH WT cells treated with DMSO vs. IDH WT cells treated with ATRA (middle panel), and IDH mutant cells treated with DMSO vs. IDH mutant cells treated with ATRA (bottom panel). Analysis for FIGS. 5A and 5B was done in using CLC Bio workbench.
Figure 5B:
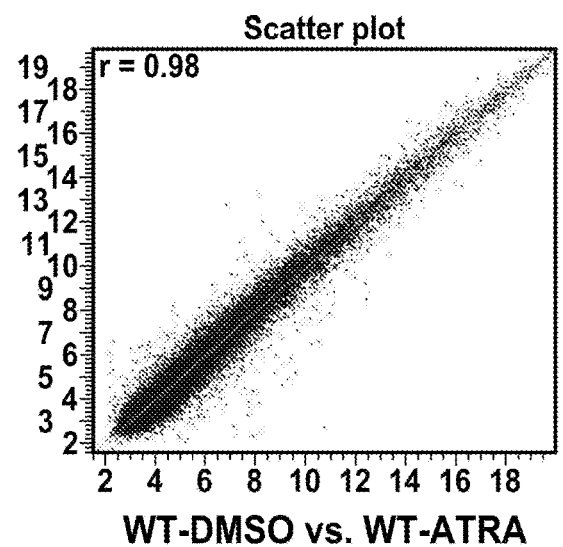
Figure 5B:
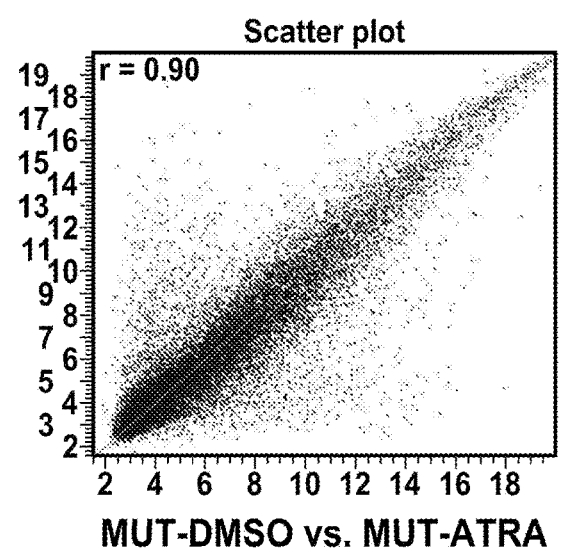
Figure 5C:
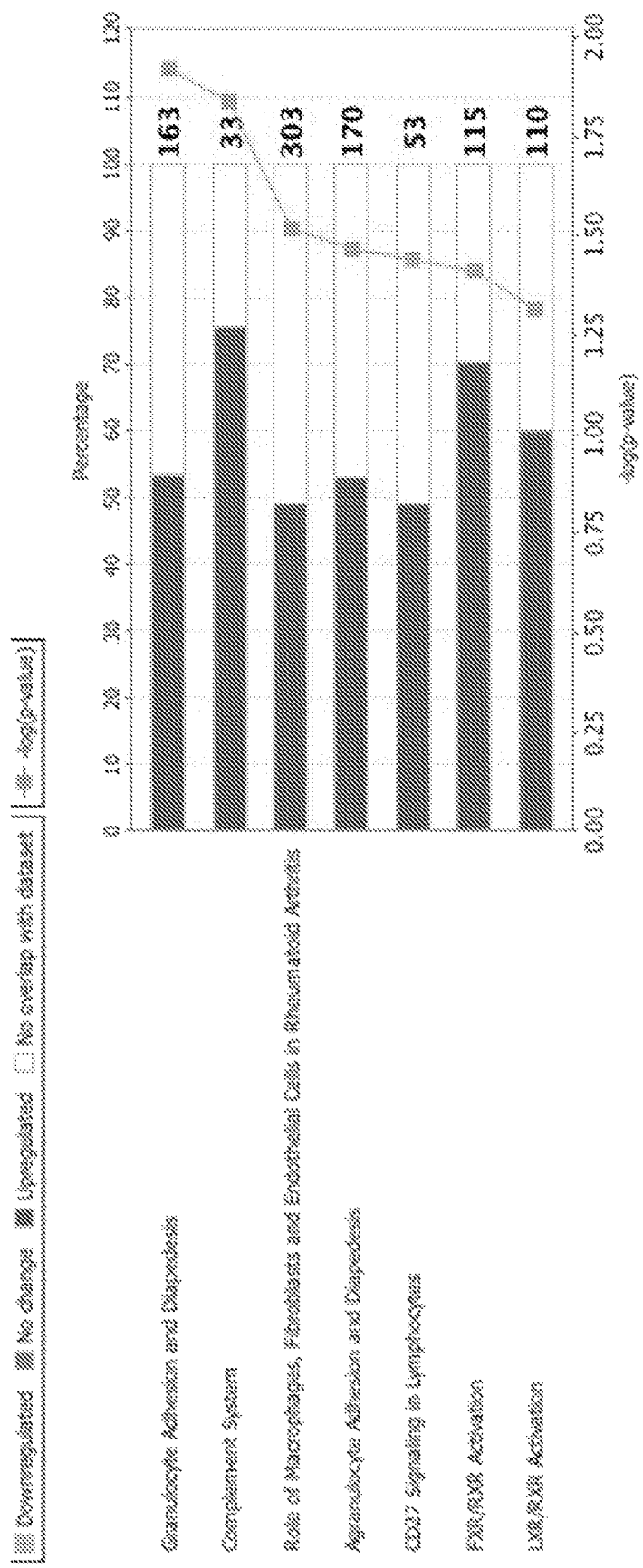
FIG. 5C is a schematic showing pathway analysis of upregulated genes in ATRA-treated IDH mutant cells using IPA pathway analysis software.

ATRA induces genetic changes in IDH mutant gliomas, with an emphasis on immune cell chemotaxis. To evaluate overall gene expression changes and to decipher pathway activation in IDH mutants after ATRA treatment, a gene microarray was performed. IDH wt and mutant cells from primary gliomas were treated with 1 µM ATRA for 48 hours and RNA was extracted from the cells. Microarray analysis was performed using Clariom S microarray chips. ATRA was observed to induce a wide-ranging effect on IDH mutant cells, as seen in heat maps (FIG. 5A) and PCA analysis (FIG. 5B). Pathway analysis revealed that immune cell chemotaxis was one of the most upregulated pathways in ATRA-treated IDH mutant cells (FIG. 5C). ATRA also upregulated the gene expression of multiple inflammatory chemokines such as CXCL1, CXCL9 and CXCL10 (data not shown). Therefore, the chemotactic effects of ATRA was investigated in several vitro experiments.

Figure 6A:
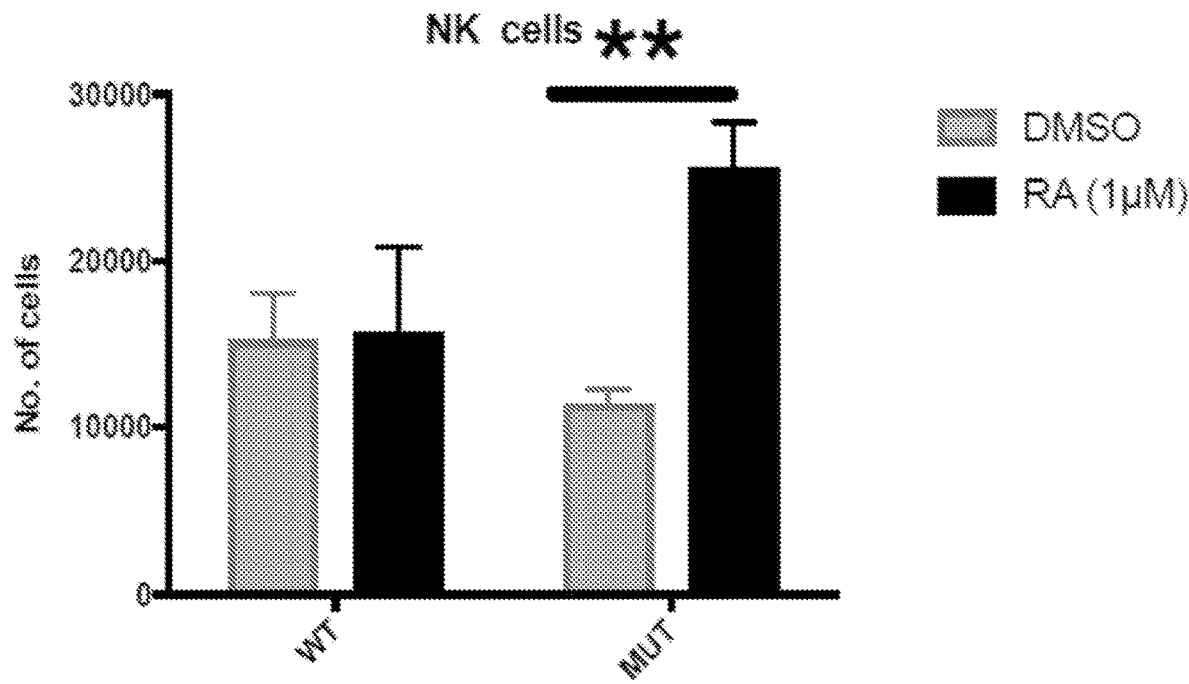
FIG. 6(A-O) are graphs and images showing ATRA induces increased NK chemotaxis of NK cells in a CCL2-dependent fashion. The number (absolute cell count) of NK cells (FIG. 6A), CD8+ cells (FIG. 6B), M1 macrophages (FIG. 6C), CD4+ Tregs (FIG. 6D), monocytes (FIG. 6E), and M2 macrophages (FIG. 6F) harvested from the lower chamber after 48 hours transwell assays are shown. All cells from the lower chamber were harvested and analyzed by flow cytometry. The gating strategy for the different immune cell subsets was as follows: NK cells: CD45+CD56+, CD8 T cells: CD3+CD8+, Tregs: CD3+CD4+CD25+, M1 macrophages: CD11b+CD80+CD86+, M2 macrophages: CD11b+CD163+, Monocytes CD45+CD14+.
FIG. 6G is a set of dot blots from a chemokine array performed on supernatants from IDH mutant and WT cells treated with ATRA or DMSO. The integrated density analysis of dot blots for CXCL12 (FIG. 6H) and CCL2 (FIG. 6I) was calculated from FIG. 6G. The dot blot density was normalized to density of control blots (gp100). Primary glioma cells treated with ATRA or DMSO were analyzed for gene expression of transcripts of the chemokines CCL2 (FIG. 6J), CXCL12.1 (FIG. 6K), and CXCL12.2 (FIG. 6L). Results are representative of three independent experiments. Migration of NK cells (FIG. 6M), CD8+ T cells (FIG. 6N) and Tregs (FIG. 6O) towards ATRA- or DMSO-treated IDH mutant or WT primary glioma cells, in the presence of Isotope antibody or CCL2 blocking antibody, is also shown. **$p<0.005$.
Figure 6B:
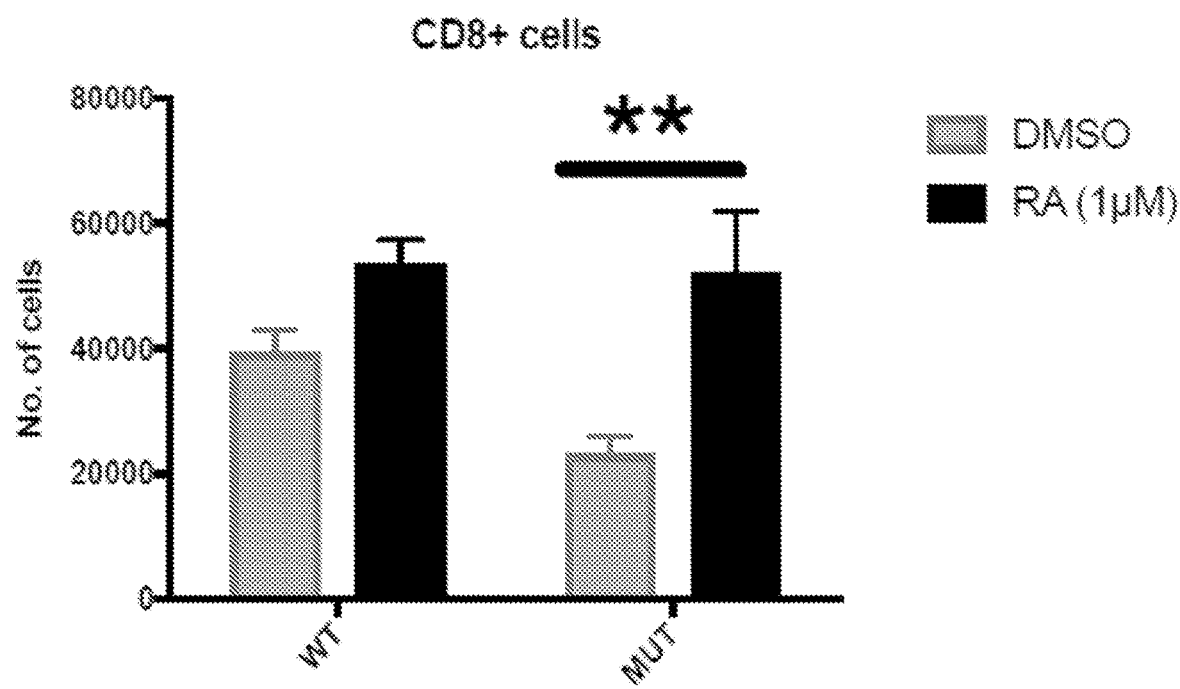
Figure 6C:
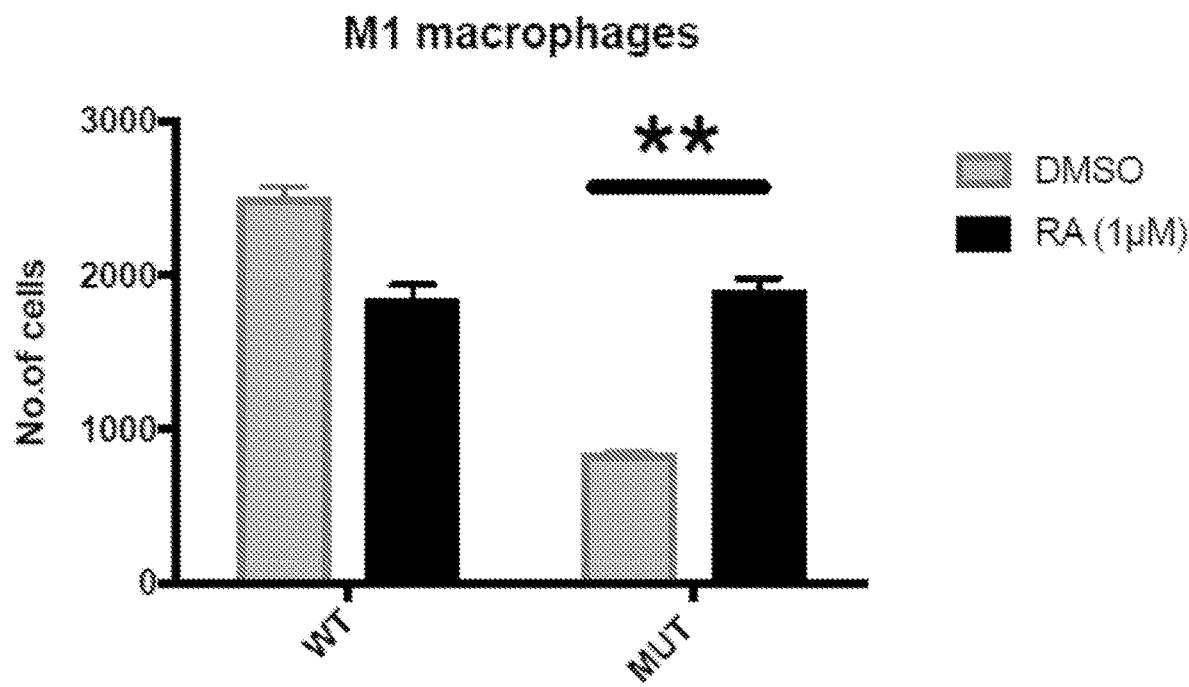
Figure 6D:
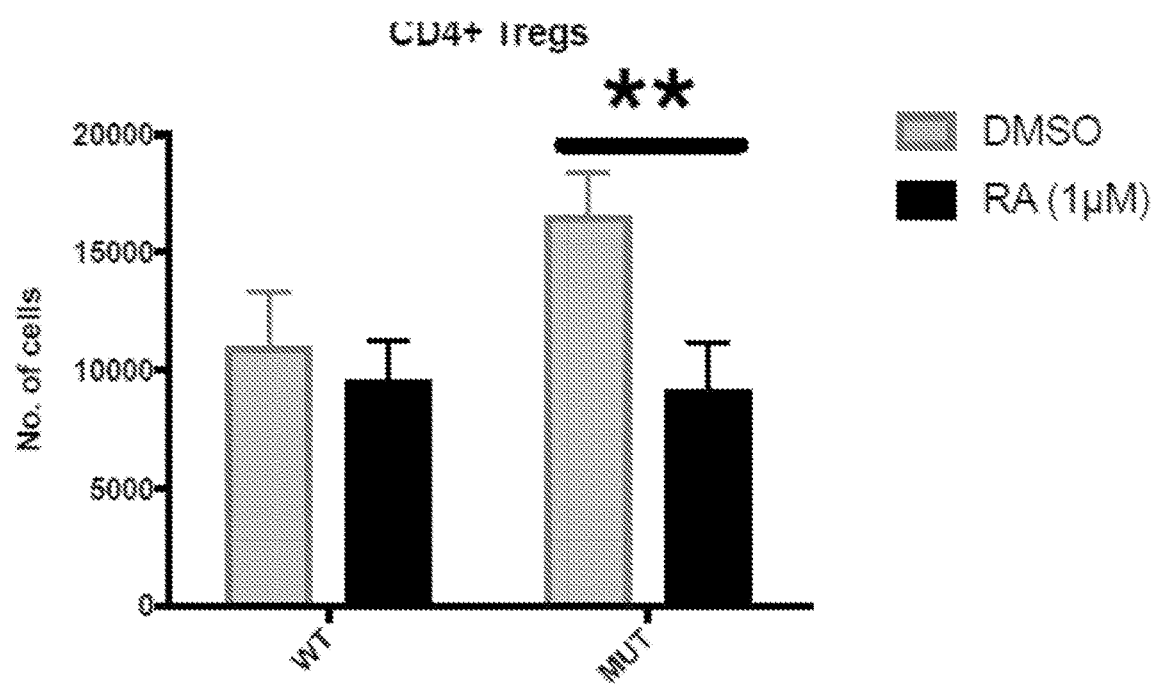
Figure 6E:
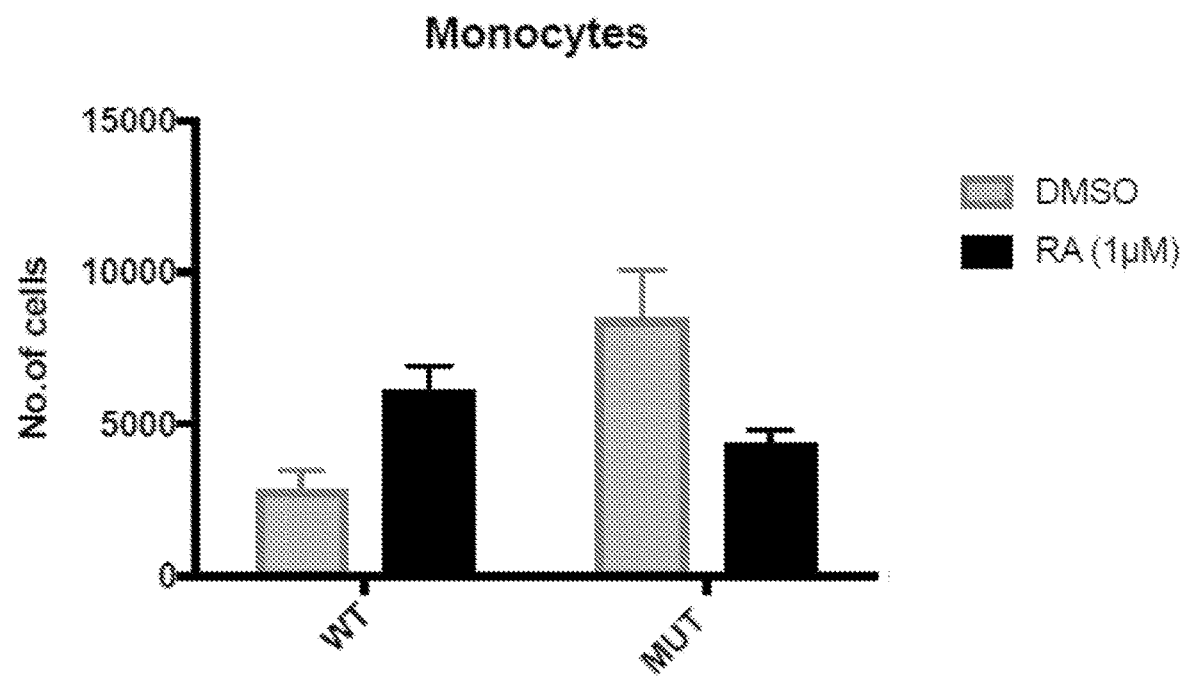
Figure 6F:
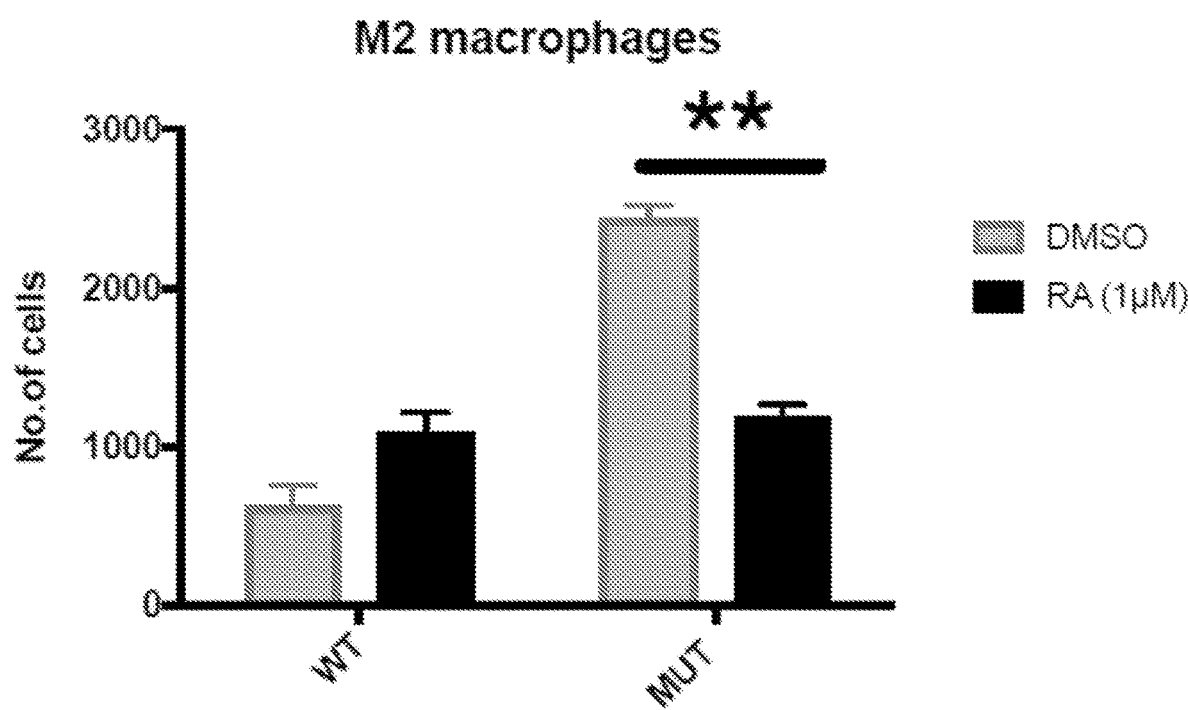
Figure 6G:
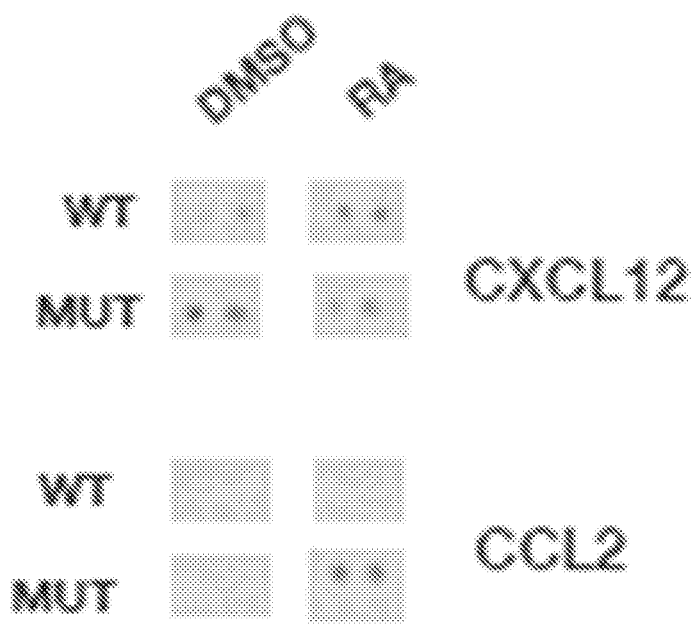
Figure 6H:
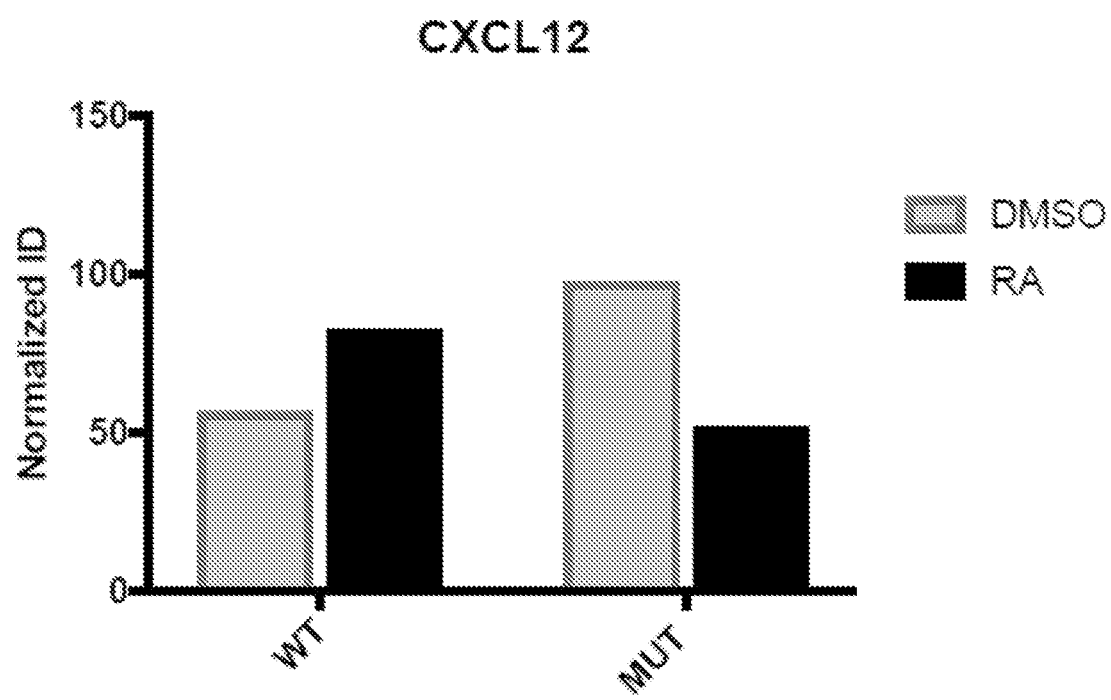
Figure 6I:
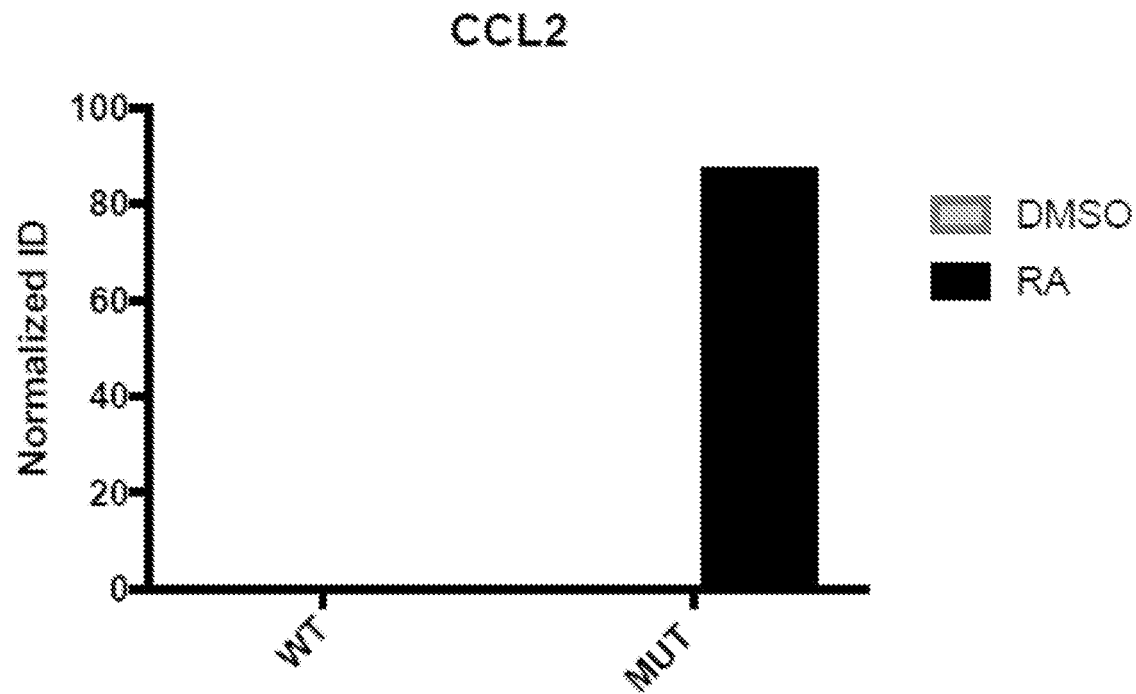
Figure 6J:
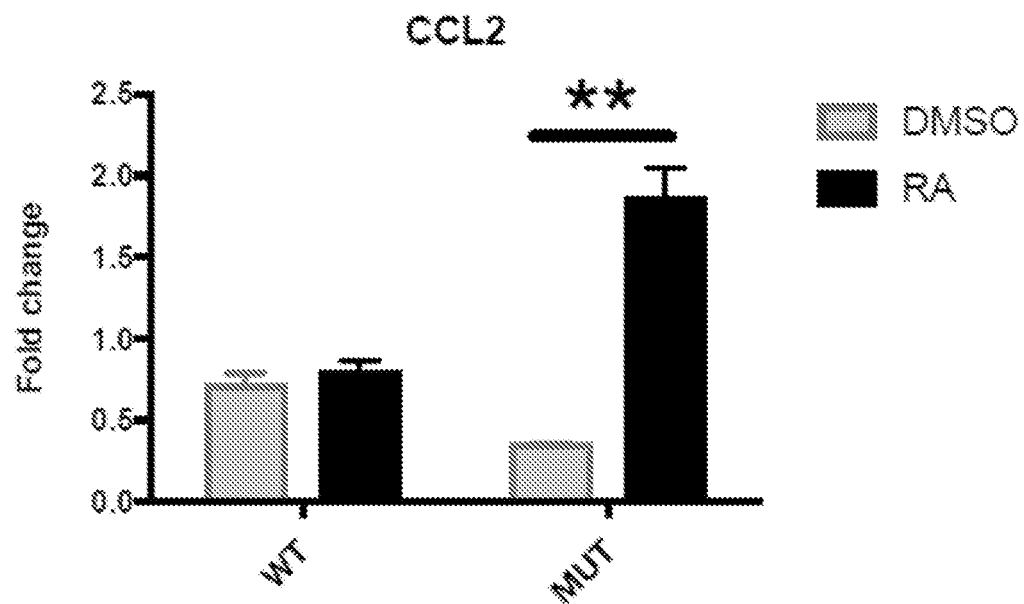
Figure 6K:
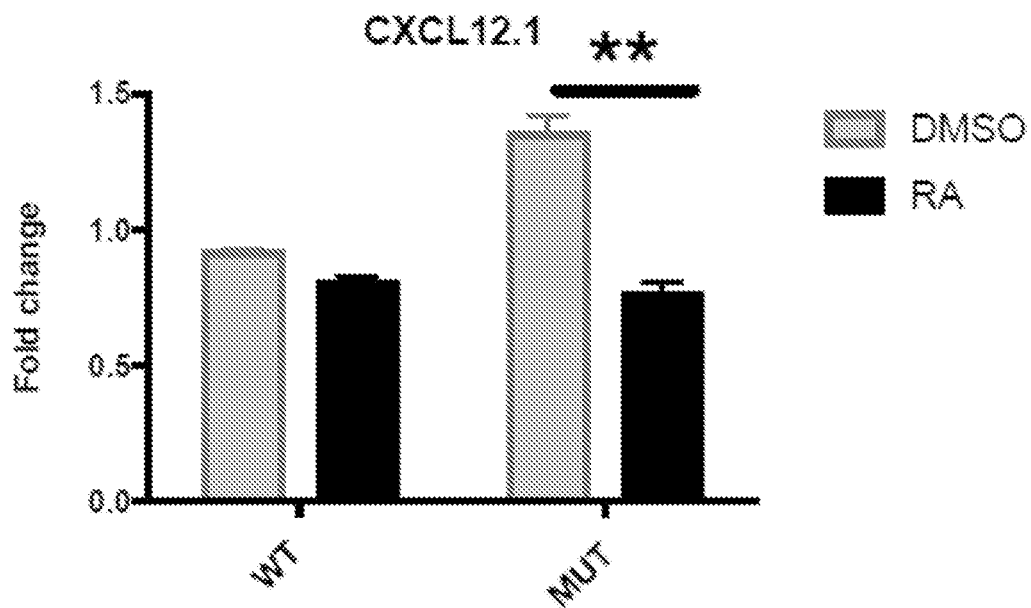
Figure 6L:
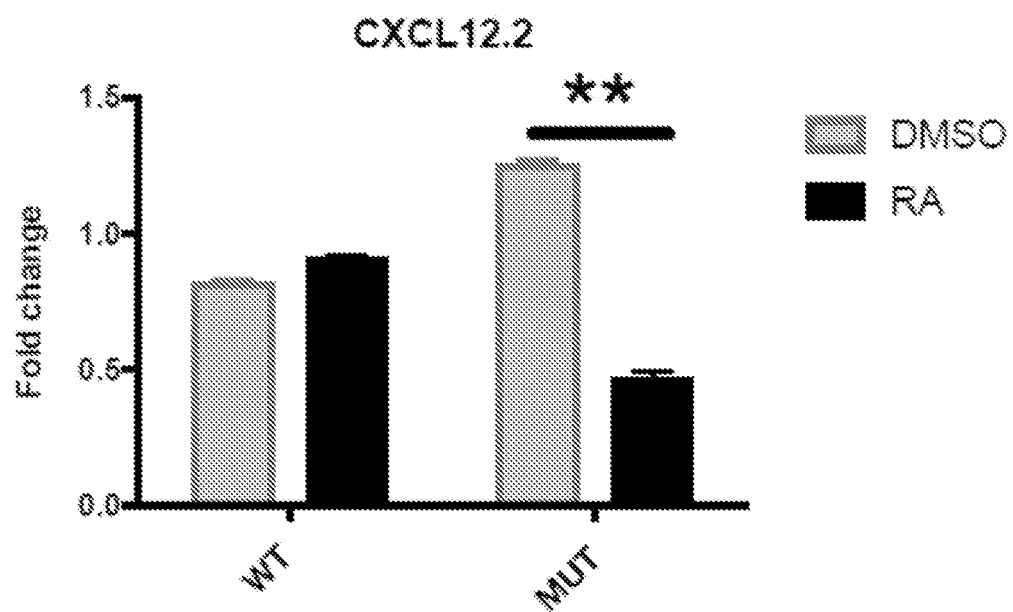
Figure 6M:
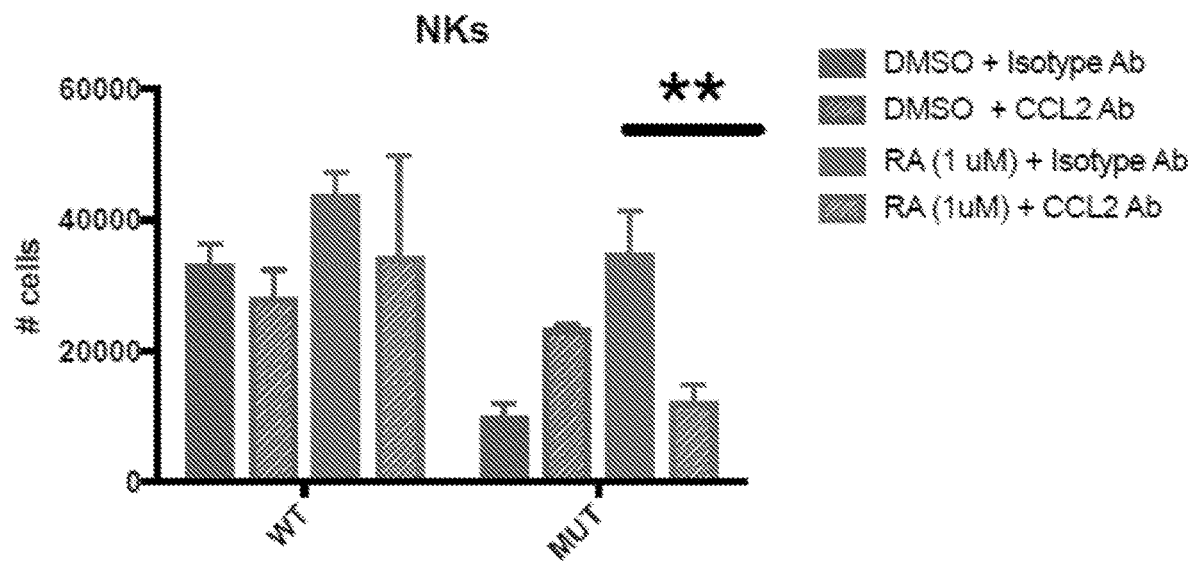
Figure 6N:
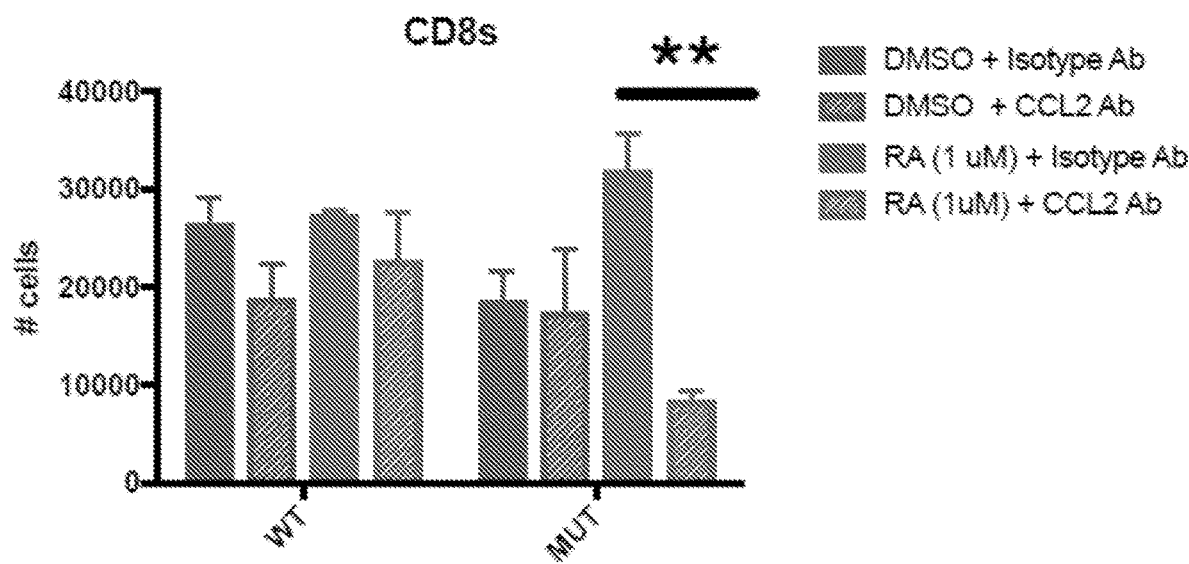

ATRA increases chemotaxis towards IDH mutant cells in a CCL2-dependent manner. In vivo, ATRA induced changes in the tumor microenvironment, inducing increased migration of NK cells, and decreased MDSCs and monocyte migration (FIG. 3A through 4F). To confirm these findings, chemotaxis assays were performed in vitro. ATRA-treated IDH mutant or WT cells were plated in the bottom well of a transwell. Different immune cell subsets (as indicated) were placed in the top chamber at a 10:1 E:T ratio. After 48 hours, cells from the bottom chamber were harvested and analyzed by flow cytometry. NK cells (FIG. 6A), CD8+ T cells (FIG. 6B), and M1 macrophages (FIG. 6C) had increased migration towards ATRA-treated IDH mutant cells, versus DMSO-treated controls. Conversely, there was decreased migration of Tregs (FIG. 6D), Monocytes (FIG. 6E), and M2 macrophages (FIG. 6F) towards ATRA-treated IDH mutants cells. To evaluate the mechanisms of changes in chemotaxis induced by ATRA, a chemokine array was performed. Supernatants from ATRA- (or DMSO)-treated WT and IDH mutant cultures were used to assess changes in chemokine expression using a chemokine array kit (R&D systems). Results were interpreted visually as well as quantified using an imaging software (ImageJ). Two major changes in ATRA-treated IDH mutant cells were observed, versus other groups: (i) CCL2 production was only observed in ATRA treated IDH mutant cells, and not observed in any other groups. (ii) ATRA-treated IDH mutant cells had lower levels of CXCL12 compared with DMSO-treated controls (FIGS. 6G and 6H). PCR analysis of ATRA- or DMSO-treated cells confirmed these findings (FIGS. 6K and 6L). To substantiate the role of CCL2 in NK and T cell chemotaxis, transwell assays were repeated as described earlier, in the presence of CCL2-blocking antibody (R&D systems). CCL2 blocking reversed the increased NK (FIG. 6M) and T cell (FIG. 6N) migration induced by ATRA in IDH mutant cells. Incidentally, CCL2 blocking did not impact the migration of Tregs (FIG. 6O) observed in ATRA-treated IDH mutant cells.

Figure 7A:
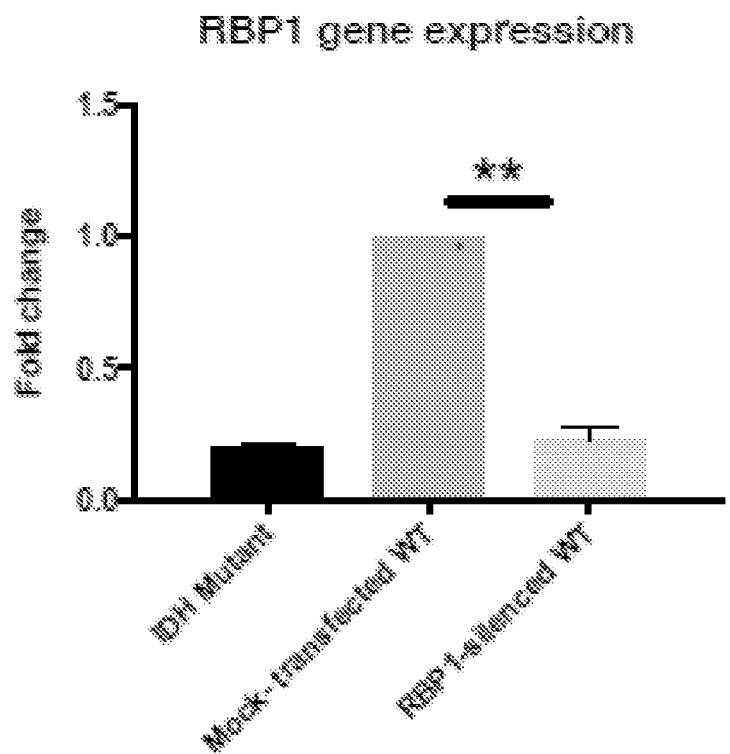
FIG. 7A is a graph showing RBP1 gene expression in mock- and RBP1-silenced cells. Expression normalization was carried out against mock-transfected WT cells.
Figure 7B:
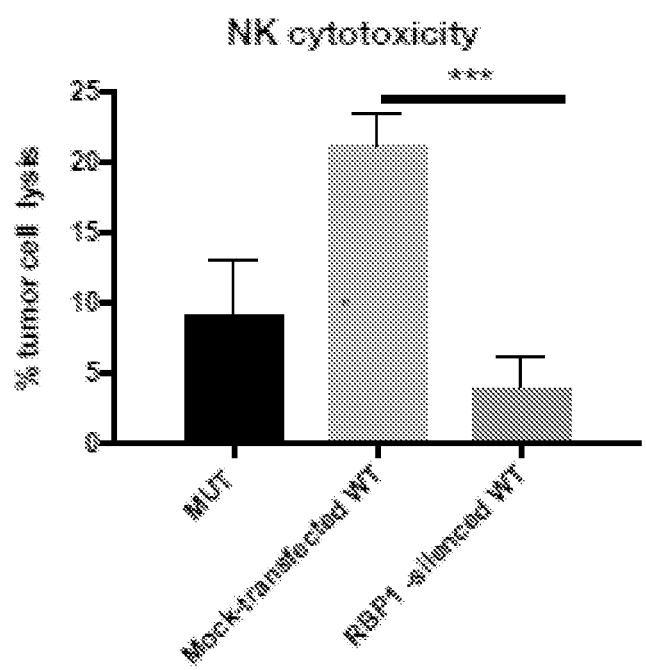
FIG. 7B is a graph showing NK-mediated cytotoxicity in RBP1 silenced cells. An E:T ratio of 1:10 was used, and tumor cell death was measured by flow cytometry, by determining percent of 7-AAD+ cells. Gene expression of the NKG2D ligands ULBP1 (FIG. 7C), ULBP2 (FIG. 7D), and ULBP3 (FIG. 7E) were analyzed by qPCR.
Figure 7C:
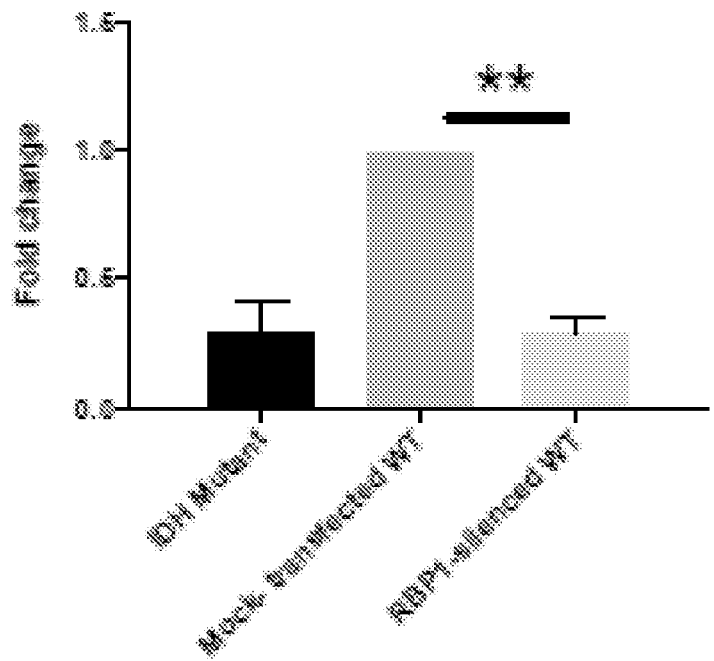
FIG. 7(A-F) shows effects of RBP1 gene silencing on IDH WT cells.
FIG. 7F is a heat map showing qPCR gene expression analysis of genes downstream of retinoid acid signaling.
Figure 7D:
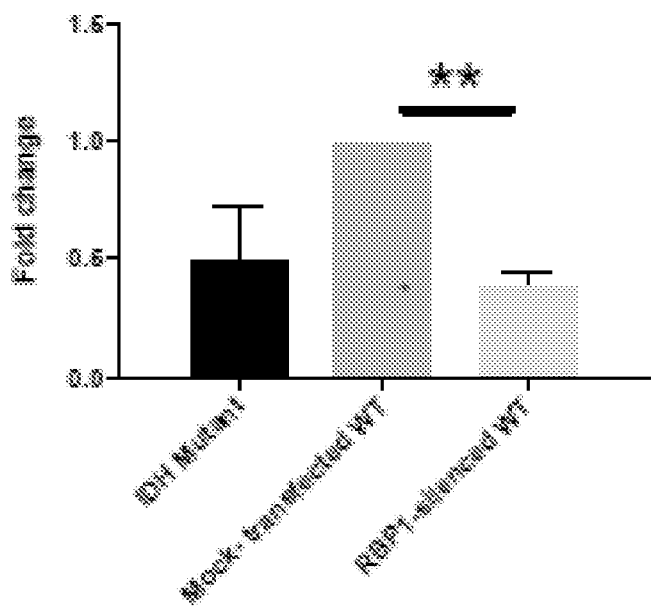
Figure 7E:
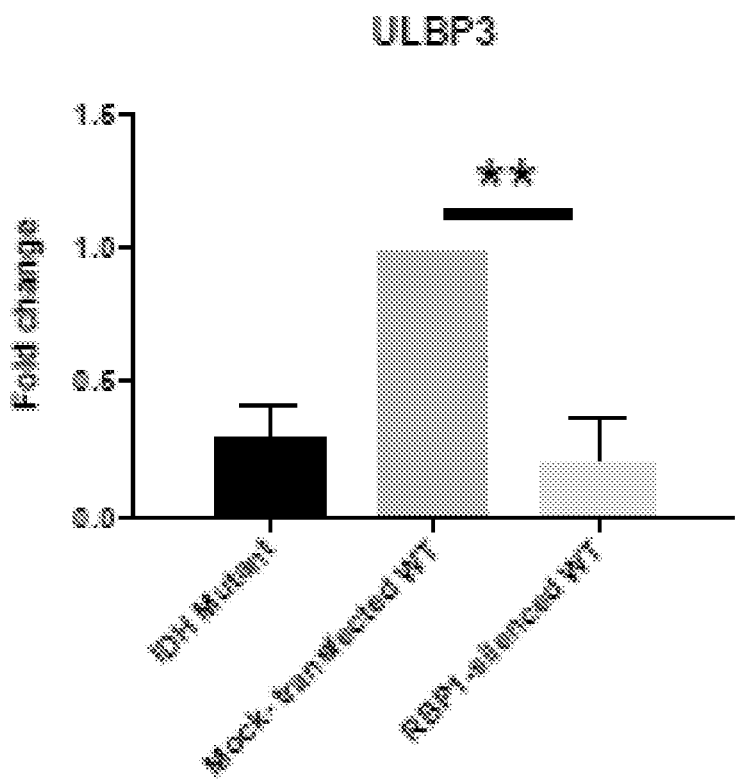
Figure 7F:
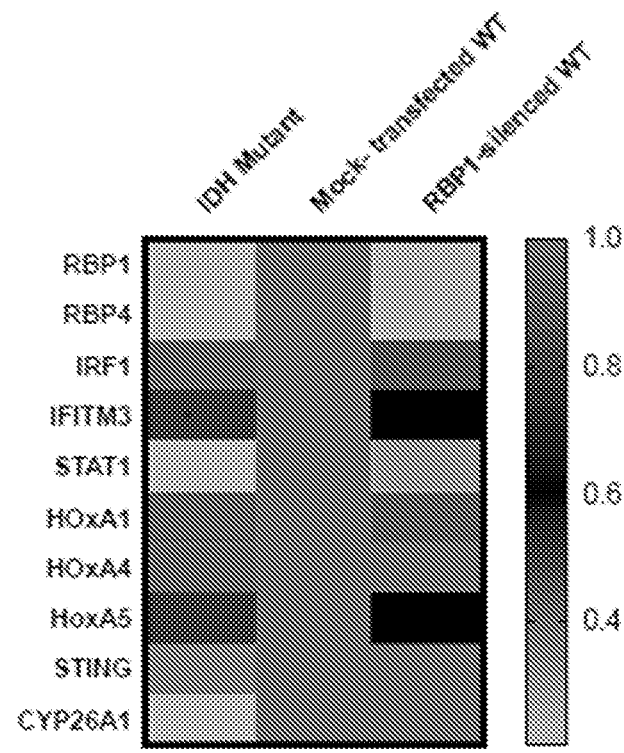

RBP1 down regulation emulates the IDH mutant phenotype in IDH WT cells. IDH mutant cells have decreased RBP1 levels, leading to impaired RA production. Results thus far demonstrated that supplementing IDH mutant cells with ATRA effectively overcomes the immune evasion observed in IDH mutant tumors. Therefore, the role of RBP1 silencing in generation of the IDH mutant immune evasive phenotype was further investigated. Lentiviral RBP1shRNA was transduced into IDH WT cells to silence the RBP1 gene. IDH WT cells transfected with a mock vector (mock-transfected) served as controls. RBP1 shRNA transfection and gene knockdown was confirmed by PCR (FIG. 7A). To determine whether RBP1 knockdown affected NK recognition and killing, RBP1-silenced cells were assessed for NKG2D-L expression by PCR and killing by NK-92 cells, as described earlier. RBP1-silenced cells had significantly lower killing by NK-92 cells compared with mock-transfected cells. In fact, RBP1 silencing reduced killing to mutant levels (FIG. 7B). RBP1 silencing also affected NKG2DL levels for ULBP1 (FIG. 7C), ULBP2 (FIG. 7D), and ULBP3 (FIG. 7E) in transfected IDH WT cells, decreasing them to IDH mutant levels. In addition, a significant down regulation in genes associated with retinoic acid metabolism and signaling was observed (FIG. 7F). Thus, RBP1 silencing induced NK immune escape in IDH WT cells.

Figure 8A:
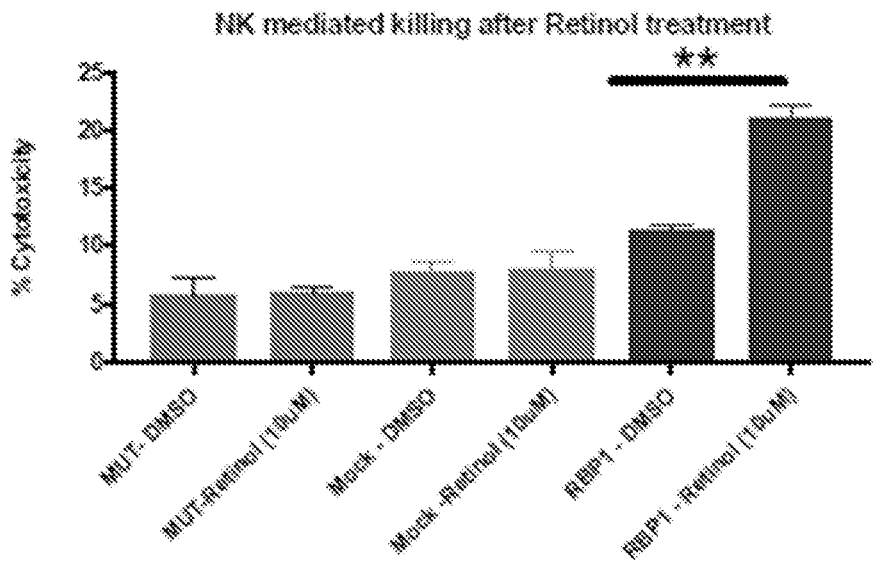
FIG. 8A is a graph showing NK mediated cytotoxicity in RBP1 or Mock-transduced cells, in the presence of 10 µM Retinol. E:T ratio of 1:10 was used, and tumor cell death was measured by flow cytometry, by determining percent 7-AAD+ cells.
Figure 8B:
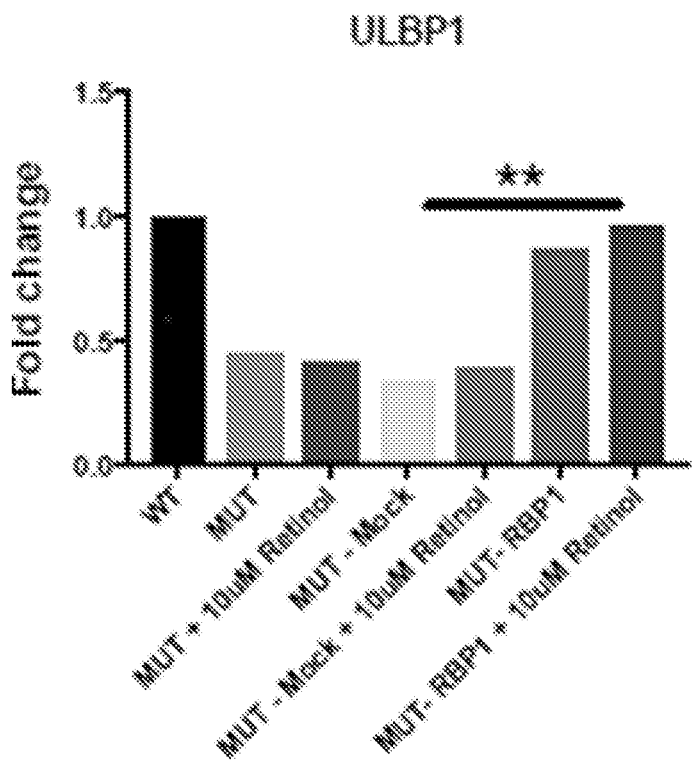
FIGS. 8B and 8C are graphs showing qPCR gene expression of the NKG2D ligands ULBP1 (FIG. 8B) and ULBP3 (FIG. 8C).
Figure 8C:
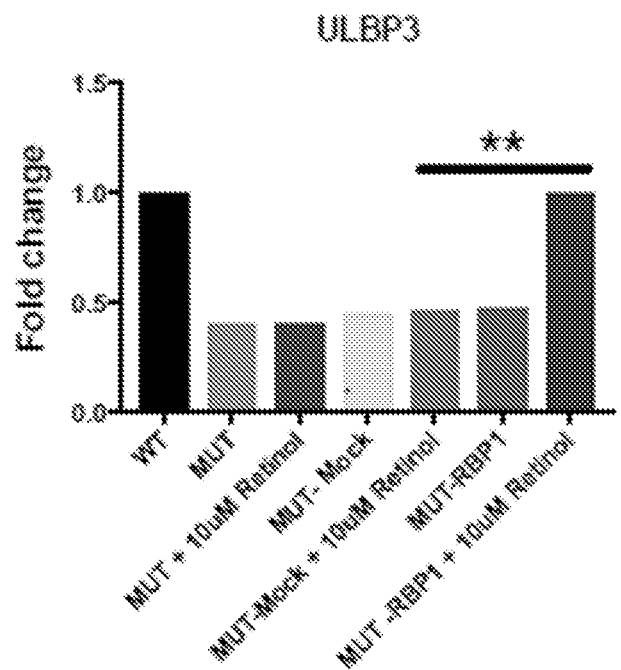
Figure 8D:
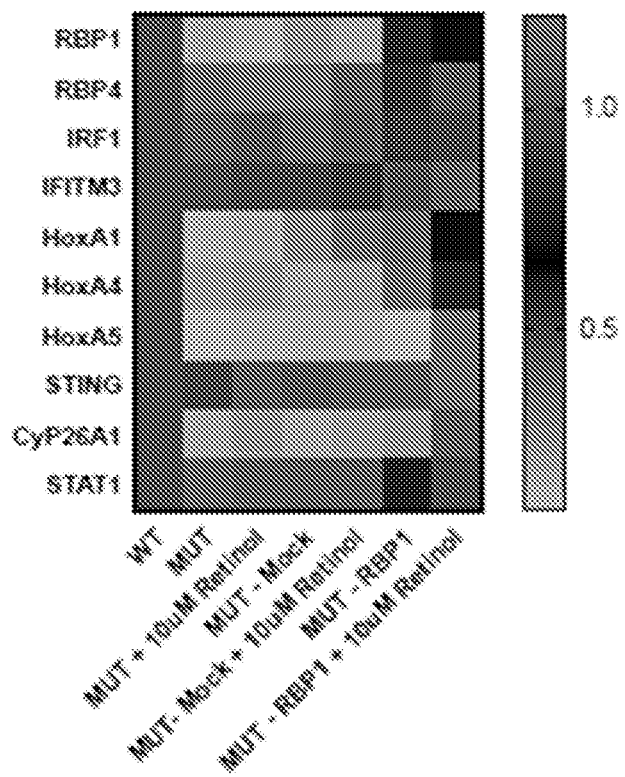
FIG. 8D is a heat map showing qPCR gene expression analysis of genes downstream of retinoid acid signaling. Results are representative of three independent experiments.

RBP1 overexpression reverses immune evasion in IDH mutant gliomas. To determine whether RBP1 overexpression would reverse the immune evasion observed in IDH mutant gliomas, IDH mutant glioma cells were transduced with RBP1 lentivirus (2 MOI). Cells were analyzed for NK cytotoxicity and gene expression of RA pathway genes. There was only a modest increase in NK cell cytotoxicity in RBP1-transduced cells. However, addition of 10 µM retinol to the cell culture medium of RBP1-transduced IDH mutant cells significantly increased recognition and killing by NK cells (FIG. 8A). Similarly, addition of retinol restored expression of NKG2D ligands (ULBP1, FIG. 8B; ULBP3, FIG. 8C) as well as RA pathway genes (FIG. 8D) to wild type expression levels.

Figure 9A:
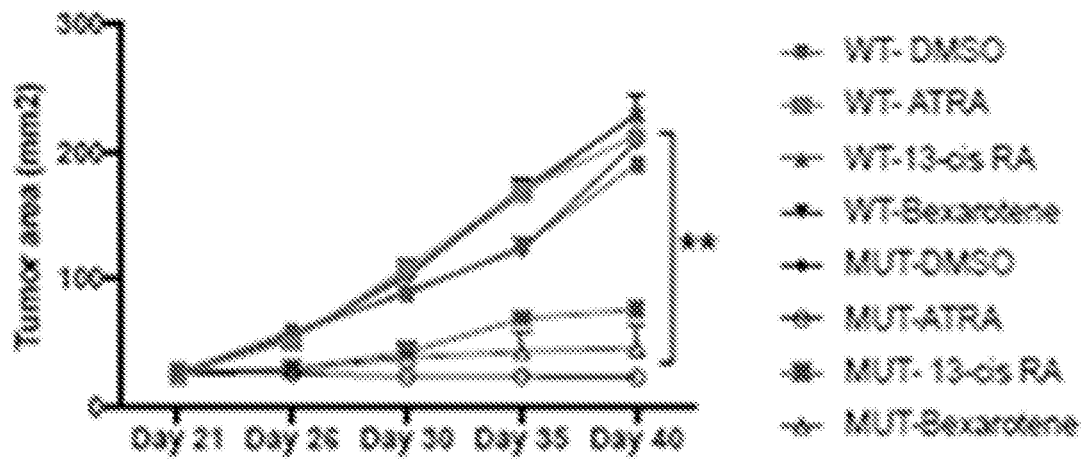
FIG. 9A is a graph showing tumor growth curves of IDH WT or mutant tumor-bearing mice treated with RA isoforms or DMSO. Expression of the NKG2D ligands ULBP1 (FIG. 9B), ULBP2 (FIG. 9C), ULBP3 (FIG. 9D) was analyzed ex vivo in mice treated with RA isoforms or DMSO, as indicated.
Figure 9B:
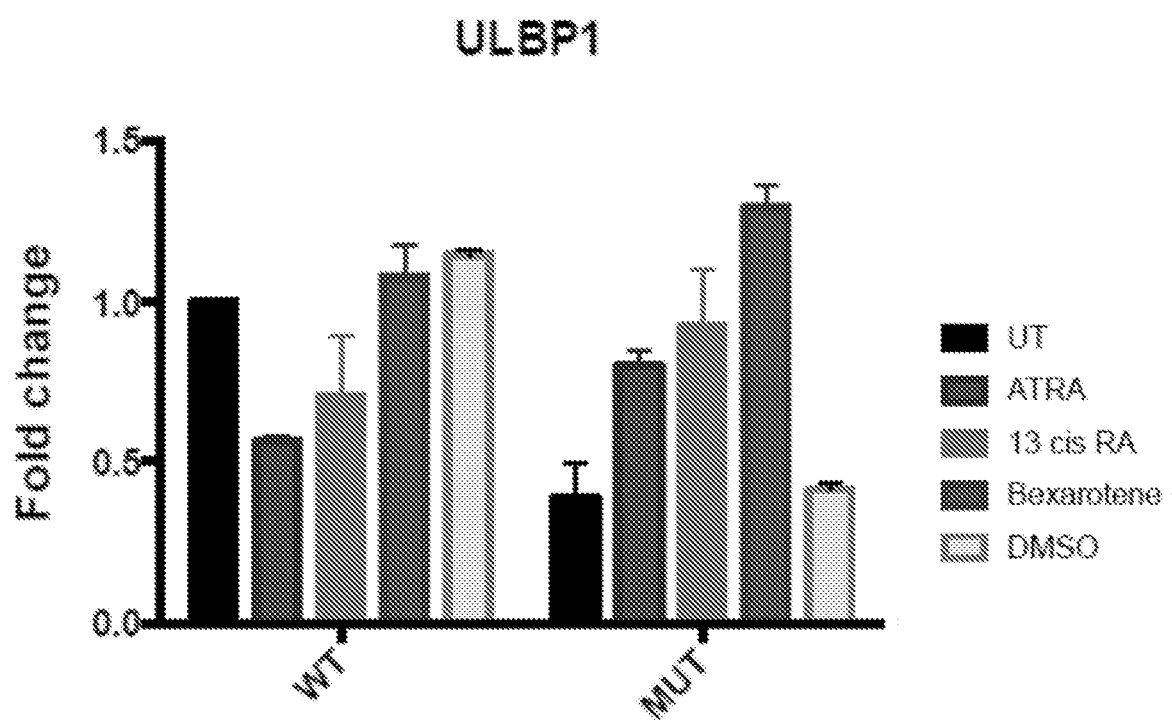
FIG. 9(A-J) shows ATRA is more effective at inducing tumor stasis in IDH mutant tumor-bearing mice compared to other RA isoforms.
FIG. 9E is a graph 15 showing the percent 7-AAD+ tumor cells after co-culture with human NKs, measured by flow cytometry. Infiltration of the immune cells NKs (FIG. 9F), macrophages (FIG. 9G), dendritic cells (DCs) (FIG. 9H), and monocytes (FIG. 9I) in IDH WT or mutant tumors treated with retinoid acid or DMSO by flow cytometry was quantified.
FIG. 9J shows percent monocytes in tumor-infiltrating lymphocytes (TILs) of IDH WT/IDH mutant tumor-bearing mice treated with ATRA, 13-cis retinoic acid or Bexarotene. DMSO was used as a vehicle.
Figure 9C:
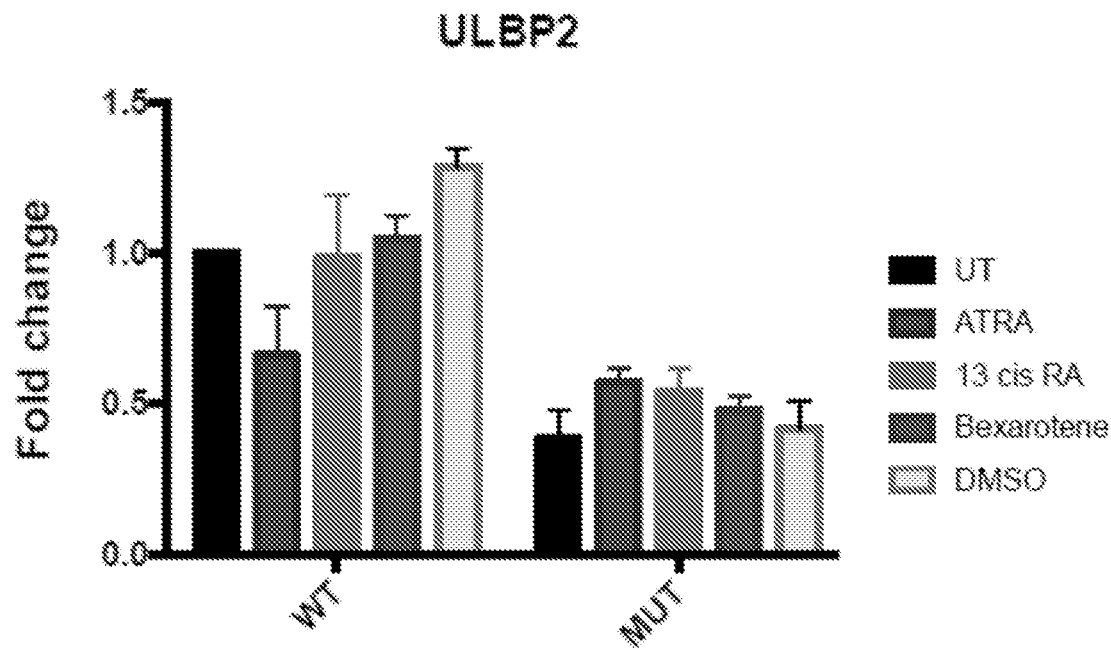
Figure 9D:
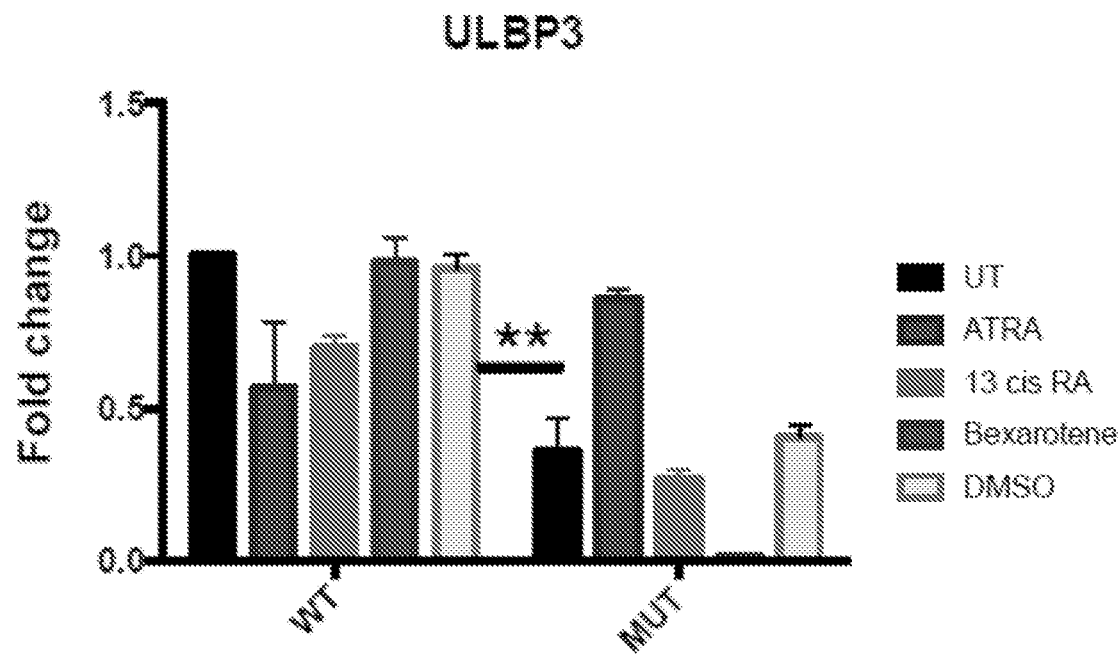
Figure 9E:
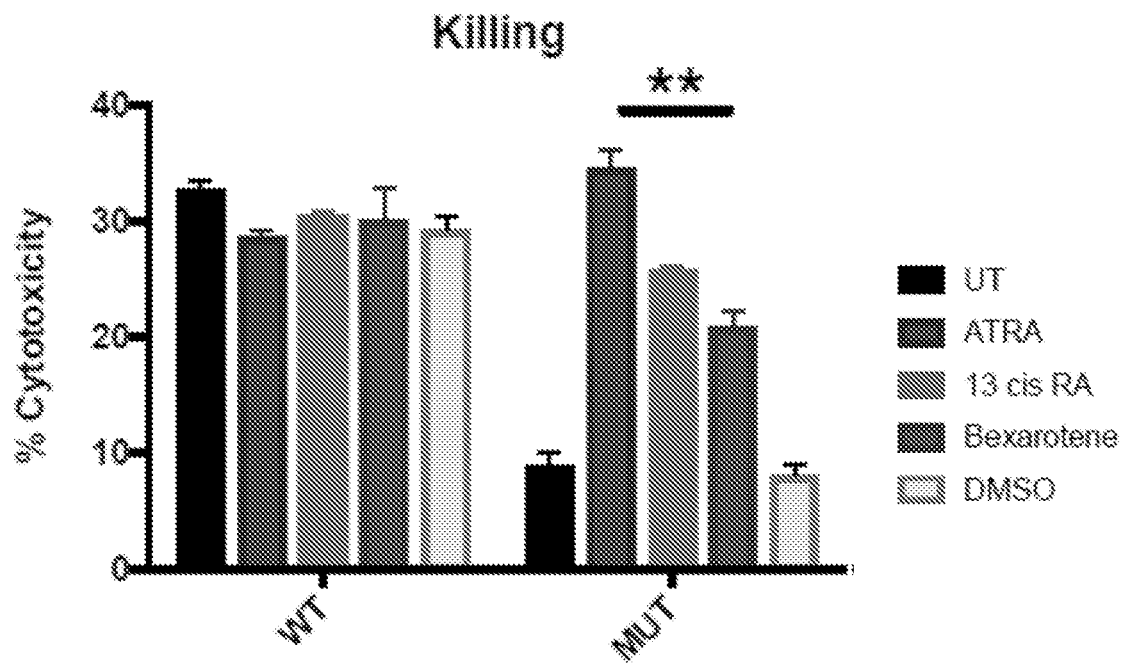
Figure 9F:
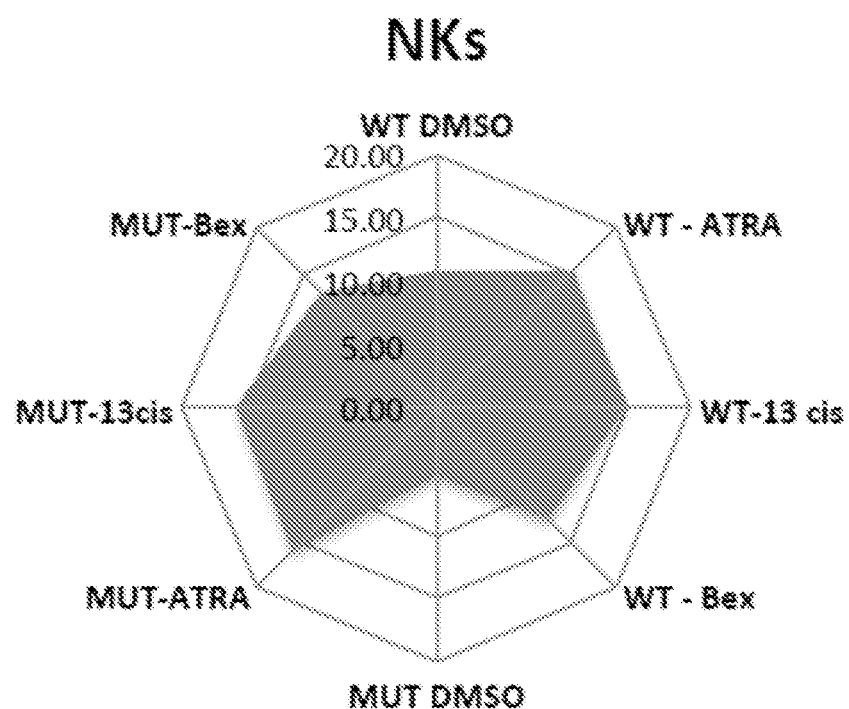
Figure 9G:
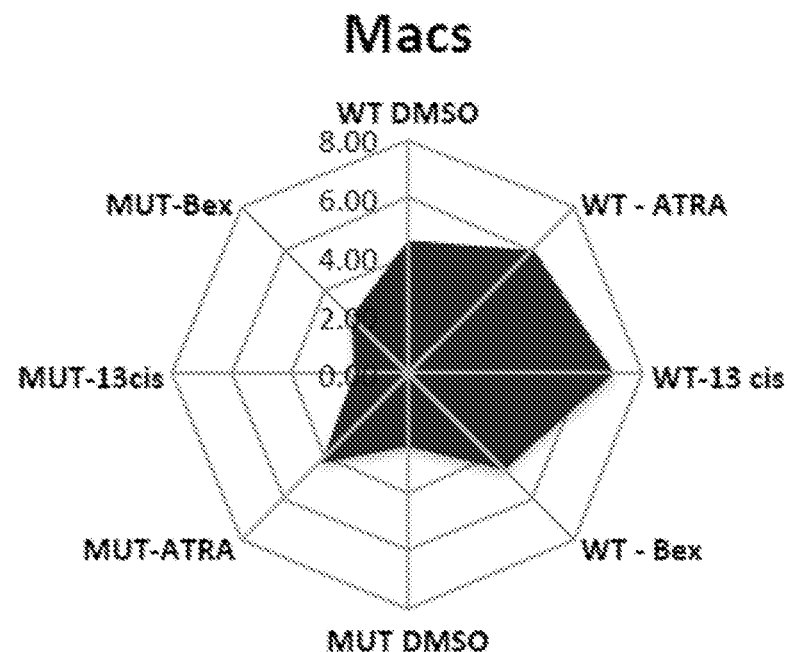
Figure 9H:
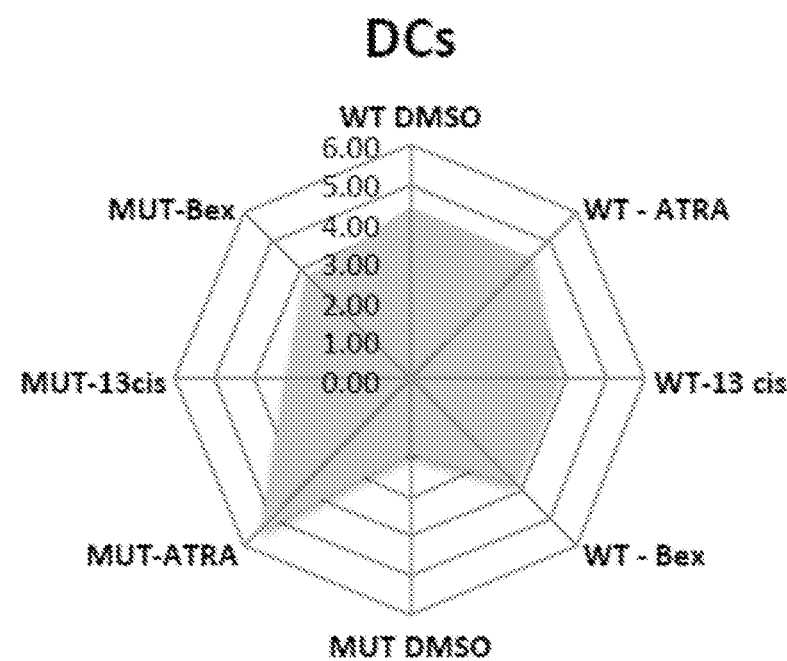
Figure 9I:
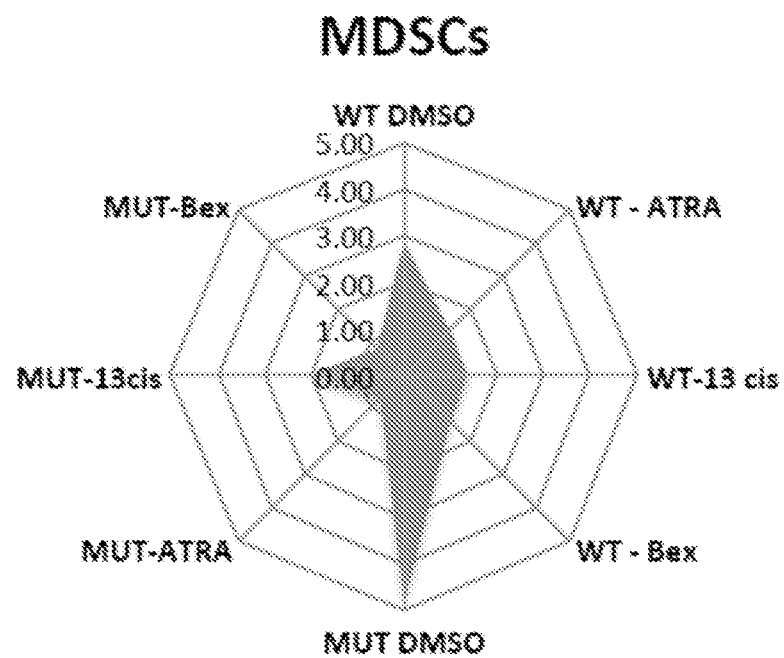
Figure 9J:
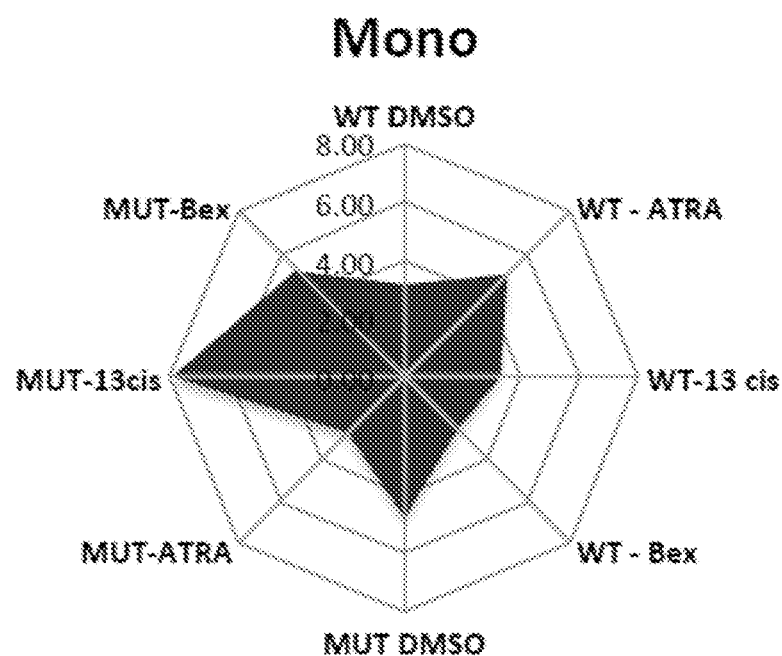
Figure 10A:
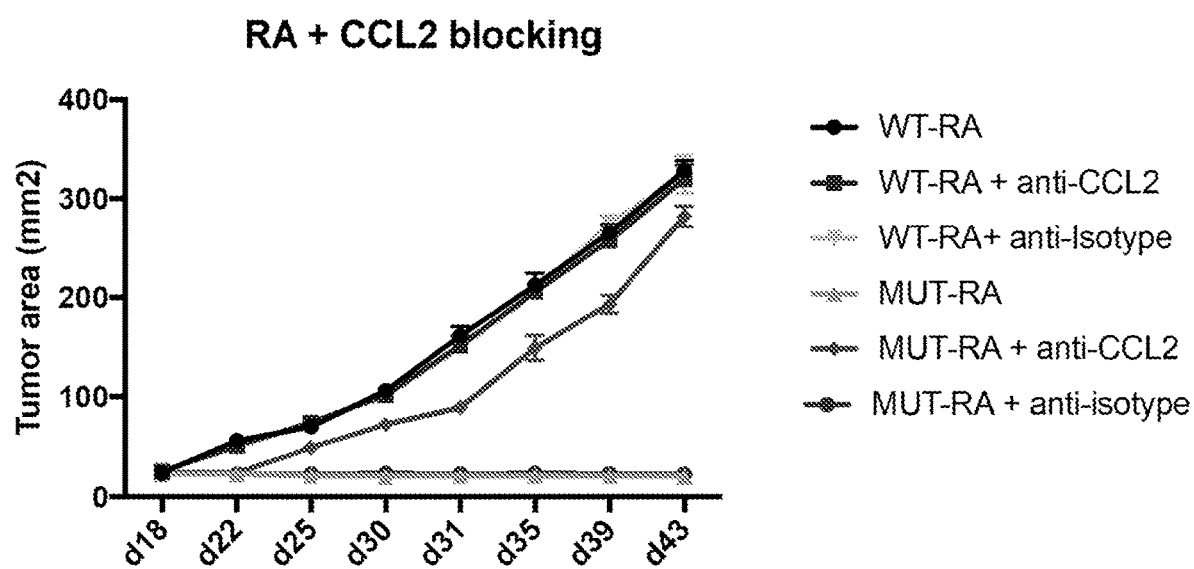
FIG. 10A shows tumor growth curves of IDH WT/MUT tumor-bearing mice treated with ATRA with/without CCL2 neutralization. Tumors were harvested at the end of the experiment shown in FIG. 10A and further analyzed for composition of infiltrating immune cells including NKs (FIG. 10B), M1 macrophages (FIG. 10C), monocytes (FIG. 10D), and MDSCs (FIG. 10E) in WT and mutant IDH tumors in the presence of DMSO control (circles), anti-CCL2 (diamonds), or anti-isotype (squares) treatment.
Figure 10B:
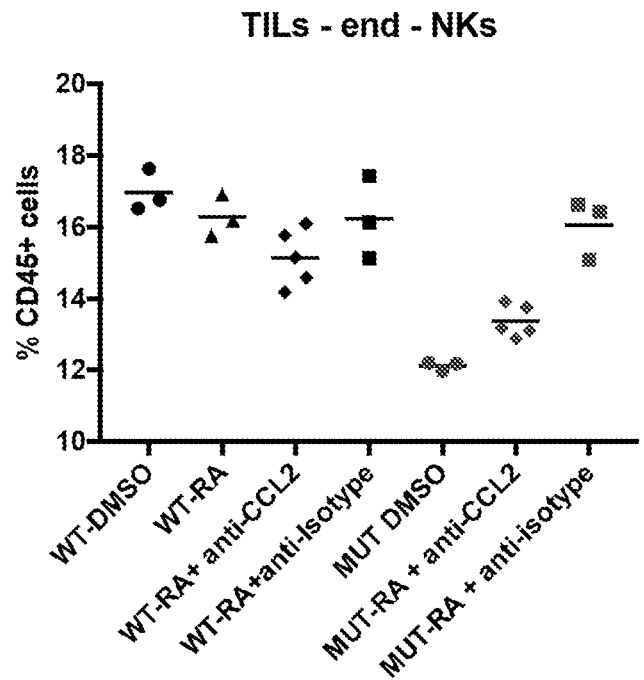
FIG. 10(A-E) are graphs showing CCL2 blockade reverses ATRA-mediated tumor stasis in a MDSCs and NK cell dependent manner.
Figure 10C:
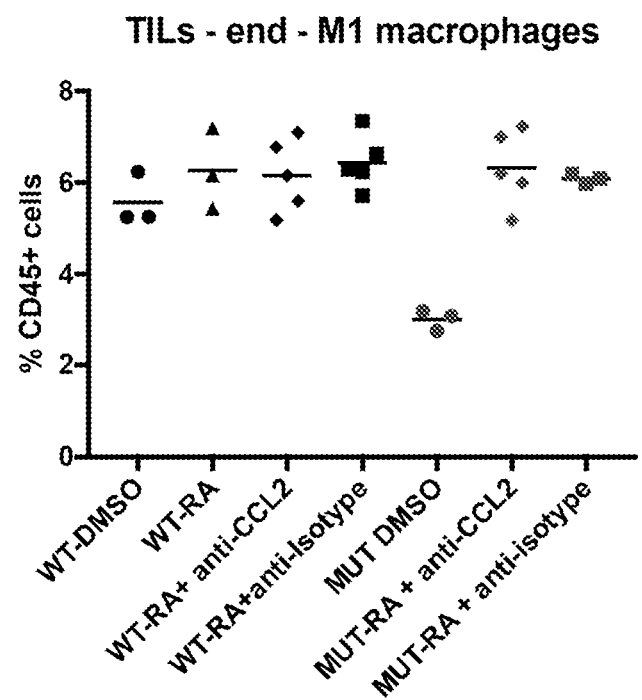
Figure 10D:
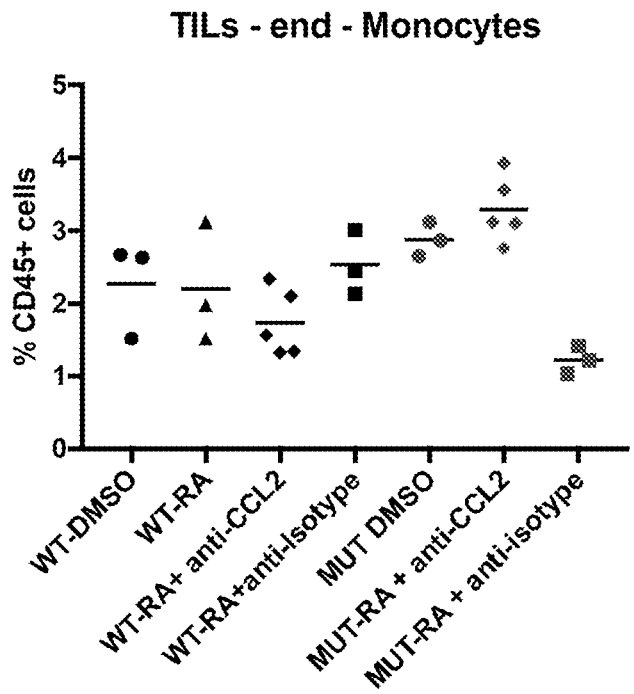
Figure 10E:
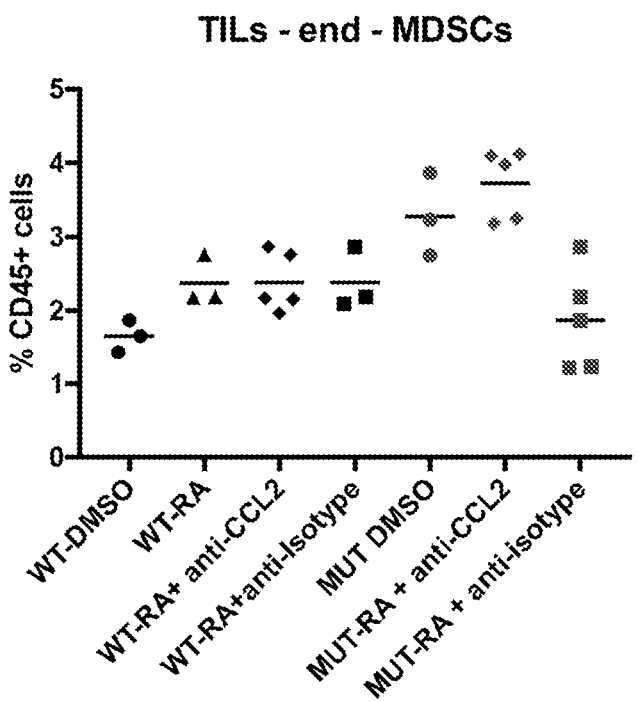

ATRA has superior anti-tumor efficacy compared to 13-cis RA and Bexarotene. There are multiple isoforms of RA that have demonstrated varying degrees of efficacy in clinical trials. Therefore, the efficacy of two other RA isoforms were compared with ATRA in IDH mutant gliomas. As shown in FIG. 9A, control (DMSA)-treated mutant tumors and all control and experimental-treated WT tumors increased in size over time (the top 5 data lines at Day 40 having endpoints at around 200 mm$^2$). However, treatment of IDH mutant tumors with all three retinoic acid isoforms reduced tumor size (the bottom 3 data lines at Day 40 having endpoints below 100 mm$^2$). Of these three RA isoforms, ATRA was the most effective. ATRA was significantly more effective at retarding IDH mutant tumor growth in vivo, compared with 13-cis RA and bexarotene (FIG. 9A). In addition, ATRA induced higher gene expression levels of ULBP3 compared with 13-cis RA and bexarotene (FIG. 9D), which correlated with significantly increased killing of IDH mutant cells by NK cells (FIG. 9E). The changes in tumor microenvironment induced by ATRA differed from the other RA isoforms as well. After ATRA treatment, the tumor microenvironment had lower MDSCs and monocytes, and higher DCs and macrophages compared with 13-cis RA and bexarotene (FIG. 9F through 9J).

Figure 13A:
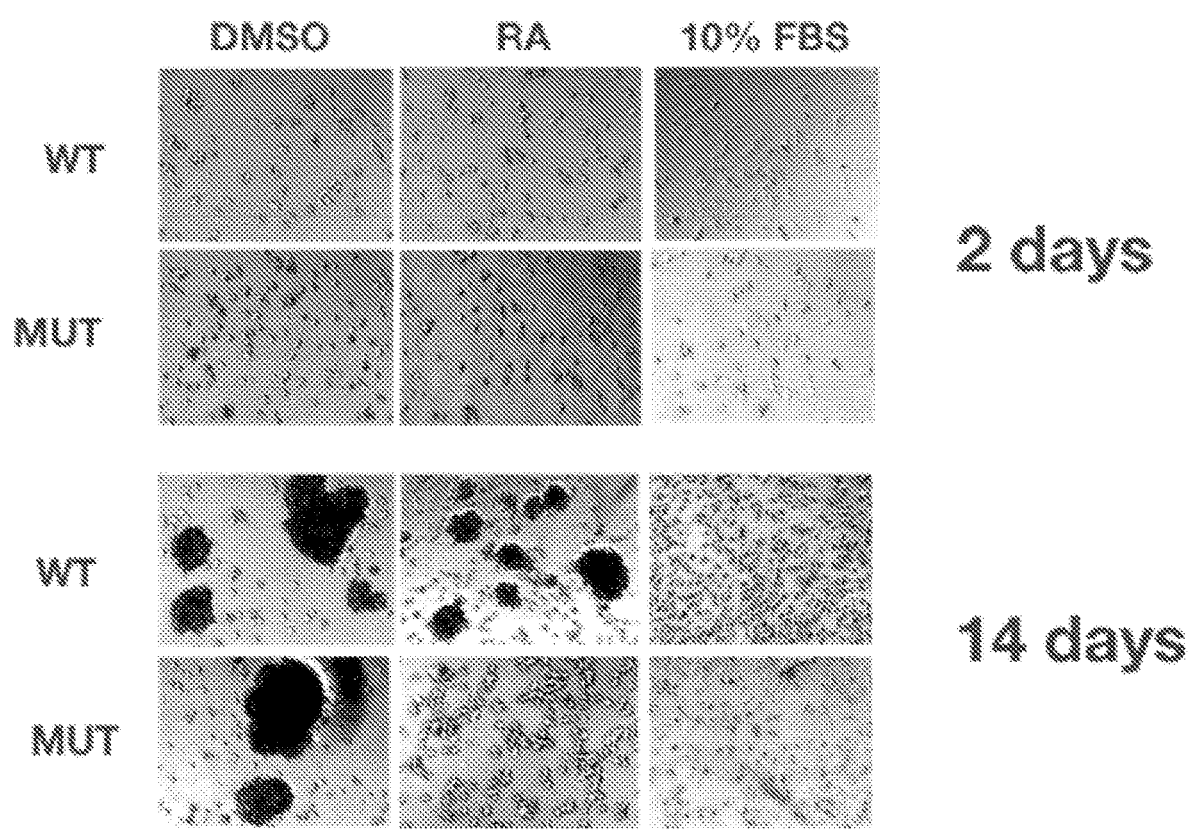
FIG. 13A shows cell morphology of ATRA treated (denoted as "RA") or control cells (WT and IDH Mut) after 2 days (top panels) and 14 days (bottom panels) after treatment. 10× magnification. Figures are representative of 6 independent fields of view.
Figure 13B:
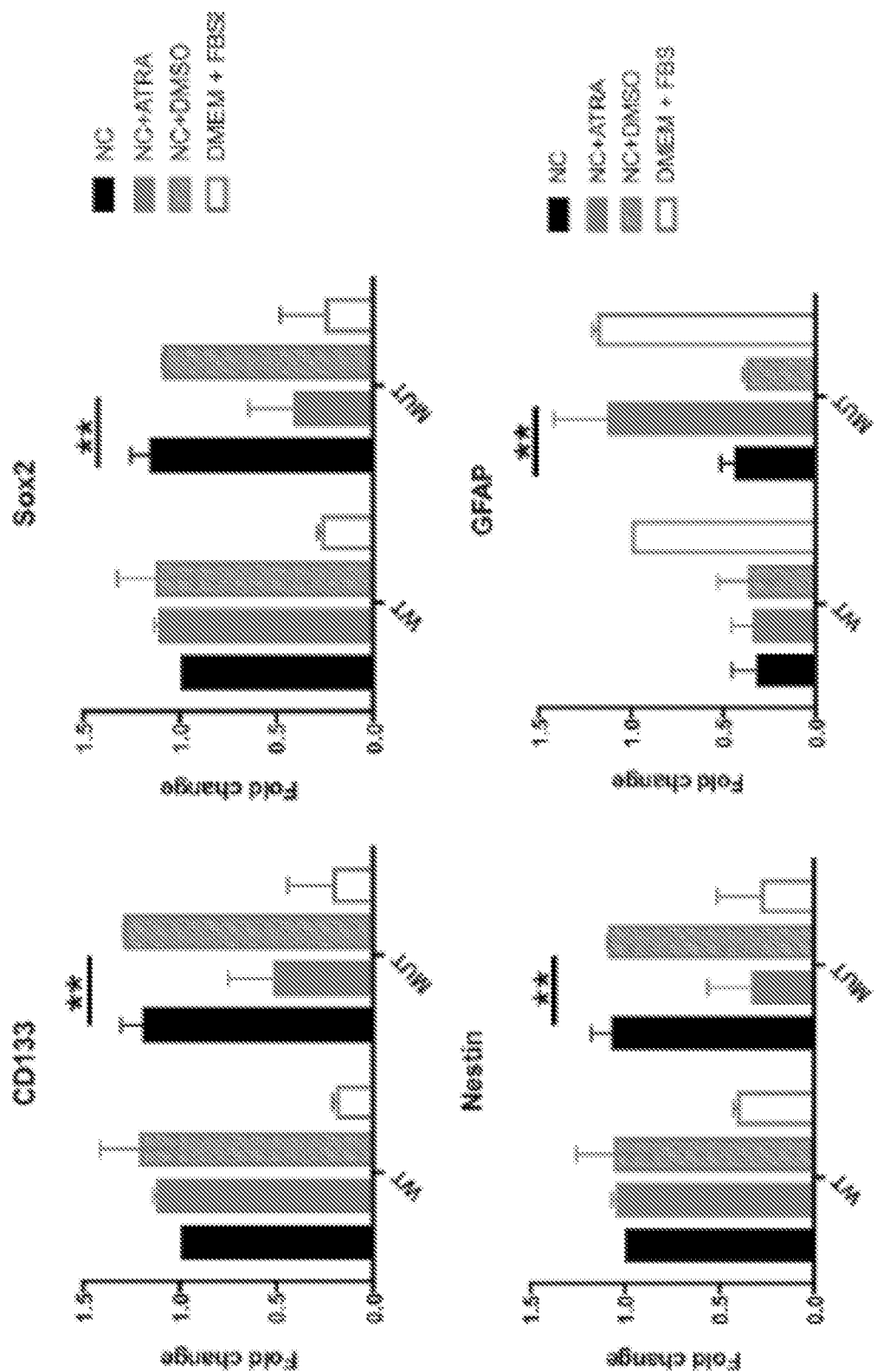
FIG. 13B shows gene expression of stem cell and differentiation markers (CD133, Sox2, Nestin, and GFAP) in IDH mutant and WT cells treated with 1 μM ATRA for 14 days.
Figure 13C:
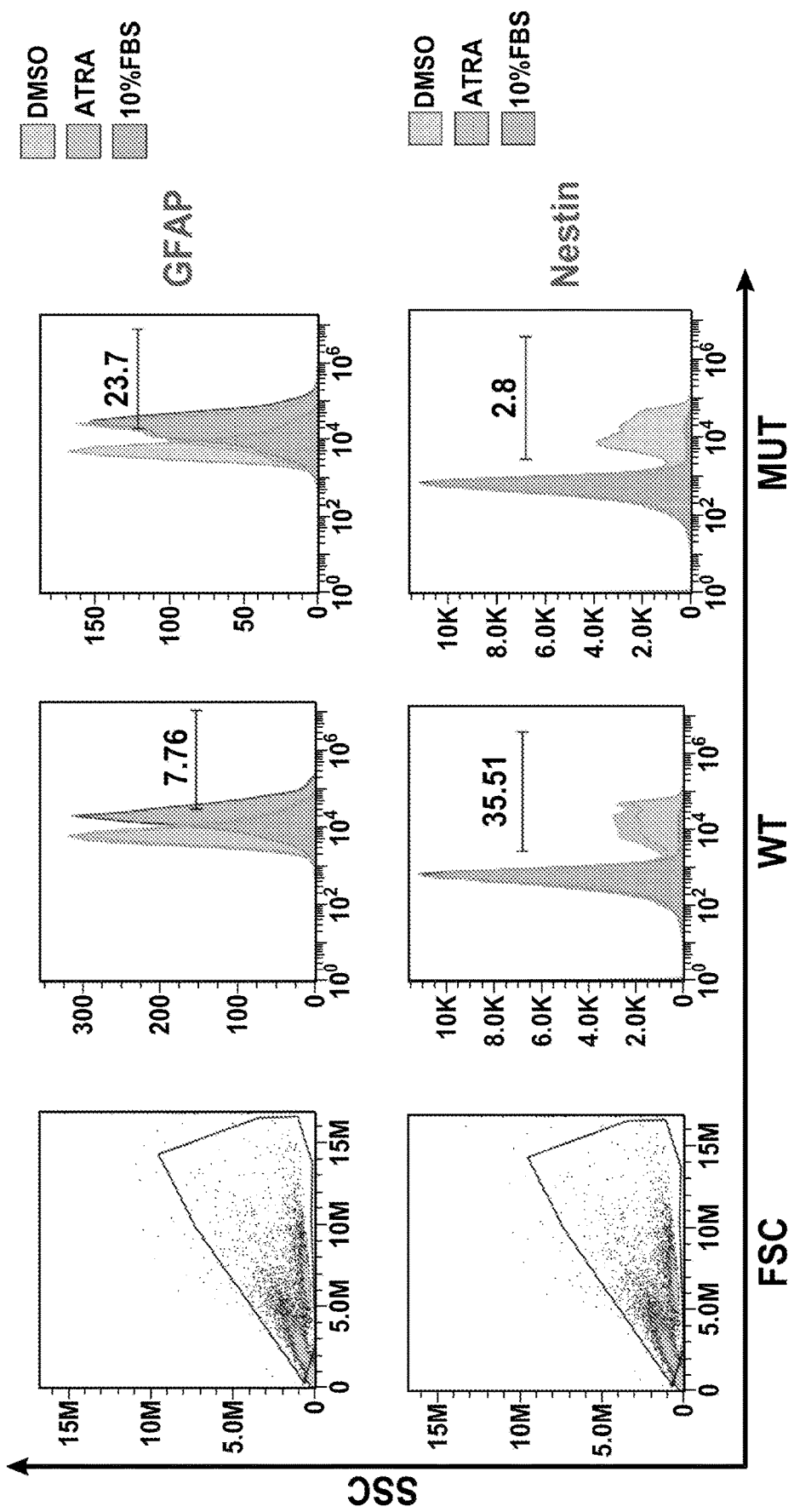
FIG. 13C shows flow cytometry analysis of ATRA or control-treated glioma stem cells for GFAP (top panels) and Nestin (bottom panels). Indicated numbers are % positive cells in ATRA-treated group.
Figure 13D:
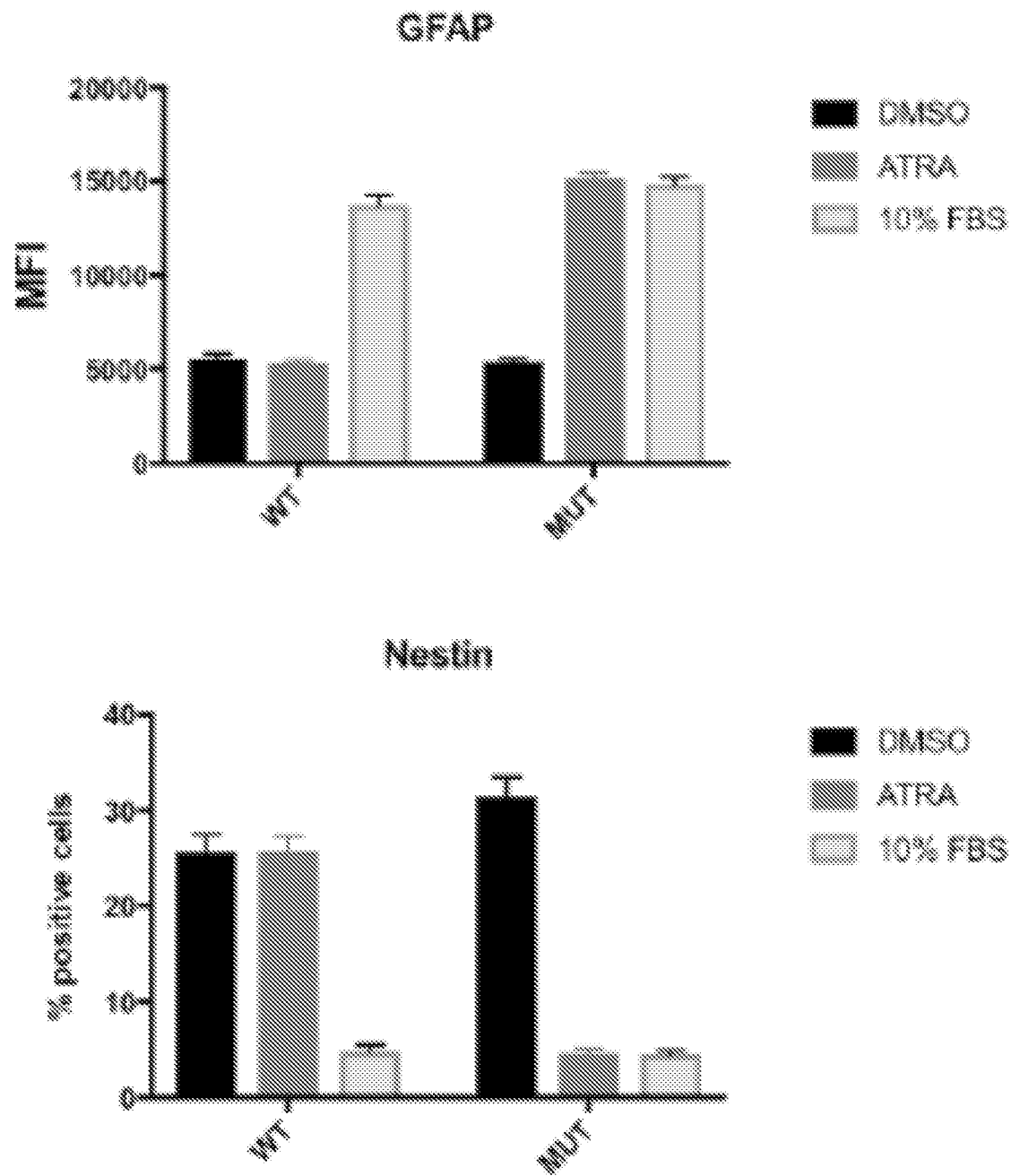
FIG. 13D shows a graphical representation of data presented in FIG. 13C for GFAP (top panel) and Nestin (bottom panel).

All-trans retinoic acid induces differentiation in IDH mutant glioma cells. All-trans retinoic acid (ATRA) is a differentiating agent for multiple types of cancers, including IDH mutant acute myeloid leukemia (AML). Therefore, efficacy of ATRA as a differentiating agent in IDH mutant gliomas was evaluated. IDH mutant or WT primary glioma neurospheres were treated with 1 µM ATRA for 2, 7 or 14 days. At each time point, cells were evaluated for morphological changes and changes in their molecular profile. Vehicle (DMSO)-treated cells served as controls, while cells treated with 10% FBS served as differentiation (positive) controls. ATRA induced morphological changes in IDH mutant primary glioma neurospheres, but not WT neurosphereres, after treatment for 14 days (FIG. 13A, bottom panels). Minimal morphological changes were observed at earlier time points (FIG. 13A, top panels). The expression levels of several stem cell and differentiation markers correlated with cell morphology. IDH mutant neurospheres treated with ATRA for 14 days demonstrated significantly lower levels of stem cell markers Sox2, CD133 and Nestin, and increased levels of GFAP, a astrocytic differentiation marker, by PCR (FIG. 13B), and by flow cytometry for Nestin and GFAP (FIGS. 13C and 13D). These significant changes were not observed at earlier time points (data not shown). In summary, ATRA induces differentiation in IDH mutant gliomas, albeit in a delayed manner.

Discussion

Mutation in the IDH1 or IDH2 genes occurs frequently in gliomas and other human malignancies. These mutations can impart the mutant IDH enzyme with a neomorphic activity—the ability to synthesize 2-hydroxyglutarate (2-HG), which leads to a reprogramming of the chromatin state, a block in differentiation, and the establishment of the glioma hypermethylator phenotype (G-CIMP). It has been hypothesized that the extensive DNA methylation that occurs in G-CIMP tumors maintains glioma cancer cells in a dedifferentiated state. The aberrant gene expression profile activated by mutant IDH1 blocks differentiation, causing the malignant expansion of tumor-initiating cells with capacity to self-renew. Apart from dedifferentiation, 2-HG also induces repression of multiple genes involved in immune response. Multiple studies have described immune evasion in IDH mutant tumors using a variety of mechanisms. For instance, IDH mutant tumors evade recognition and killing by NK cells by downregulating the expression of NKG2D ligands, especially ULBP3. In addition, IDH mutant tumor microenvironments are rich in immunosuppressive cell subsets such as monocytes, and significantly lack effector cells such as CD8+ T cells and NK cells.

To further understand mechanisms of immune evasion in IDH mutant gliomas, the genes most differentially down-regulated in IDH mutant tumors were analyzed. In an overall cohort of 198 patients, RBP1 was consistently hypermethylated in IDH1 or IDH2 MUT glioma tumors but not in WT tumors. Data disclosed herein and from The Cancer Genome Atlas (TCGA) database showed that RBP1 methylation is associated with decreased expression of CRBP1. Diagnostically, RBP1 methylation has also been established as a single biomarker for detecting both IDH1 and IDH2 mutations in gliomas. Studies in breast cancer cells have shown that silencing of RBP1 plays an important role in RA signaling by lowering all-trans-retinoic acid (ATRA) production and loss of retinoic acid receptor (RAR) levels, leading to loss of cell differentiation and tumor progression. This mechanism may help describe the molecular features of tumorigenesis in G-CIMP tumors.

ATRA is an active metabolite of vitamin A and mediates its biological effects by activating one or more of the closely related retinoic acid receptors (RARα, RARβ, and RARγ) that function as ligand-dependent transcriptional regulators. These receptors form heterodimers with retinoid receptors (RXRα, β, and γ) and bind to retinoid responsive response elements (RAREs) located in the promoter region of retinoid target genes to stimulate gene transcription. Thus, through receptor-mediated gene transcription, ATRA regulates a wide range of biological processes, including development, differentiation, proliferation, and apoptosis. In particular, the pro-differentiating effects of ATRA are documented in AML cell lines and primary patient samples. ATRA is also known to induce transcription of multiple immune genes, including STAT1 and type-1 interferons. IDH mutant gliomas have mechanisms to evade the immune system, including the down regulation of NKG2D ligands, especially ULBP1 and ULBP3 on IDH mutant cells in order to escape detection and killing by NK cells. Interestingly, ULBP1 and ULBP3 (also known as Retinoic acid early transcript 1 genes (RAET1) are induced by retinoic acid and interact with NKG2D receptors on NK and CD8+ T cells to trigger immune cell activation and tumor cell lysis. Anti-tumor effects of ATRA in IDH mutant gliomas were analyzed by sensitizing glioma cells to recognition and lysis by NK cells.

ATRA significantly increased the expression levels of NKG2D ligands ULBP1 and ULBP3 in vitro, while concomitantly increasing the killing of IDH mutant tumor cells by NK cells in an NKG2D-dependant manner (FIG. 2A through 2G). These effects occurred early on, after 48 hours of ATRA treatment. While the link between NKG2D ligands and ATRA has been established, this is the first reported use of ATRA to induce NKG2D ligand expression and NK killing in IDH mutant glioma cells. The ability of ATRA to induce differentiation in IDH mutant glioma stem cells was also evaluated. While ATRA induced differentiation in IDH mutant glioma stem cells, the effects were delayed, occurring after 10 days of ATRA treatment (FIG. 13A through 13D). The therapeutic efficacy of ATRA in IDH mutant gliomas in vivo was also evaluated. In both immunocompromised and immunocompetent mouse models, ATRA significantly slowed tumor growth in IDH mutant tumor-bearing mice, compared to untreated and WT tumor-bearing mice. This decline in tumor growth was accompanied by alteration of the IDH mutant tumor microenvironment to an inflammatory phenotype and increased recognition of ATRA-treated IDH mutant tumors by NK cells ex vivo (FIG. 3A through 3J). In fact, the effect of ATRA on IDH mutant gliomas in vivo depended on NK cells, since depletion of NK cells countered the anti-tumor effects of ATRA in vivo (FIG. 4A through 4F).

Microarray studies revealed that ATRA induced gene expression changes in IDH mutant cells. Interestingly, pathway analysis showed that immune cell chemotaxis was one of the most highly upregulated pathways in ATRA-treated IDH mutant cells (FIG. 5A through 5C). Analysis of chemotaxis pathway-associated genes showed that a high number of inflammatory chemokine genes were upregulated upon ATRA treatment. These findings validated in vivo observations in which ATRA changed the IDH mutant tumor microenvironment from an immune suppressive one (low NKs, high MDSCs) to an inflammatory one (high NKs, macrophages and DCs, low MDSCs) (FIG. 3A through 3J). The role of ATRA in immune cell chemotaxis has been debated and studied, with conflicting observations reported dependent upon the disease setting. In tumors, ATRA plays a role in priming an anti-tumor immune response. However, its role in mediating immune cell chemotaxis in the tumor microenvironment is still unclear.

Figure 6O:
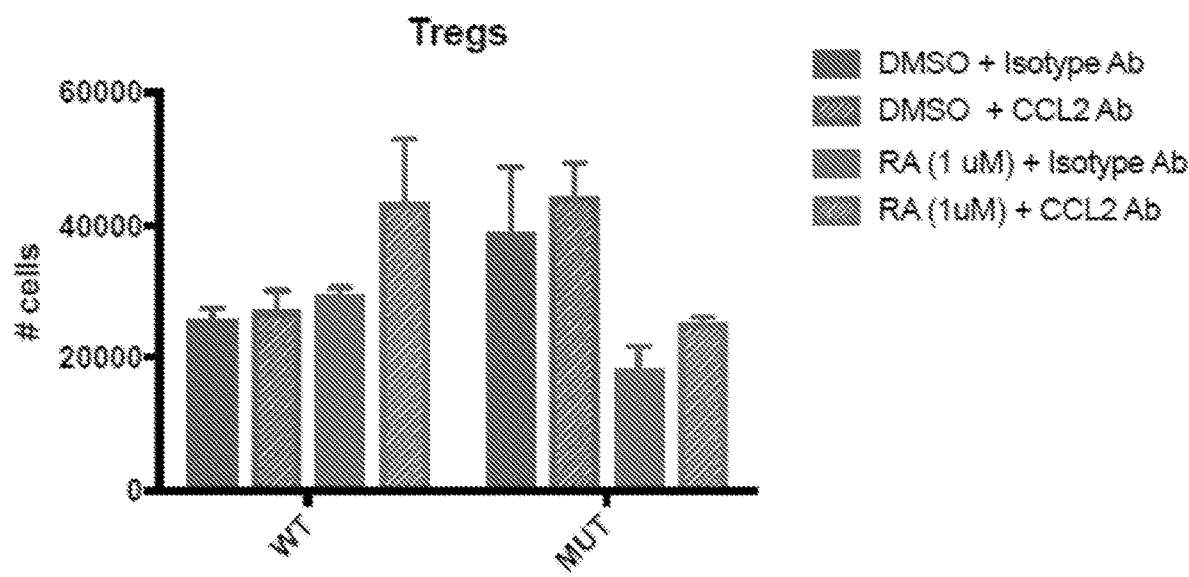

ATRA-induced chemotaxis of NK cells and macrophages was replicated in vitro in transwell assays. Therefore, to further dissect the mechanisms of ATRA-induced migration, a chemokine array was performed. The array revealed two significant changes to the chemokine profile of ATRA-treated IDH mutant cells: i) increased production of CCL2 and ii) decreased production of CXCL12 (FIG. 6A through 6O). Signals mediated by the chemokine CXCL12 and its receptor CXCR4 are involved in progression of cancer by enhancing tumor angiogenesis and immunosuppressive networks that regulate dissemination of peritoneal metastasis and development of cancer initiating cells (CICs). CXCL12 recruits suppressive CD11b+Gr1+ myeloid cells and pDCs at tumor sites, and induce intratumoral T regulatory cells (Tregs) localization, which impede immune mechanisms of tumor destruction. Therefore, the decreased CXCL12 production induced by ATRA contributes to propagating a pro-inflammatory and anti-tumorigenic microenvironment in IDH mutant tumors. CCL2, on the other hand, exerts both pro- and anti-tumor effects. CCL2 (also known as monocyte chemoattractant protein 1, MCP1) exerts potent chemotactic, stimulatory, and mitogenic effects on mononuclear cells. Elevated CCL2 expression levels in the tumor microenvironment are associated with poor prognosis in breast carcinoma patients. CCL2 also stimulates the migration of mammary carcinoma cell lines and to mediate the recruitment of specific monocyte populations that support the establishment of metastatic disease. However, CCL2 may also act to attract antitumor immune cells and is required for efficient immunosurveillance, implying that the inhibition of CCL2 may promote neocarcinogenesis as well as the development of metastases. Specifically, CCL2 has also been correlated with increased migration of activated NKs and T cells. This dichotomy is possibly due to differential signaling occurring through different isoforms of CCR2, the ligand for CCL2. ATRA increases the expression and production of specific chemokines in vitro and in vivo, directly mediated by ligand-activated retinoic acid receptors. CCL2 is an ATRA target gene and ATRA-induced CCL2 production has been documented.

The efficacy of ATRA in reversing the immune evasive phenotype in IDH mutant gliomas was remarkable. It was hypothesized that the retinoic acid deficiency in IDH mutant gliomas was due to down regulation of RBP1 in those cells. To confirm this hypothesis, it was evaluated whether RBP1 down regulation was necessary and sufficient for the immune evasive characteristics of IDH mutant cells. RBP1 gene expression was silenced in IDH wild-type cells using siRNA transfection. RBP1-silenced cells significantly down regulated the expression of RBP1, as well as NKG2D ligands, reflected by the decreased recognition and killing by NK cells. Thus, like IDH mutant cells, RBP1-silenced IDH wild type cells escaped recognition and NK killing. Even in terms of gene expression levels of genes downstream of ATRA signaling, RBP1-silenced IDH wild type cells resembled IDH mutant cells (FIG. 7A through 7F). To test sufficiency, RBP1 expression was induced in IDH mutant cells. Interestingly, RBP1 gene transduction was only able to partially restore NK-mediated killing in IDH mutant cells. It was hypothesized that even though RBP1 gene expression and activity was restored, there was insufficient Vitamin A (retinol) substrate in the medium, leading to decreased RA production by these cells. Indeed, Retinol treatment increased killing of RBP1-transduced IDH mutant cells by NK cells, in addition to restoring gene expression of relevant genes to IDH wild type levels (FIG. 8A through 8D). Thus, RBP1 plays a central role in the development of the immune evasive phenotype observed in IDH mutant gliomas.

Retinoic acid has been used as a chemotherapeutic agent in a wide variety of cancers, in pre-clinical as well as clinical applications. 13-cis-RA is the most common form of RA used in clinics, and is effective in a variety of neoplasms. Therefore, the efficacy of 13-cis RA was compared with ATRA and Bexarotene (a synthetic retinoic acid analogue) in IDH mutant gliomas. ATRA was the most effective RA isoform in terms of tumor growth, although the differences between the three groups were not significant. The difference between the three isoforms, however, lay in the biology. There were significant differences in the induction of NKG2D ligand expression between ATRA, 13-cis RA and bexarotene. Importantly, ATRA induced the highest level of NK-mediated killing in IDH mutant cells (FIG. 9A through 9K). Higher levels of toxicity in 13-cis RA and Bexarotene were also observed for treated mice (weight loss and wasting) that were not observed in ATRA-treated mice. Thus, overall, for IDH mutant gliomas, ATRA is a superior choice of RA isoform based on anti-tumor efficacy, induction of NK killing, and lower toxicity.

The disparate effects of ATRA dysregulation on the immunogenicity of IDH mutant cells are disclosed herein. In IDH mutant tumors, ATRA treatment induced immune-related responses such as increased expression of type-1 immune response genes and NKG2D ligands. ATRA also increased the chemotaxis of inflammatory immune cells towards IDH mutant gliomas, in a CCL2-dependant manner. As compared to other RA isoforms currently used, ATRA was superior. Overall, disclosed herein is a novel role for ATRA as an immune adjuvant capable of reducing or reversing the immune evasive properties of IDH mutant gliomas.

EXAMPLE 2

Involvement of CCL2 in RA-Mediated Tumor Growth Stasis

IDH WT and MUT (IDH1 R132H) tumor-bearing mice were treated with 10 mg/kg ATRA every alternate day starting on day 18 after tumor inoculation. Mice were also injected with 1 μg anti-CCL2 neutralizing antibody (or anti isotype antibody) on the 1st day of ATRA treatment. CCL2 blockade reversed ATRA-mediated tumor stasis in a MDSCs and NK cell dependent manner (FIG. 10A-E).

EXAMPLE 3

RA Treatment in Chondrosarcoma IDH Mutant

Figure 11C:
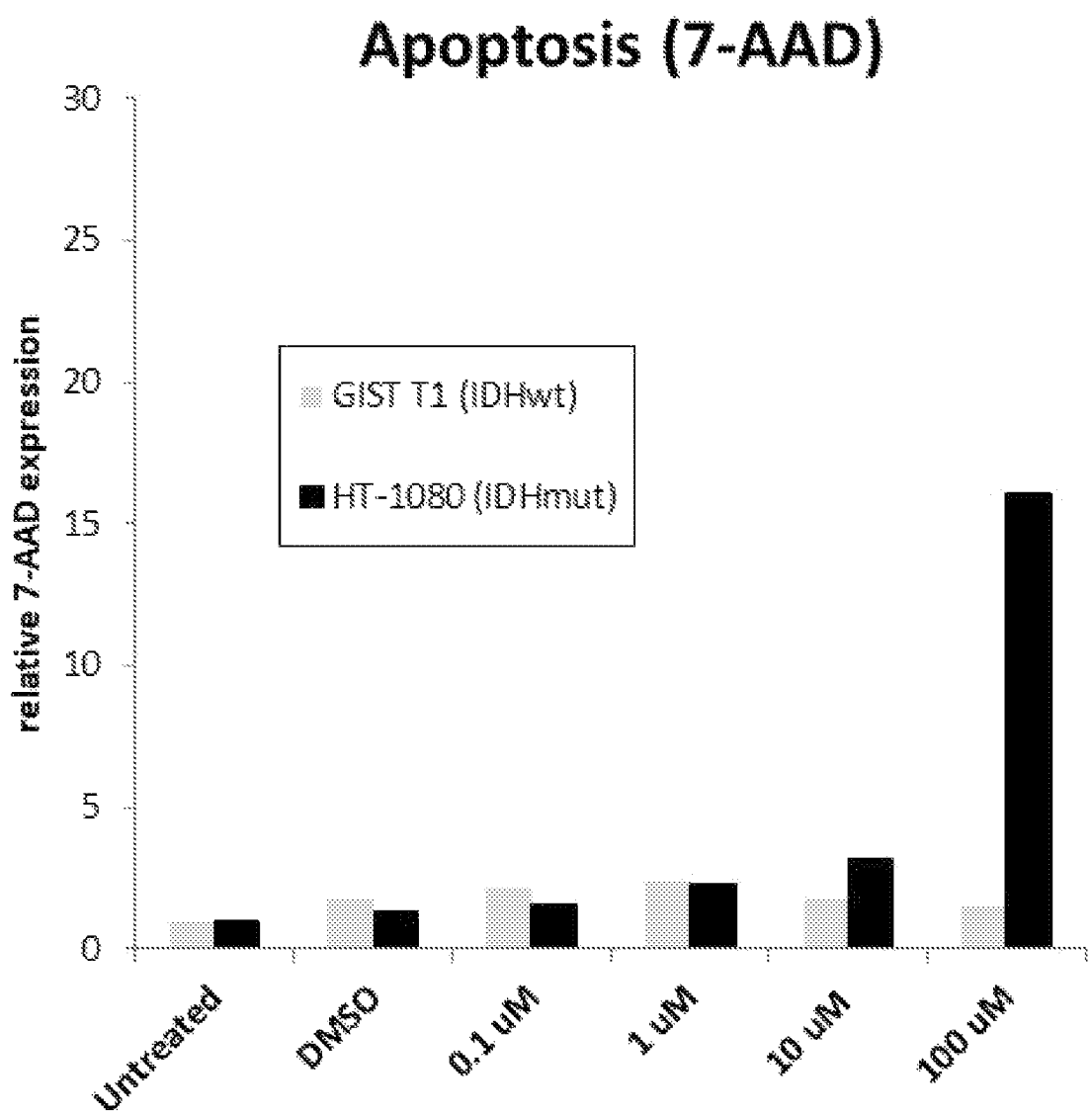
FIG. 11(A-F) are graphs showing ATRA induces cell death, up-regulation of NKG2D ligands, and NK-induced killing in IDH mutant chondrosarcomas. IDH mutant (HT-1080) chondrosarcoma cells were treated with different doses of ATRA or DMSO for 48 hours. After treatment, cells were evaluated for viability (FIG. 11A) and apoptosis by caspase activity (FIG. 11B). Additionally, IDH WT cells (GIST T1, grey bars) and IDH mutant (HT-1080, black bars) chondrosarcoma cells were treated with different doses of ATRA or DMSO for 48 hours. 7-AAD levels corresponding to apoptosis were detected by flow cytometry (FIG. 11C).
FIG. 11D shows RBP1 levels determined by qPCR in IDH WT (GIST 48) and IDH mutant (HT-1080) chondrosarcoma cells.
FIG. 11E shows RBP1 levels determined by qPCR in IDH mutant (HT-1080) cells after treatment with 1 µM or 10 µM ATRA for 48 hours. IDH WT cells (GIST-T1), and IDH mutant chondrosarcoma cells (HT-1080 and SW 1353) were treated with different doses of ATRA or DMSO for 48 hours and were evaluated for killing by NK cells (FIG. 11F). The graph in FIG. 11F shows percent cytotoxicity on untreated IDH WT cells (White bar) vs untreated and treated IDH mutant HT-1080 (black bars) or mutant SW 1353 (gray bars) chondrosarcoma cells.

IDH mutant (HT-1080, R132C IDH1 mutation) chondrosarcoma cells were treated with different doses of ATRA or DMSO for 48 hours. After treatment, cells were evaluated for viability (FIG. 11A) and apoptosis by caspase activity (FIG. 11B). ATRA decreased cell viability and induced apoptotic cell death in IDH mutant chondrosarcomas. Additionally, IDH WT cells and IDH mutant chondrosarcoma cells were treated with different doses of ATRA or DMSO for 48 hours. ATRA treatment increased 7-AAD levels corresponding to increased apoptotic cell death in a dose-dependent manner (FIG. 11C).

IDH mutant tumor cells produce reduced amounts of RBP1 compared to WT IDH tumor cells (FIG. 11D). 1 μM or 10 μM ATRA treatment for 48 hours increased RBP1 levels in IDH mutant chondrosarcoma cells in a dose dependent manner (FIG. 11E). These results show that increasing amounts of ATRA can concomitantly increase the levels of RBP1 in IDH mutant tumor cells.

Figure 11F:
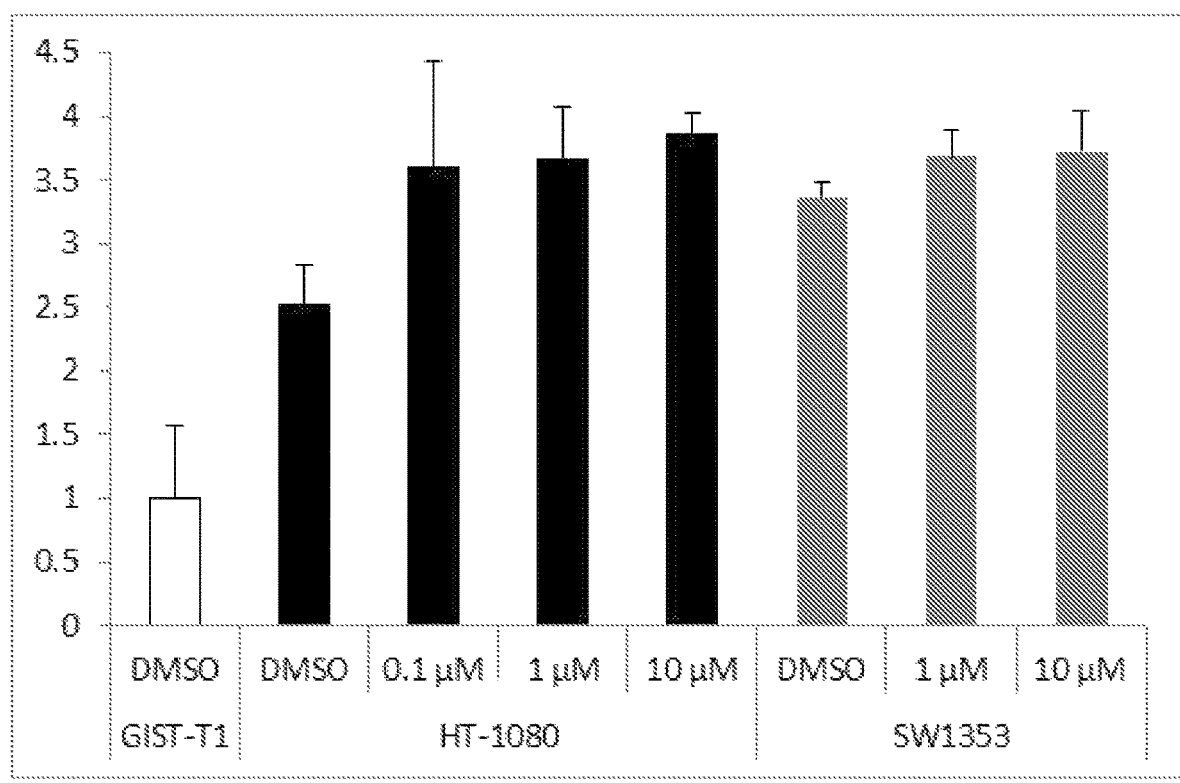

IDH WT chondrosarcoma cells and IDH mutant chondrosarcoma cells were treated with different doses of ATRA or DMSO for 48 hours and were evaluated for killing by NK cells (FIG. 11F). NK cytotoxicity on IDH WT chondrosarcoma cells and IDH mutant chondrosarcoma cells was evaluated. ATRA treatments increased NK-mediated cell killing of IDH mutant chondrosarcoma cells in at least two chondrosarcoma cell lines.

EXAMPLE 4

RA Therapy in a Human Patient with IDH Mutant Glioma

Figure 12A:
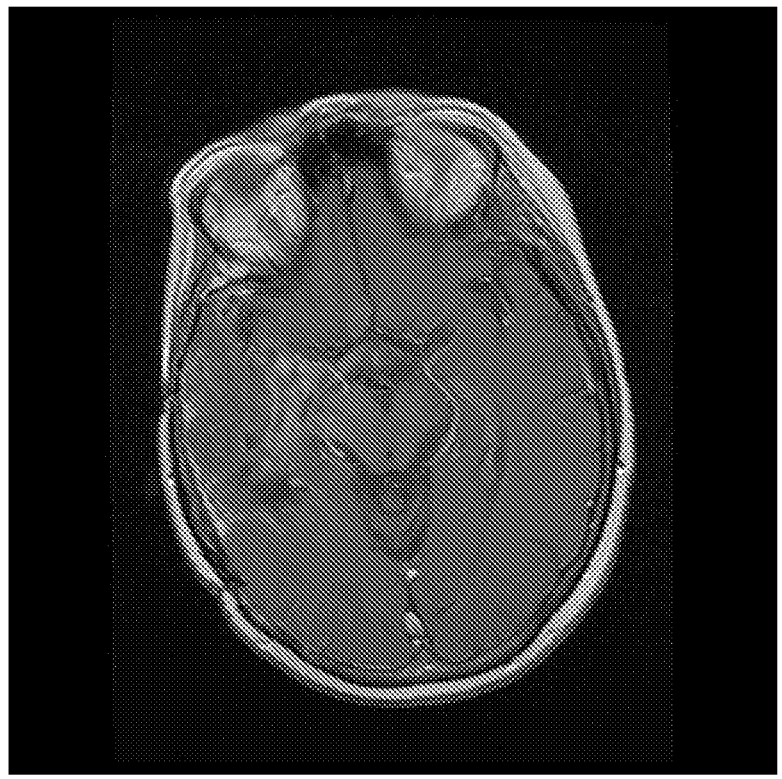
FIG. 12(A-B) are images of MRI brain scans. A 44-year old patient with diffuse IDH mutant glioma was treated with 40 mg/m$^2$ ATRA for three months on a treatment cycle of 21 days on, 7 days off. MRI was performed before (FIG. 12A) and after (FIG. 12B) ATRA treatment.
Figure 12B:

A 44-year old female patient with diffuse IDH mutant glioma was treated with 40 mg/m2 ATRA on a treatment cycle of 21 days on, 7 days off. MRI images of the patient's brain were performed before (FIG. 12A) and after (FIG. 12B) ATRA treatment. Results showed a reduction in the size and severity of the glioma tumor.

EXAMPLE 5

Sequences

```
An IDH1 polynucleotide
                                                             SEQ ID NO: 1
   1    gggctgagga ggcggggcct gggagggggac aaagccggga agaggaaaag ctcggaccta
  61    ccctgtggtc ccgggtttct gcagagtcta cttcagaagc ggaggcactg ggagtccggt
 121    ttgggattgc caggctgtgg ttgtgagtct gagcttgtga gcggctgtgg cgccccaact
 181    cttcgccagc atatcatccc ggcaggcgat aaactacatt cagttgagtc tgcaagactg
 241    ggaggaactg gggtgataag aaatctattc actgtcaagg tttattgaag tcaaaatgtc
 301    caaaaaaatc agtggcggtt ctgtggtaga gatgcaagga gatgaaatga cacgaatcat
 361    ttgggaattg attaaagaga aactcatttt tccctacgtg gaattggatc tacatagcta
 421    tgatttaggc atagagaatc gtgatgccac caacgaccaa gtcaccaagg atgctgcaga
 481    agctataaag aagcataatg ttggcgtcaa atgtgccact atcactcctg atgagaagag
 541    ggttgaggag ttcaagttga aacaaatgtg gaaatcacca aatggcacca tacgaaatat
 601    tctgggtggc acggtcttca gagaagccat tatctgcaaa aatatccccc ggcttgtgag
 661    tggatgggta aaacctatca tcataggtcg tcatgcttat ggggatcaat acagagcaac
 721    tgattttgtt gttcctgggc ctggaaaagt agagataacc tacacaccaa gtgacggaac
 781    ccaaaaggtg acatacctgg tacataactt tgaagaaggt ggtggtgttg ccatggggat
 841    gtataatcaa gataagtcaa ttgaagattt tgcacacagt ccttccaaa tggctctgtc
 901    taagggttgg ccttttgtatc tgagcaccaa aaacactatt ctgaagaaat atgatgggcg
 961    ttttaaagac atctttcagg agatatatga caagcagtac aagtcccagt ttgaagctca
1021    aaagatctgg tatgagcata ggctcatcga cgacatggtg gcccaagcta tgaaatcaga
1081    gggaggcttc atctgggcct gtaaaaacta tgatggtgac gtgcagtcgg actctgtggc
1141    ccaagggtat ggctctctcg gcatgatgac cagcgtgctg gtttgtccag atggcaagac
1201    agtagaagca gaggctgccc acgggactgt aacccgtcac taccgcatgt accagaaagg
1261    acaggagacg tccaccaatc ccattgcttc cattttttgcc tggaccagag ggttagccca
1321    cagagcaaag cttgataaca ataaagagct tgccttcttt gcaaatgctt tggaagaagt
1381    ctctattgag acaattgagg ctggcttcat gaccaaggac ttggctgctt gcattaaagg
1441    tttacccaat gtgcaacgtt ctgactactt gaatacattt gagttcatgg ataaacttgg
1501    agaaaacttg aagatcaaac tagctcaggc caaactttaa gttcatacct gagctaagaa
1561    ggataattgt cttttggtaa ctaggtctac aggtttacat ttttctgtgt tacactcaag
1621    gataaaggca aaatcaattt tgtaatttgt ttagaagcca gagtttatct tttctataag
1681    tttacagcct ttttcttata tatacagtta ttgccacctt tgtgaacatg gcaagggact
```

-continued

```
1741  ttttacaat  tttattta    ttttctagta  ccagcctagg  aattcggtta  gtactcattt
1801  gtattcactg  tcactttttc  tcatgttcta  attataaatg  accaaaatca  agattgctca
1861  aaagggtaaa  tgatagccac  agtattgctc  cctaaaatat  gcataaagta  gaaattcact
1921  gccttcccct  cctgtccatg  accttgggca  cagggaagtt  ctggtgtcat  agatatcccg
1981  ttttgtgagg  tagagctgtg  cattaaactt  gcacatgact  ggaacgaagt  atgagtgcaa
2041  ctcaaatgtg  ttgaagatac  tgcagtcatt  tttgtaaaga  ccttgctgaa  tgtttccaat
2101  agactaaata  ctgtttaggc  cgcaggagag  tttggaatcc  ggaataaata  ctacctggag
2161  gtttgtcctc  tccatttttc  tctttctcct  cctggcctgg  cctgaatatt  atactactct
2221  aaatagcata  tttcatccaa  gtgcaataat  gtaagctgaa  tctttttttgg  acttctgctg
2281  gcctgttta   tttctttat   ataaatgtga  tttctcagaa  attgatatta  aacactatct
2341  tatcttctcc  tgaactgttg  attttaatta  aaattaagtg  ctaattacca  ttaaaaaaaa
2401  aa
```

An IDH2 polynucleotide
SEQ ID NO: 2
```
   1  attttgcaac  gccataggct  tccagcgact  gctggtgatg  tttctgatgc  cgacaaaagg
  61  atcaaggtgg  cgaagcccgt  ggtggagatg  gatggtgatg  agatgacccg  tattatctgg
 121  cagttcatca  aggagaagct  catcctgccc  cacgtggaca  tccagctaaa  gtattttgac
 181  ctcgggctcc  caaaccgtga  ccagactgat  gaccaggtca  ccattgactc  tgcactggcc
 241  acccagaagt  acagtgtggc  tgtcaagtgt  gccaccatca  ccctgatga   ggcccgtgtg
 301  gaagagttca  agctgaagaa  gatgtggaaa  agtcccaatg  gaactatccg  gaacatcctg
 361  gggggggactg  tcttccggga  gcccatcatc  tgcaaaaaca  tcccacgcct  agtccctggc
 421  tggaccaagc  ccatcaccat  tggcaggcac  gcccatggcg  accagtacaa  ggcacagac
 481  tttgtggcag  accgggccgg  cacttttcaaa  atggtcttca  ccccaaaaga  tggcagtggt
 541  gtcaaggagt  gggaagtgta  caacttcccc  gcaggcggcg  tgggcatggg  catgtacaac
 601  accgacgagt  ccatctcagg  ttttgcgcac  agctgcttcc  agtatgccat  ccagaagaaa
 661  tggcccgctgt  acatgagcac  caagaacacc  atactgaaag  cctacgatgg  gcgtttcaag
 721  gacatcttcc  aggagatctt  tgacaagcac  tataagaccg  acttcgacaa  gaataagatc
 781  tggtatgagc  accggctcat  tgatgacatg  gtggctcagg  tcctcaagtc  ttcgggtggc
 841  tttgtgtggg  cctgcaagaa  ctatgacgga  gatgtgcagt  cagacatcct  ggcccaggc
 901  tttggctccc  ttggcctgat  gacgtccgtc  ctggtctgcc  ctgatgggaa  gacgattgag
 961  gctgaggccg  ctcatgggac  cgtcacccgc  cactatcggg  agcaccagaa  gggccggccc
1021  accagcacca  accccatcgc  cagcatctt   gcctgacac   gtggcctgga  gcaccggggg
1081  aagctggatg  ggaaccaaga  cctcatcagg  tttgcccaga  tgctggagaa  ggtgtgcgtg
1141  gagacggtgg  agagtggagc  catgaccaag  gacctggcgg  gctgcattca  cggcctcagc
1201  aatgtgaagc  tgaacgagca  cttcctgaac  accacggact  tcctcgacac  catcaagagc
1261  aacctggaca  gagccctggg  caggcagtag  ggggaggcgc  cacccatggc  tgcagtggag
1321  gggccaggc   tgagccggcg  ggtcctcctg  agcgcggcag  agggtgagcc  tcacagcccc
1381  tctctggagg  cctttctagg  ggatgttttt  ttataagcca  gatgttttta  aaagcatatg
1441  tgtgtttccc  ctcatggtga  cgtgaggcag  gagcagtgcg  ttttacctca  gccagtcagt
1501  atgttttgca  tactgtaatt  tatattgccc  ttggaacaca  tggtgccata  tttagctact
1561  aaaaagctct  tcacaaaa
```

What is claimed is:

1. A method of treating an IDH mutant solid tumor in a subject consisting essentially of administering to the subject a therapeutically effective amount of a composition consisting essentially of an all-trans retinoic acid (ATRA), a bexarotene, or a 13-cis retinoic acid;
   and optionally, further administering to the subject a therapeutically effective amount of Natural Killer (NK) cells.

2. The method of claim 1, wherein all-trans retinoic acid (ATRA) is selected.

3. The method of claim 1, wherein the method increases an NK-cell-mediated immune response to the cancer, a T cell-mediated immune response to the cancer, or a combination thereof.

4. The method of claim 1, wherein the solid tumor is a glioma.

5. The method of claim 1, wherein the solid tumor is a chondrosarcoma.

6. The method of claim 1, wherein expression of one or more NKG2D ligands is increased in a tumor microenvironment of the solid tumor.

7. The method of claim 6, wherein the one or more NKG2D ligands is selected from the group consisting of ULBP1 and ULBP3.

8. The method of claim 1, wherein CCL2 production is increased in a tumor microenvironment of the solid tumor.

9. The method of claim 1, wherein the method increases the number of NK cells in a tumor microenvironment of the solid tumor.

10. The method of claim 1, wherein the composition consists essentially of an all-trans retinoic acid (ATRA) effective to increase an NK-cell-mediated and/or T cell-mediated immune response to the solid tumor.

11. The method of claim 1, wherein the subject has an IDH1 mutation at arginine 132.

12. The method of claim 1, wherein the subject has an IDH2 mutation at arginine 172.

13. The method of claim 1, wherein the method increases apoptosis of tumor cells in a tumor microenvironment of the solid tumor.

14. The method of claim 1, wherein the method reduces growth of the solid tumor.

* * * * *